(12) United States Patent
Yoshida et al.

(10) Patent No.: US 9,388,101 B2
(45) Date of Patent: Jul. 12, 2016

(54) FLUORANTHENE POLYMER COMPOUND

(75) Inventors: Tomoyasu Yoshida, Tsukuba (JP);
Hidenori Hanaoka, Suita (JP); Shota Moriwaki, Ibaraki (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 875 days.

(21) Appl. No.: 13/580,766

(22) PCT Filed: Feb. 24, 2011

(86) PCT No.: PCT/JP2011/054831
§ 371 (c)(1),
(2), (4) Date: Aug. 23, 2012

(87) PCT Pub. No.: WO2011/105622
PCT Pub. Date: Sep. 1, 2011

(65) Prior Publication Data
US 2012/0313052 A1  Dec. 13, 2012

(30) Foreign Application Priority Data
Feb. 25, 2010 (JP) ................................ 2010-039984

(51) Int. Cl.
| | |
|---|---|
| H01L 51/54 | (2006.01) |
| C09K 11/06 | (2006.01) |
| C07C 35/52 | (2006.01) |
| C07C 13/62 | (2006.01) |
| C07C 13/66 | (2006.01) |
| C07C 15/20 | (2006.01) |
| C07C 15/38 | (2006.01) |
| C07C 25/22 | (2006.01) |
| C08G 61/02 | (2006.01) |
| C08G 61/12 | (2006.01) |
| H01L 51/00 | (2006.01) |
| H05B 33/14 | (2006.01) |
| H01L 51/50 | (2006.01) |

(52) U.S. Cl.
CPC ................ *C07C 35/52* (2013.01); *C07C 13/62* (2013.01); *C07C 13/66* (2013.01); *C07C 15/20* (2013.01); *C07C 15/38* (2013.01); *C07C 25/22* (2013.01); *C08G 61/02* (2013.01); *C08G 61/12* (2013.01); *C09K 11/06* (2013.01); *H01L 51/0039* (2013.01); *H01L 51/0043* (2013.01); *H05B 33/14* (2013.01); *C07C 2103/18* (2013.01); *C07C 2103/24* (2013.01); *C07C 2103/40* (2013.01); *C07C 2103/50* (2013.01); *C07C 2103/52* (2013.01); *C07C 2103/54* (2013.01); *C08G 2261/148* (2013.01); *C08G 2261/1412* (2013.01); *C08G 2261/3142* (2013.01); *C08G 2261/3162* (2013.01); *C09K 2211/1416* (2013.01); *H01L 51/5012* (2013.01)

(58) Field of Classification Search
None
See application file for complete search history.

(56) References Cited

U.S. PATENT DOCUMENTS

| | | | |
|---|---|---|---|
| 2006/0238110 A1* | 10/2006 | Shirai et al. .................. | 313/503 |
| 2007/0221915 A1 | 9/2007 | Fujita | |
| 2007/0244295 A1 | 10/2007 | Fujita | |
| 2008/0090102 A1 | 4/2008 | Fujita | |
| 2008/0241592 A1 | 10/2008 | Fujita | |
| 2009/0102371 A1* | 4/2009 | Hashimoto et al. ........... | 313/504 |

(Continued)

FOREIGN PATENT DOCUMENTS

| | | |
|---|---|---|
| JP | 2005-116238 A | 4/2005 |
| JP | 2007-254687 A | 10/2007 |

(Continued)

OTHER PUBLICATIONS

Communication dated May 27, 2014 from the Japanese Patent Office in counterpart application No. 2011-038136.

(Continued)

*Primary Examiner* — Andrew K Bohaty
(74) *Attorney, Agent, or Firm* — Sughrue Mion, PLLC

(57) ABSTRACT

A polymer compound comprising a constitutional unit represented by the formula (1):

$$\left[ \begin{array}{c} Ar^1 \\ | \\ (E)_{aa} \end{array} \right] \quad (1)$$

in the formula, $Ar^1$ represents an aromatic hydrocarbon group or an aromatic heterocyclic group, E represents a group obtained by removing one hydrogen atom in a compound represented by the formula (2):

(2)

[fluoranthene structure with substituents $R^1$ through $R^{10}$]

in the formula, $R^1$ to $R^{10}$ represents a hydrogen atom, an alkyl group, an aryl group, a monovalent aromatic heterocyclic group or a group represented by —O—$R^4$, $R^4$ represents an alkyl group, an aryl group or a monovalent aromatic heterocyclic group, and aa is an integer of 1 or more.

6 Claims, No Drawings

(56) References Cited

U.S. PATENT DOCUMENTS

| | | | |
|---|---|---|---|
| 2010/0171100 A1* | 7/2010 | Nakatani et al. | 257/40 |
| 2010/0259163 A1 | 10/2010 | Mizuki et al. | |
| 2010/0264814 A1 | 10/2010 | Ito et al. | |
| 2010/0289014 A1 | 11/2010 | Ito et al. | |

FOREIGN PATENT DOCUMENTS

| | | | | |
|---|---|---|---|---|
| JP | 2007-284491 A | 11/2007 | | |
| JP | 2008-144129 A | 6/2008 | | |
| JP | 2008-244053 A | 10/2008 | | |
| JP | 2012-500886 A | 1/2012 | | |
| WO | WO 2006137434 A1 * | 12/2006 | | C08G 61/12 |
| WO | 2009/066666 A1 | 5/2009 | | |
| WO | 2009/075203 A1 | 6/2009 | | |
| WO | 2009/075223 A1 | 6/2009 | | |
| WO | 2009/084548 A1 | 7/2009 | | |
| WO | 2010/023443 A2 | 3/2010 | | |

OTHER PUBLICATIONS

Communication dated Feb. 3, 2015 from the Japanese Patent Office in counterpart application No. 2011-038136.

Christophe Ego, et al., "Triphenylamine-Substituted Polyfluorene—A Stable Blue-Emitter with Improved Charge Injection for Light-Emitting Diodes", Advanced Materials, vol. 14, No. 11, Jun. 5, 2002, pp. 809-811.

Machine-generated English translation of JP 2005-116238A to TDK Corp, Year: 2005.

* cited by examiner

FLUORANTHENE POLYMER COMPOUND

CROSS REFERENCE TO RELATED APPLICATIONS

This application is a National Stage of International Application No. PCT/JP2011/054831 filed on Feb. 24, 2011, which claims priority from Japanese Patent Application No. 2010-039984, filed on Feb. 25, 2010, the contents of all of which are incorporated herein by reference in their entirety.

TECHNICAL FIELD

The present invention relates to a fluoranthene polymer compound, a production method thereof, and a polymer composition, a solution, an organic film, a light emitting device, a surface light source and a display comprising the compound, and, a raw material compound thereof.

BACKGROUND ART

High molecular weight light emitting materials and charge transporting materials are soluble in a solvent and capable of forming an organic layer in a light emitting device by a coating method, thus, variously investigated, and for example, a polyfluorene having a triphenylaminediyl group on the side chain is known as a polymer compound having a functional substituent such as a hole injection and transporting group, an electron injection and transporting group, a light emitting group or the like on the side chain of the conjugated main chain (see, Advanced Materials; 2002, Vol. 14, No. 11, p. 809).

DISCLOSURE OF THE INVENTION

However, when the above-described polymer compound is used as a light emitting material for a light emitting device, the maximum light emission efficiency is not sufficient yet.

The present invention has an object of providing a polymer compound useful for production of a light emitting device excellent in the maximum light emission efficiency. The present invention also has an object of providing a polymer composition, a solution, an organic film, a light emitting device, a surface light source and a display, comprising this polymer compound. Further, the present invention has an object of providing a method of producing this polymer compound and a compound which is useful for production of this polymer compound.

The present invention includes the following inventions.

<1> A polymer compound comprising a constitutional unit represented by the following formula (1):

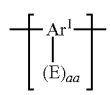
(1)

in the formula (1), $Ar^1$ represents an unsubstituted or substituted aromatic hydrocarbon group or an unsubstituted or substituted aromatic heterocyclic group; E represents a group obtained by removing one hydrogen atom in a compound represented by the following formula (2):

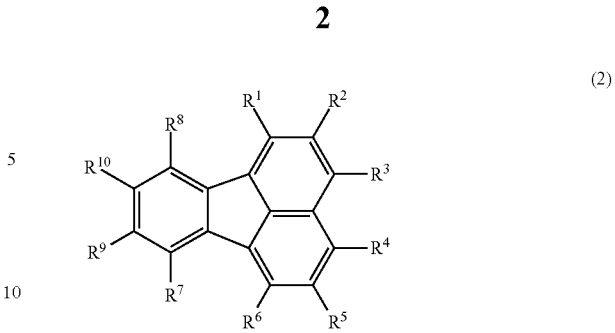
(2)

in the formula (2), $R^1$, $R^2$, $R^3$, $R^4$, $R^5$, $R^6$, $R^7$, $R^8$, $R^9$ and $R^{10}$ each independently represent a hydrogen atom, an alkyl group, an aryl group, a monovalent aromatic heterocyclic group or a group represented by —O—$R^A$, and these groups may have a substituent; $R^A$ represents an alkyl group, an aryl group or a monovalent aromatic heterocyclic group, and these groups may have a substituent; when there are a plurality of $R^A$s, these may be the same or different; $R^1$ and $R^2$, $R^2$ and $R^9$, $R^3$ and $R^4$, $R^4$ and $R^5$, $R^5$ and $R^6$, $R^6$ and $R^7$, $R^7$ and $R^9$, $R^9$ and $R^{10}$, $R^1$ and $R^8$, and $R^{10}$ and $R^8$ may each be linked to each other to form a ring;

aa is an integer of 1 or more.

When a ring is formed, the ring to be formed includes unsubstituted or substituted benzene rings. The substituent carried on the substituted benzene ring includes an alkyl group, an aryl group, a monovalent aromatic heterocyclic group or a group represented by —O—$R^A$.

<2> The polymer compound according to <1>, wherein E represents a group obtained by removing one hydrogen atom in a compound represented by the following formula (3):

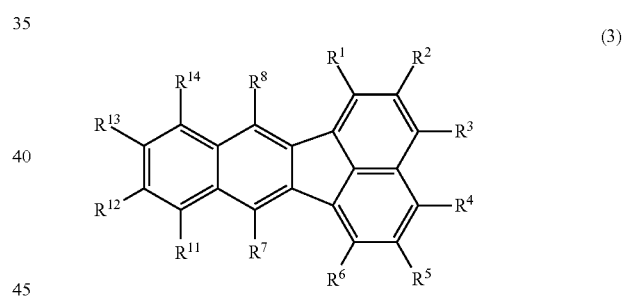
(3)

in the formula (3), $R^1$, $R^2$, $R^3$, $R^4$, $R^5$, $R^6$, $R^7$ and $R^8$ each independently represent a hydrogen atom, an alkyl group, an aryl group, a monovalent aromatic heterocyclic group or a group represented by —O—$R^A$, and these groups may have a substituent; $R^1$ and $R^2$, $R^2$ and $R^3$, $R^3$ and $R^4$, $R^4$ and $R^5$, $R^5$ and $R^6$, $R^6$ and $R^7$, and $R^1$ and $R^8$ may each be linked to each other to form a ring; $R^{11}$, $R^{12}$, $R^{13}$ and $R^{14}$ each independently represent a hydrogen atom, an alkyl group, an aryl group, a monovalent aromatic heterocyclic group or a group represented by —O—$R^A$, and these groups may have a substituent; $R^A$ is defined above; when there are a plurality of $R^A$s, these may be the same or different.

When a ring is formed, the ring to be formed includes unsubstituted or substituted benzene rings. The substituent carried on the substituted benzene ring includes an alkyl group, an aryl group, a monovalent aromatic heterocyclic group or a group represented by —O—$R^A$.

<3> The polymer compound according to <1> or <2>, wherein the constitutional unit represented by the above-described formula (1) is a constitutional unit represented by the following formula (4):

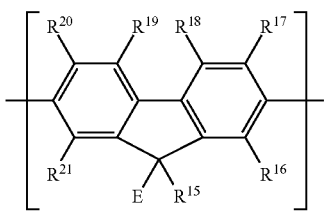
(4)

in the formula (4), $R^{15}$ represents a hydrogen atom, an alkyl group, an aryl group, a monovalent aromatic heterocyclic group, a group represented by —O—$R^A$ or a group represented by E, and these groups may have a substituent; $R^{16}$, $R^{17}$, $R^{18}$, $R^{19}$, $R^{20}$ and $R^{21}$ each independently represent a hydrogen atom, an alkyl group, an aryl group, a monovalent aromatic heterocyclic group or a group represented by —O—$R^A$, and these groups may have a substituent; $R^A$ is defined above; when there are a plurality of $R^A$s, these may be the same or different; $R^{17}$ and $R^{18}$, and $R^{19}$ and $R^{20}$ may each be linked to each other to form a ring; E is defined above.

When a ring is formed, the ring to be formed includes unsubstituted or substituted benzene rings. The substituent carried on the substituted benzene ring includes an alkyl group, an aryl group, a monovalent aromatic heterocyclic group or a group represented by —O—$R^A$.

<4> The polymer compound according to any one of <1> to <3>, comprising a first constitutional unit represented by the above-described formula (1) and a second constitutional unit represented by the following formula (5):

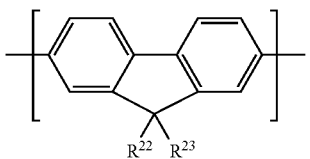
(5)

in the formula (5), $R^{22}$ and $R^{23}$ each independently represent an alkyl group, an aryl group or a monovalent aromatic heterocyclic group, and these groups may have a substituent.

<5> The polymer compound according to any one of <1> to <4>, comprising a first constitutional unit represented by the above-described formula (1), a second constitutional unit represented by the above-described formula (5), and at least one constitutional unit selected from the group consisting of a third constitutional unit represented by the following formula (6) and a fourth constitutional unit represented by the following formula (7):

(6)

in the formula (6), $Ar^2$ represents an arylene group, a divalent aromatic heterocyclic group or a divalent group formed by linking two or more identical or different groups selected from the group consisting of arylene groups and divalent aromatic heterocyclic groups; $Ar^2$ may have at least one substituent selected from the group consisting of an alkyl group, an aryl group, a monovalent aromatic heterocyclic group, a group represented by —O—$R^A$, a group represented by —S—$R^A$, a group represented by —C(=O)—$R^A$, a group represented by —C(=O)—O—$R^A$, a group represented by —N($R^A$)$_2$, a cyano group and a fluorine atom; $R^A$ is defined above; when there are a plurality of $R^A$s, these may be the same or different;

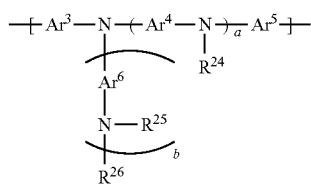
(7)

in the formula (7), $Ar^3$, $Ar^4$, $Ar^5$ and $Ar^6$ each independently represent an unsubstituted or substituted arylene group, an unsubstituted or substituted divalent aromatic heterocyclic group or a divalent group formed by linking two or more identical or different groups selected from the group consisting of arylene groups and divalent aromatic heterocyclic groups; $Ar^3$ and $Ar^4$, $Ar^3$ and $Ar^6$, and $Ar^4$ and $Ar^5$ may each be linked via a single bond or linked via a group represented by —O—, —S—, —C(=O)—, —C(=O)—O—, —N($R^A$)—, —C(=O)—N($R^A$)— or —C($R^A$)$_2$— to form a ring; $R^A$ is defined above; when there are a plurality of $R^A$s, these may be the same or different; $R^{24}$, $R^{25}$ and $R^{26}$ each independently represent a hydrogen atom, an alkyl group, an aryl group, a monovalent heterocyclic group or an arylalkyl group, and these groups may have a substituent; a represents an integer of 0 to 3, and b represents 0 or 1.

<6> The polymer compound according to <4> or <5>, comprising a first constitutional unit represented by the above-described formula (1), a second constitutional unit represented by the above-described formula (5) and a fourth constitutional unit represented by the above-described formula (7).

<7> The polymer compound according to any one of <1>, <3> to <6>, wherein the above-described E represents a group obtained by removing one hydrogen atom from the group or atom represented by $R^9$ or $R^{10}$ in the above-described formula (2).

<8> The polymer compound according to any one of <1> to <6>, wherein the above-described E represents a group obtained by removing one hydrogen atom from the group or atom represented by $R^3$ or $R^4$ in the above-described formula (2) or (3).

<9> The polymer compound according to any one of <2> to <6>, wherein the above-described E represents a group obtained by removing one hydrogen atom from the group or atom represented by $R^{12}$ or $R^{13}$ in the above-described formula (3).

<10> The polymer compound according to any one of <1> to <9>, wherein the polymer compound is a conjugated polymer compound.

<11> The polymer compound according to any one of <4> to <10>, wherein the content of the above-described first constitutional unit is 0.1 to 50 mol % with respect to the total content of the above-described first constitutional unit, the above-described second constitutional unit, the above-described third constitutional unit and the above-described fourth constitutional unit.

<12> The polymer compound according to any one of <4> to <11>, wherein the total content of the above-described first constitutional unit, the above-described second constitutional unit, the above-described third constitutional unit and the above-described fourth constitutional unit is 80 to 100 wt % with respect to the total amount of the above-described polymer compound.

<13> A compound represented by the following formula (1M):

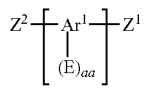

(1M)

in the formula (1M), $Ar^1$ represents an unsubstituted or substituted aromatic hydrocarbon group or an unsubstituted or substituted aromatic heterocyclic group; E represents a group obtained by removing one hydrogen atom in a compound represented by the following formula (2):

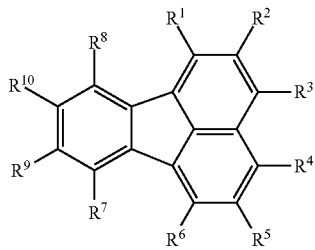

(2)

in the formula (2), $R^1$, $R^2$, $R^3$, $R^4$, $R^5$, $R^6$, $R^7$, $R^8$, $R^9$ and $R^{16}$ each independently represent a hydrogen atom, an alkyl group, an aryl group, a monovalent aromatic heterocyclic group or a group represented by —O—$R^4$, and these groups may have a substituent; $R^4$ represents an alkyl group, an aryl group or a monovalent aromatic heterocyclic group, and these groups may have a substituent; when there are a plurality of $R^4$s, these may be the same or different; $R^1$ and $R^2$, $R^2$ and $R^2$, $R^3$ and $R^4$, $R^4$ and $R^5$, $R^5$ and $R^6$, $R^6$ and $R^7$, $R^7$ and $R^9$, $R^9$ and $R^{10}$, $R^1$ and $R^8$, and $R^{16}$ and $R^8$ may each be linked to each other to form a ring;

$Z^1$ and $Z^2$ each independently represent any group selected from the group consisting of Substituent Group A and Substituent Group B; aa is an integer of 1 or more;

<Substituent Group A>
a chlorine atom, a bromine atom, an iodine atom, groups represented by —O—S(=O)$_2R^{27}$ ($R^{27}$ represents an alkyl group, or an aryl group optionally substituted by an alkyl group, an alkoxy group, a nitro group, a fluorine atom or a cyano group);

<Substituent Group B>
groups represented by —B(OR$^{28}$)$_2$ ($R^{28}$ represents a hydrogen atom or an alkyl group, two $R^{28}$s may be the same or different, and may be linked to each other to form a ring), groups represented by —BF$_4^-$Q$^1$ (Q$^1$ represents a monovalent cation of lithium, sodium, potassium, rubidium or cesium), groups represented by —MgY$^1$ (Y$^1$ represents a chlorine atom, a bromine atom or an iodine atom), groups represented by —ZnY$^2$ (Y$^2$ represents a chlorine atom, a bromine atom or an iodine atom), groups represented by —Sn(R$^{29}$)$_3$ (R$^{29}$ represents a hydrogen atom or an alkyl group; the three R$^{29}$s may be the same or different, and may be linked to each other to form a ring).

<14> A method of producing the polymer compound according to any one of <4> to <12>, comprising a step of polymerizing a compound represented by the following formula (1M) and a compound represented by the following formula (5M):

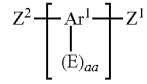

(1M)

in the formula (1M), $Ar^1$ represents an unsubstituted or substituted aromatic hydrocarbon group or an unsubstituted or substituted aromatic heterocyclic group; E represents a group obtained by removing one hydrogen atom in a compound represented by the following formula (2):

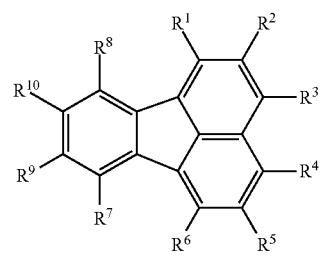

(2)

in the formula (2), $R^1$, $R^2$, $R^3$, $R^4$, $R^5$, $R^6$, $R^7$, $R^8$, $R^9$ and $R^{10}$ each independently represent a hydrogen atom, an alkyl group, an aryl group, a monovalent aromatic heterocyclic group or a group represented by —O—$R^4$, and these groups may have a substituent; $R^4$ represents an alkyl group, an aryl group or a monovalent aromatic heterocyclic group, and these groups may have a substituent; when there are a plurality of $R^4$s, these may be the same or different; $R^1$ and $R^2$, $R^2$ and $R^3$, $R^3$ and $R^4$, $R^4$ and $R^5$, $R^5$ and $R^6$, $R^6$ and $R^7$, $R^7$ and $R^9$, $R^9$ and $R^{10}$, $R^1$ and $R^9$, and $R^{10}$ and $R^8$ may each be linked to each other to form a ring;

$Z^1$ and $Z^2$ each independently represent any group selected from the group consisting of Substituent Group A and Substituent Group B; aa is an integer of 1 or more;

<Substituent Group A>
a chlorine atom, a bromine atom, an iodine atom, groups represented by —O—S(=O)$_2R^{27}$ ($R^{27}$ represents an alkyl group, or an aryl group optionally substituted by an alkyl group, an alkoxy group, a nitro group, a fluorine atom or a cyano group);

<Substituent Group B>
groups represented by —B(OR$^{28}$)$_2$ ($R^{28}$ represents a hydrogen atom or an alkyl group, two $R^{28}$s may be the same or different, and may be linked to each other to form a ring), groups represented by —BF$_4^-$Q$^1$ (Q$^1$ represents a monovalent cation of lithium, sodium, potassium, rubidium or cesium), groups represented by —MgY$^1$ (Y$^1$ represents a chlorine atom, a bromine atom or an iodine atom), groups represented by —ZnY$^2$ (Y$^2$ represents a chlorine atom, a bromine atom or an iodine atom), groups represented by —Sn(R$^{29}$)$_3$ (R$^{29}$ represents a hydrogen atom or an alkyl group, the three R$^{29}$s may be the same or different, and may be linked to each other to form a ring);

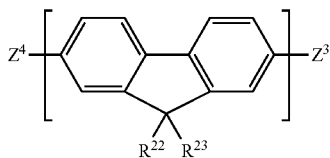

(5M)

in the formula (5M), $R^{22}$ and $R^{23}$ each independently represent an alkyl group, an aryl group or a monovalent aromatic heterocyclic group, and these groups may have a substituent; $Z^3$ and $Z^4$ each independently represent any group selected from the group consisting of the above-described Substituent Group A and the above-described Substituent Group B.

<15> A polymer composition comprising the polymer compound according to any one of <1> to <12> and at least one material selected from the group consisting of hole transporting materials, electron transporting materials and light emitting materials.

<16> A solution comprising the polymer compound according to any one of <1> to <12> and a solvent.

<17> An organic film comprising the polymer compound according to any one of <1> to <12> or the polymer composition according to <15>.

<18> A light emitting device having the organic film according to <17>.

<19> A surface light source having the light emitting device according to <18>.

<20> A display having the light emitting device according to <18>.

MODE FOR CARRYING OUT THE INVENTION

Suitable embodiments of the present invention will be described in detail below.

In the present specification, "constitutional unit" means one or more unit structures present in a polymer compound. It is preferable that "constitutional unit" is contained in the form of "repeating unit" (namely, two or more unit structures present in a polymer compound) in a polymer compound. "n-Valent aromatic heterocyclic group" means an atomic group obtained by removing n hydrogen atoms directly linked to the aromatic ring of a heterocyclic compound having aromaticity, and includes groups having a condensed ring structure. "Heterocyclic compound" includes organic compounds having a cyclic structure in which atoms constituting the ring include not only a carbon atom but also a hetero atom such as an oxygen atom, a sulfur atom, a nitrogen atom, a phosphorus atom, a boron atom, a silicon atom and the like. "Aromatic heterocyclic compound" is a heterocyclic compound comprising a hetero atom such as oxadiazole, thiadiazole, thiazole, oxazole, thiophene, pyrrole, phosphole, furan, pyridine, pyrazine, pyrimidine, triazine, pyridazine, quinoline, isoquinoline, carbazole, dibenzophosphole and the like, and includes compounds in which the heterocyclic ring itself shows aromaticity, and compounds in which the heterocyclic ring itself comprising a hetero atom does not show aromaticity but an aromatic ring is condensed to the heterocyclic ring such as phenoxazine, phenothiazine, dibenzothiophene, dibenzofuran, dibenzoborole, dibenzosilole, benzopyran and the like. "n-Valent condensed aromatic heterocyclic group" includes the above-described "n-valent aromatic heterocyclic groups" having a condensed ring. In the present specification, groups represented by E are not included in the aryl group.

In the present specification, Me represents a methyl group and Et represents an ethyl group in structural formulae.

<Polymer Compound>
[First Constitutional Unit]

The polymer compound according to the present invention contains a constitutional unit represented by the above-described formula (1) (hereinafter, referred to as "first constitutional unit".). These first constitutional units may be contained singly or in combination in the polymer compound.

In the above-described formula (1), aa is an integer of 1 or more, and for example 1, 2, 3, 4, 5 or 6. aa is preferably 1 or 2, more preferably 1 since the maximum light emission efficiency is more excellent The upper limit of aa is preferably 4 since synthesis of a polymer compound is easy.

In the above-described formula (2), the alkyl group represented by $R^1$ to $R^{10}$ may be any of linear, branched or cyclic, has a carbon atom number of usually 1 to 20, more preferably 1 to 12. This carbon atom number does not include the carbon atom number of a substituent. The above-described alkyl group includes a methyl group, an ethyl group, a propyl group, an isopropyl group, a butyl group, an isobutyl group, a tert-butyl group, a pentyl group, an isoamyl group, a hexyl group, a cyclohexyl group, a heptyl group, an octyl group, a 2-ethylhexyl group, a nonyl group, a decyl group, a 3,7-dimethyloctyl group, a dodecyl group and the like. A hydrogen atom in the above-described alkyl group may be substituted by an aryl group, a monovalent aromatic heterocyclic group, a group represented by —O—$R^A$, a group represented by —S—$R^A$, a group represented by —C(=O)—$R^A$, a group represented by —C(=O)—O—$R^A$, a cyano group or a fluorine atom. Exemplified as the alkyl group substituted by a fluorine atom are a trifluoromethyl group, a pentafluoroethyl group, a perfluorobutyl group, a perfluorohexyl group and a perfluorooctyl group.

In the above-described formula (2), the aryl group represented by $R^1$ to $R^{10}$ is an atomic group obtained by removing one hydrogen atom directly linked to the aromatic ring of an aromatic hydrocarbon, and includes groups having a condensed ring. The above-described aryl group has a carbon atom number of usually 6 to 60, preferably 6 to 48, more preferably 6 to 20, further preferably 6 to 14. This carbon atom number does not include the carbon atom number of a substituent. The above-described aryl group includes a phenyl group, a 1-naphthyl group, a 2-naphthyl group, a 1-anthracenyl group, a 2-anthracenyl group, a 9-anthracenyl group, a 1-tetracenyl group, a 2-tetracenyl group, a 5-tetracenyl group, a 1-pyrenyl group, a 2-pyrenyl group, a 4-pyrenyl group, a 2-perylenyl group, a 3-perylenyl group, a 2-fluorenyl group, a 3-fluorenyl group, a 4-fluorenyl group, a 1-biphenylyl group, a 2-biphenylyl group, a 2-phenanthrenyl group, a 9-phenanthrenyl group, a 6-chrysenyl group, a 1-coronenyl group and the like. A hydrogen atom in the above-described aryl group may be substituted by an alkyl group, an aryl group, a monovalent aromatic heterocyclic group, a group represented by —O—$R^A$, a group represented by —S—$R^A$, a group represented by —C(=O)—$R^A$, a group represented by —C(=O)—O—$R^A$, a cyano group or a fluorine atom.

In the formula (2), the monovalent aromatic heterocyclic group represented by $R^1$ to $R^{10}$ has a carbon atom number of usually 3 to 60, preferably 3 to 20. This carbon atom number does not include the carbon atom number of a substituent. The above-described monovalent aromatic heterocyclic group includes a 1,3,4-oxadiazol-2-yl group, a 1,3,4-thiadiazol-2-yl group, a 2-thiazolyl group, a 2-oxazolyl group, a 2-thienyl group, a 2-pyrrolyl group, a 2-furyl group, a 2-pyridyl group, a 3-pyridyl group, a 4-pyridyl group, a 2-pyrazinyl group, a 2-pyrimidinyl group, a 2-triazinyl group, a 3-pyridazinyl group, a 5-quinolyl group, a 5-isoquinolyl group, a 2-carbazolyl group, a 3-carbazolyl group, a 2-phenoxazinyl group, a 3-phenoxazinyl group, a 2-phenothiazinyl group, a 3-phenothiazinyl group and the like. A hydrogen atom in the above-described monovalent aromatic heterocyclic group may be substituted by an alkyl group, an aryl group, a monovalent aromatic heterocyclic group, a group represented by —O—$R^A$, a group represented by —S—$R^A$, a group represented by —C(=O)—$R^A$, a group represented by —C(=O)—O—$R^A$, a cyano group or a fluorine atom.

As the alkyl group, the aryl group and the monovalent aromatic heterocyclic group represented by $R^A$, the same groups as the above-described groups represented by $R^1$ are exemplified.

In the above-described formula (2), the group represented by —O—$R^A$ represented by $R^1$ to $R^{10}$ includes alkoxy groups having a linear, branched or cyclic alkyl group, when $R^A$ is an alkyl group. The above-described alkoxy group has a carbon atom number of usually 1 to 20. The above-described alkoxy group includes a methoxy group, an ethoxy group, a propyloxy group, an isopropyloxy group, a butoxy group, an isobutoxy group, a tert-butoxy group, a pentyloxy group, a hexyloxy group, a nonyloxy group, a decyloxy group, a 3,7-dimethyloctyloxy group, a dodecyloxy group, a trifluoromethoxy group, a pentafluoroethoxy group, a perfluorobutoxy group, a perfluorohexyloxy group, a perfluorooctyloxy group, a methoxymethyloxy group, a 2-methoxyethyloxy group, a 2-ethoxyethyloxy group and the like.

In the above-described formula (2), the group represented by —O—$R^A$ represented by $R^1$ to $R^{10}$ includes aryloxy groups having a carbon atom number of usually 6 to 60, when $R^A$ is an aryl group. This aryl group portion includes the same groups as the above-described aryl groups represented by $R^1$. The above-described aryloxy group includes a phenoxy group, $C_1$ to $C_{12}$ alkoxyphenoxy groups ("$C_1$ to $C_{12}$ alkoxy" denotes that the alkoxy portion has a carbon atom number of 1 to 12, the same shall apply hereinafter.), $C_1$ to $C_{12}$ alkylphenoxy groups ("$C_1$ to $C_{12}$ alkyl" denotes that the alkyl portion has a carbon atom number of 1 to 12, the same shall apply hereinafter.), a 1-naphthyloxy group, a 2-naphthyloxy group, a pentafluorophenyloxy group and the like.

In the above-described formula (2), the group represented by —O—$R^A$ represented by $R^1$ to $R^{10}$ includes groups having a carbon atom number of usually 3 to 60, preferably 3 to 20, when $R^A$ is a monovalent aromatic heterocyclic group. This monovalent aromatic heterocyclic group includes the same groups as the above-described monovalent aromatic heterocyclic group represented by $R^1$.

In the group obtained by removing one hydrogen atom in a compound represented by the above-described formula (2), $R^9$ and $R^{10}$ linked to adjacent carbon atoms may form a ring together with the carbon atoms. The ring to be formed includes unsubstituted or substituted benzene rings.

The substituent carried on the substituted benzene ring includes an alkyl group, an aryl group, a monovalent aromatic heterocyclic group or a group represented by —O—$R^A$.

In the formula (2), $R^1$ to $R^6$ and $R^9$ to $R^{10}$ represent preferably a hydrogen atom, an alkyl group or an aryl group.

In the formula (2), $R^7$ and $R^8$ represent more preferably an alkyl group, an aryl group or a monovalent aromatic heterocyclic group, further preferably an aryl group.

When the above-described E is a group obtained by removing one hydrogen atom in a compound represented by the above-described formula (2), it is preferable that E is a group obtained by removing one hydrogen atom from any one of groups or atoms represented by $R^2$, $R^3$, $R^4$, $R^5$, $R^9$ or $R^{10}$ in a compound represented by the formula (2), it is more preferable that E is a group obtained by removing one hydrogen atom from any one of groups or atoms represented by $R^3$ or $R^4$ in a compound represented by the formula (2) since light emission efficiency is excellent and monomer synthesis is easy, and it is more preferable that E is a group obtained by removing one hydrogen atom from groups or atoms represented by $R^9$ or $R^{10}$ in a compound represented by the formula (2) since light emission efficiency and heat resistance are excellent and monomer synthesis is easy. The group obtained by removing one hydrogen atom from any one of atoms (hydrogen atoms) represented by $R^2$, $R^3$, $R^4$, $R^5$, $R^9$ or $R^{10}$ in a compound represented by the formula (2) indicates a group in which any one of $R^2$, $R^3$, $R^4$, $R^5$, $R^9$ or $R^{10}$ in the formula (2) is a single bond.

The group obtained by removing one hydrogen atom in a compound represented by the above-described formula (2) includes groups represented by the following formula (2-1).

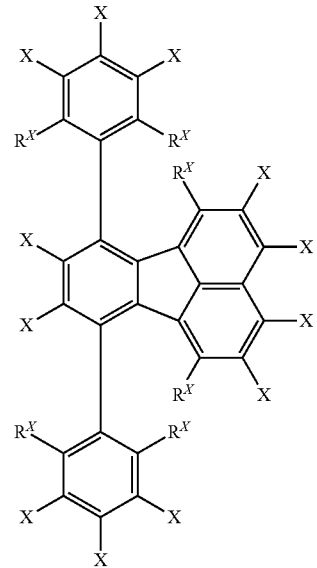

(2-1)

[in the formula (2-1), one of a plurality of Xs represents a connecting bond and others represent a hydrogen atom, an alkyl group, an aryl group, a monovalent aromatic heterocyclic group or a group represented by —O—$R^A$. $R^X$ represents a hydrogen atom, an alkyl group, an aryl group, a monovalent aromatic heterocyclic group or a group represented by —O—$R^A$, and these groups may have a substituent. A plurality of Xs and a plurality of $R^X$s may each be the same or different. $R^A$ is defined above.]

The group obtained by removing one hydrogen atom in a compound represented by the above-described formula (2) in which $R^9$ and $R^{10}$ linked to adjacent carbon atoms form a ring together with the carbon atoms includes, for example, groups obtained by removing one hydrogen atom in compounds represented by the following formula (3) and the following formula (8), and preferable are groups obtained by removing one hydrogen atom in a compound represented by the following formula (3), more preferable are groups obtained by removing one hydrogen atom in a compound represented by the following formula (3) in which the number of carbon atoms constituting a benzofluoranthene ring is 24 or less, since light emission efficiency is excellent and monomer synthesis is easy.

In the following formula (3), when $R^1$ and $R^2$, $R^2$ and $R^3$, $R^3$ and $R^4$, $R^4$ and $R^5$, $R^5$ and $R^6$, $R^6$ and $R^7$, and $R^1$ and $R^8$ are each linked to each other to form a ring, "the number of carbon atoms constituting a benzofluoranthene ring" includes also the number of carbon atoms of these rings.

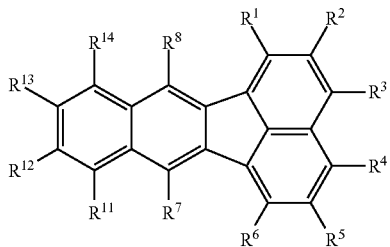
(3)

[in the formula (3), $R^1$, $R^2$, $R^3$, $R^4$, $R^5$, $R^6$, $R^7$ and $R^8$ each independently represent a hydrogen atom, an alkyl group, an aryl group, a monovalent aromatic heterocyclic group or a group represented by —O—$R^A$, and these groups may have a substituent. $R^1$ and $R^2$, $R^2$ and $R^3$, $R^3$ and $R^4$, $R^4$ and $R^5$, $R^5$ and $R^6$, $R^6$ and $R^7$, and $R^1$ and $R^8$ may each be linked to each other to form a ring. $R^{11}$, $R^{12}$, $R^{13}$ and $R^{14}$ each independently represent a hydrogen atom, an alkyl group, an aryl group, a monovalent aromatic heterocyclic group or a group represented by —O—$R^A$, and these groups may have a substituent. $R^A$ is defined above. When there are a plurality of $R^A$s, these may be the same or different.]

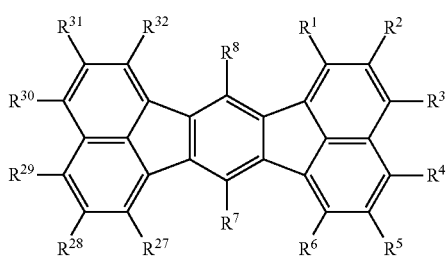
(8)

[in the formula (8), $R^1$, $R^2$, $R^3$, $R^4$, $R^5$, $R^6$, $R^7$ and $R^8$ each independently represent a hydrogen atom, an alkyl group, an aryl group, a monovalent aromatic heterocyclic group or a group represented by —O—$R^A$, and these groups may have a substituent. $R^1$ and $R^2$, $R^2$ and $R^3$, $R^3$ and $R^4$, $R^4$ and $R^5$, $R^5$ and $R^6$, $R^6$ and $R^7$, and $R^1$ and $R^8$ may each be linked to each other to form a ring. $R^{27}$, $R^{28}$, $R^{29}$, $R^{30}$, $R^{31}$ and $R^{32}$ each independently represent a hydrogen atom, an alkyl group, an aryl group, a monovalent aromatic heterocyclic group or a group represented by —O—$R^A$, and these groups may have a substituent. $R^A$ is defined above. When there are a plurality of $R^A$s, these may be the same or different.]

When the above-described E is a group obtained by removing one hydrogen atom in a compound represented by the above-described formula (3), it is preferable that E is a group obtained by removing one hydrogen atom from any one of groups or atoms represented by $R^2$, $R^3$, $R^4$, $R^5$, $R^{12}$ or $R^{13}$ in a compound represented by the formula (3), and it is more preferable that E is a group obtained by removing one hydrogen atom from any one of groups or atoms represented by $R^3$, $R^4$, $R^{12}$ or $R^{13}$ in a compound represented by the formula (3) since light emission efficiency is excellent and monomer synthesis is easy. The group obtained by removing one hydrogen atom from any one of atoms (hydrogen atoms) represented by $R^2$, $R^3$, $R^4$, $R^5$, $R^{12}$ or $R^{13}$ in a compound represented by the formula (3) indicates a group in which any one of $R^2$, $R^3$, $R^4$, $R^5$, $R^{12}$ or $R^{13}$ in the formula (3) is a single bond.

In the above-described formula (3), $R^7$ and $R^8$ represent preferably an alkyl group, an aryl group, or a monovalent aromatic heterocyclic group, more preferably an aryl group, since light emission efficiency and durability thereof are excellent.

The group obtained by removing one hydrogen atom in a compound represented by the above-described formula (3) includes groups represented by the following formula (3-1).

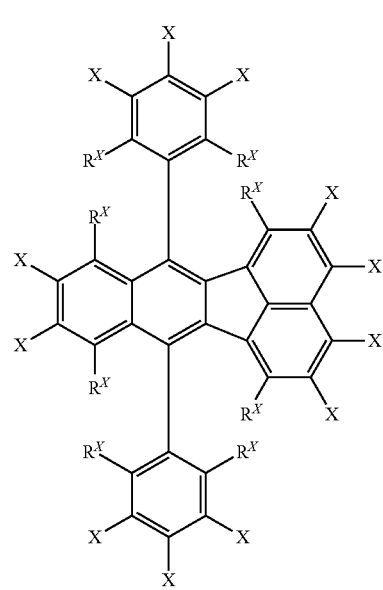
(3-1)

[in the formula (3-1), one of a plurality of Xs represents a connecting bond and others represent a hydrogen atom, an alkyl group, an aryl group, a monovalent aromatic heterocyclic group or a group represented by —O—$R^A$, and these groups may have a substituent. $R^X$ represents a hydrogen atom, an alkyl group, an aryl group, a monovalent aromatic heterocyclic group or a group represented by —O—$R^A$, and these groups may have a substituent. A plurality of Xs and a plurality of $R^X$s may each be the same or different. $R^A$ is defined above.]

Examples of the compound represented by the above-described formula (2) include compounds represented by the following formulae (1-001) to (1-061).

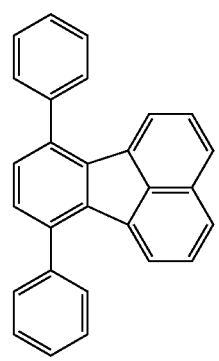
(1-001)

-continued
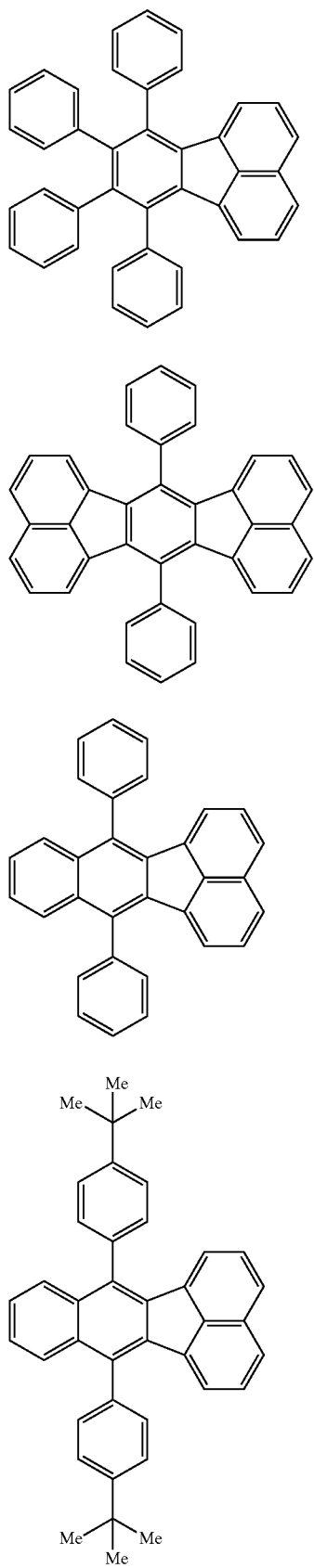
(1-002)
(1-003)
(1-004)
(1-005)
-continued
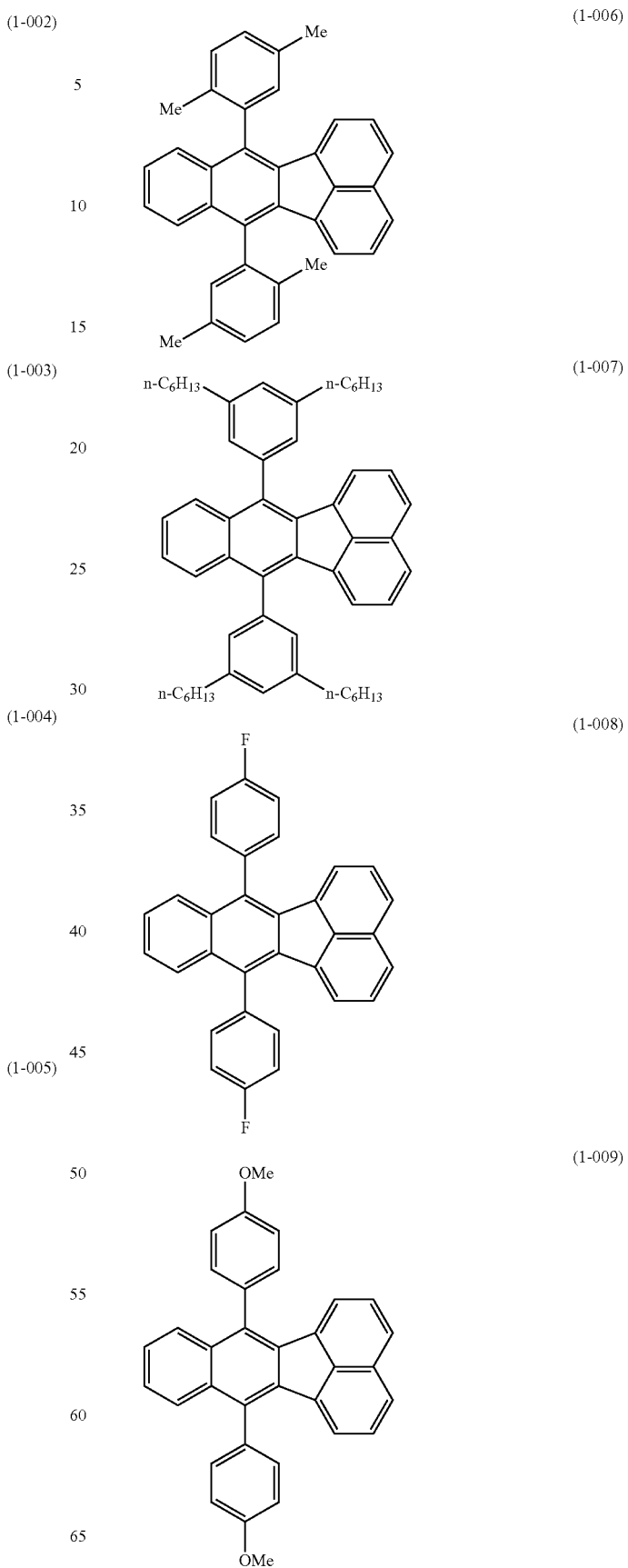
(1-006)
(1-007)
(1-008)
(1-009)

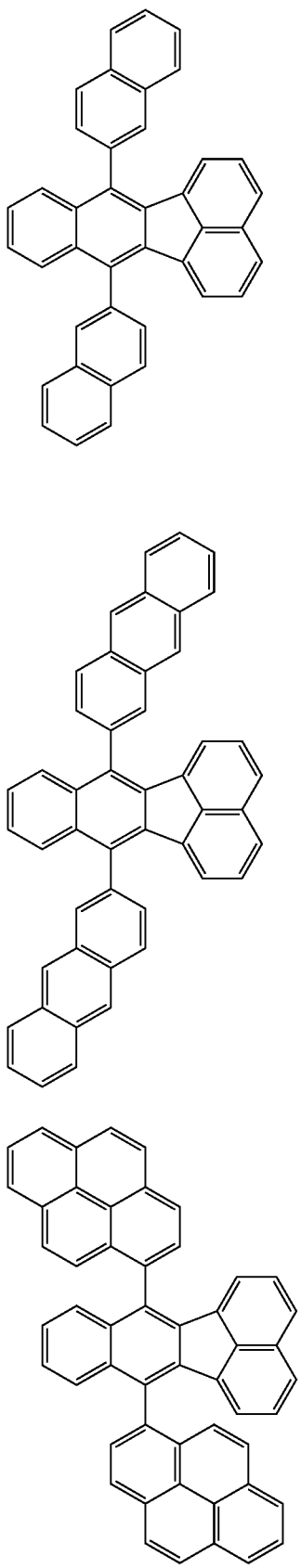
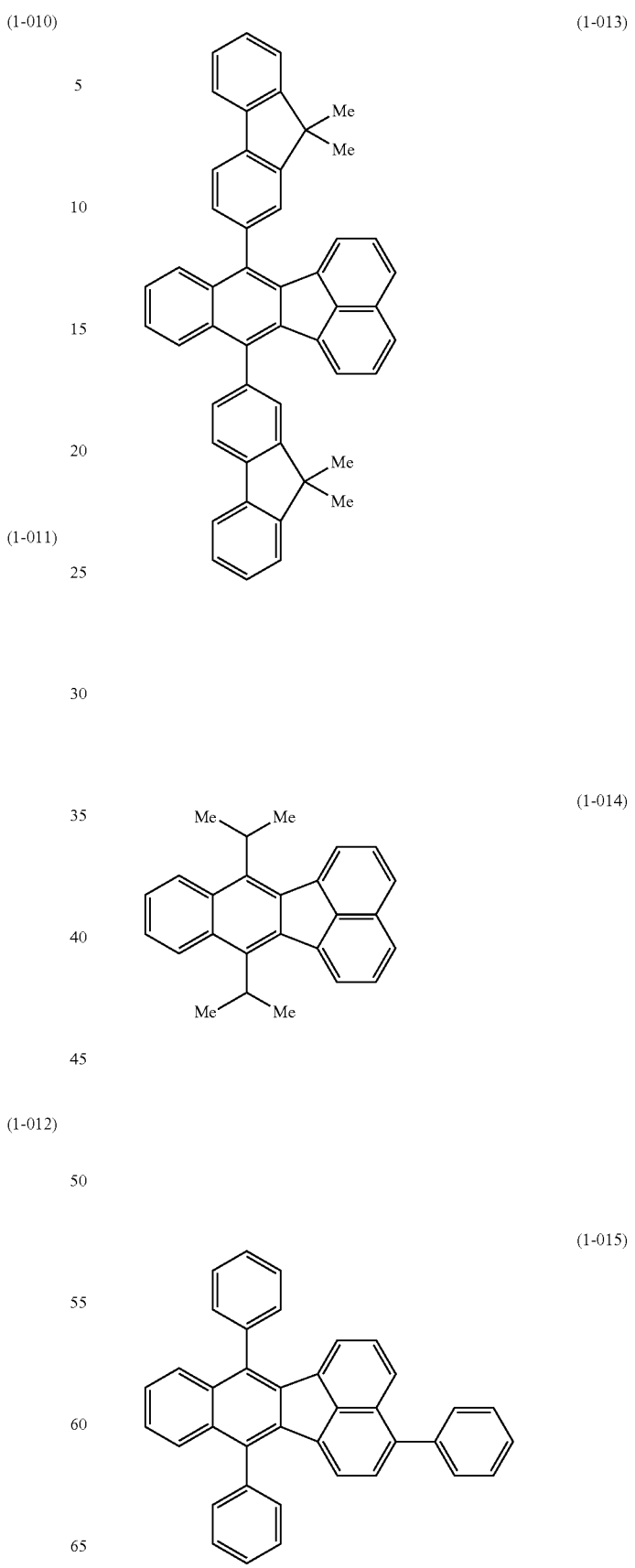

(1-016)
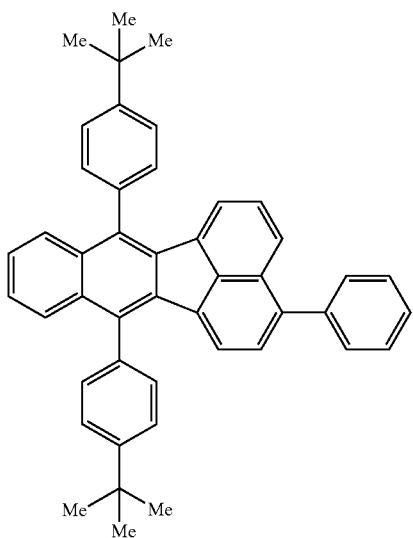
(1-017)
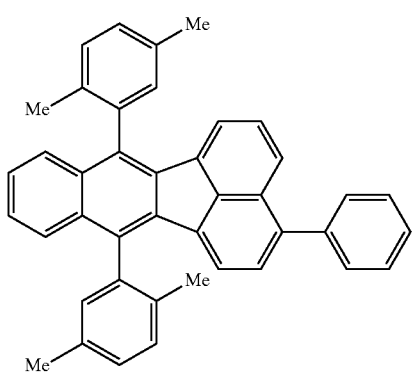
(1-018)
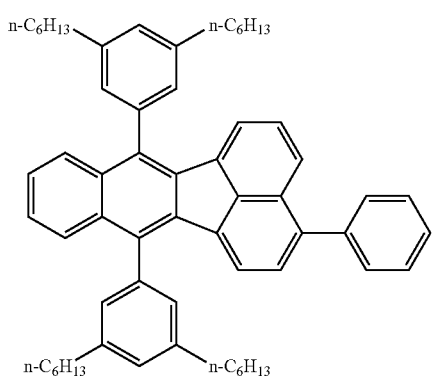
(1-019)
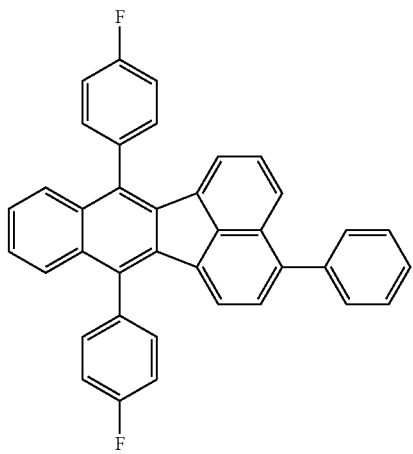
(1-020)
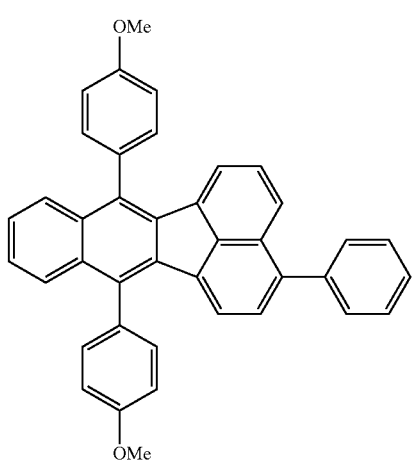
(1-021)
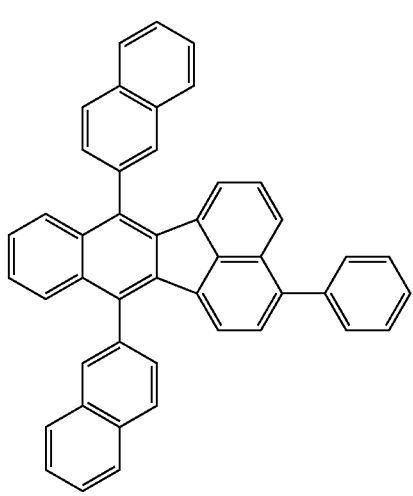

(1-022)
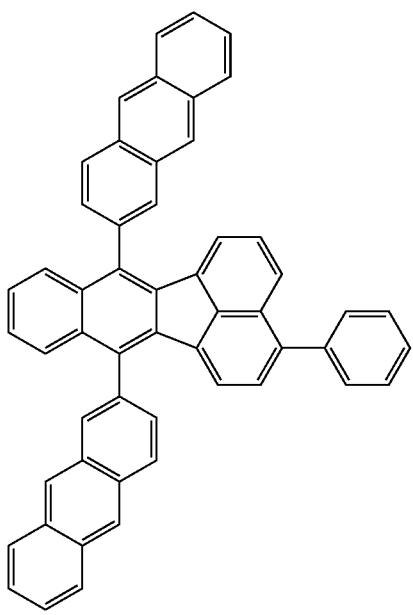
(1-024)
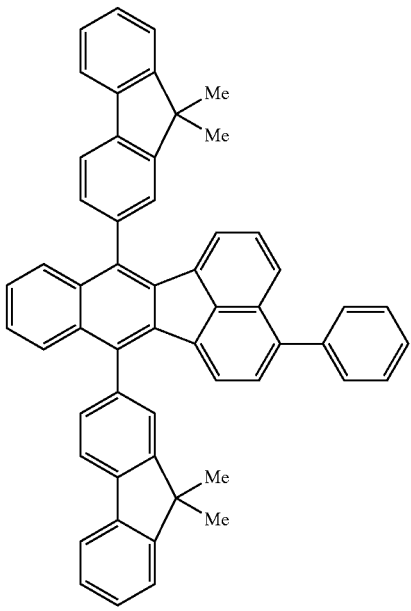
(1-025)
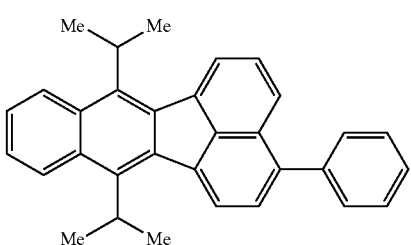
(1-023)
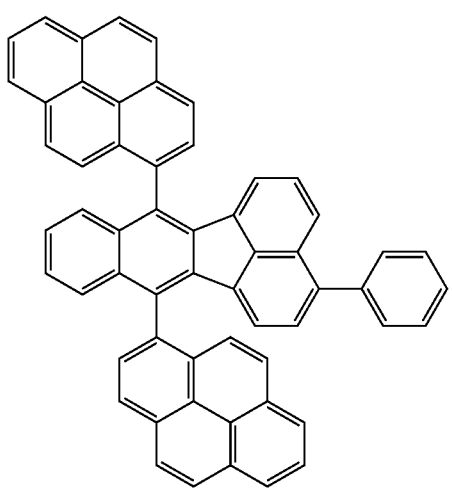
(1-026)
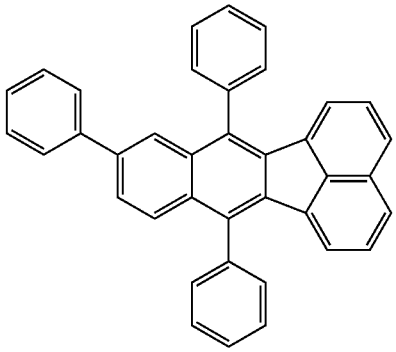

(1-027)
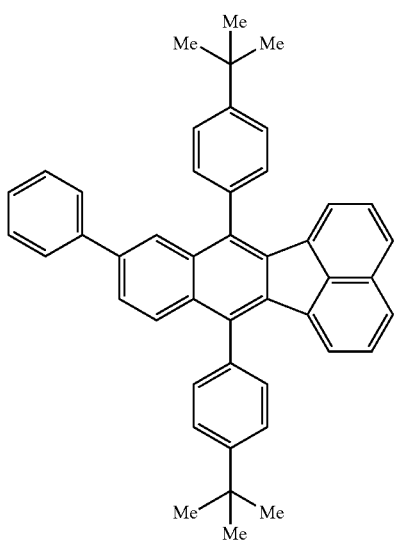
(1-028)
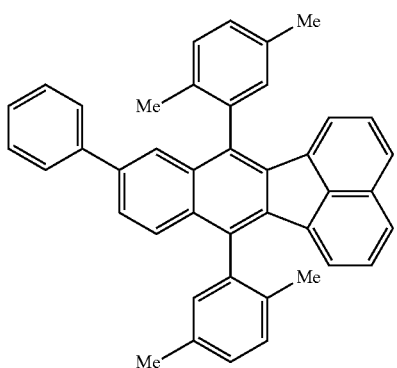
(1-029)
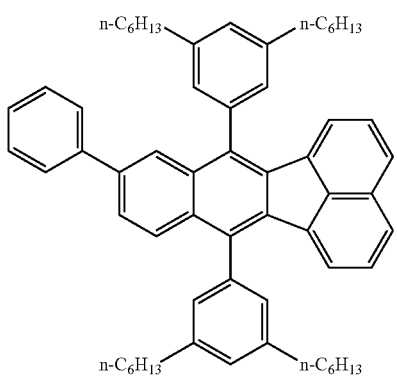
(1-030)
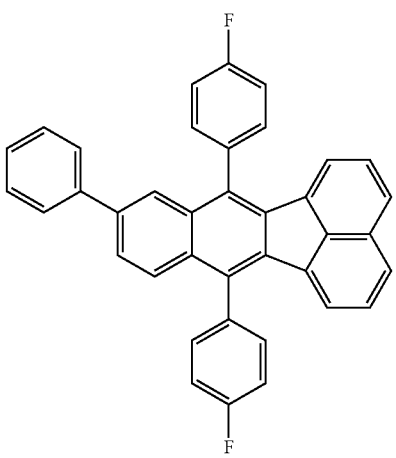
(1-031)
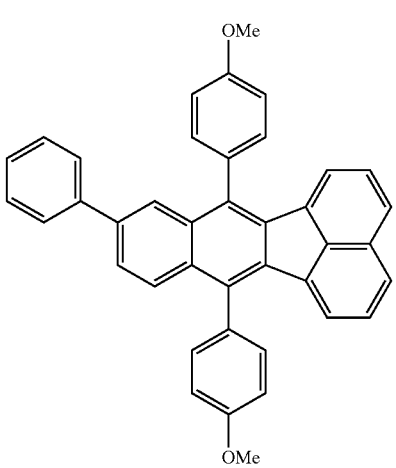
(1-032)
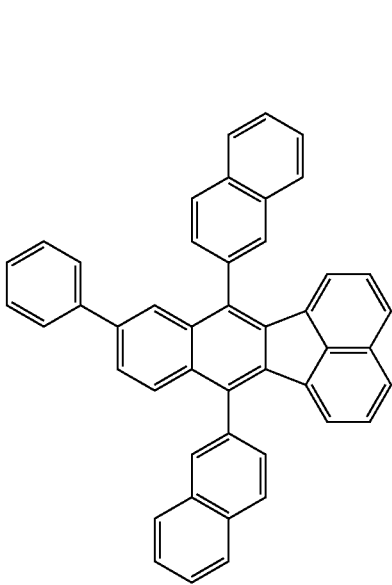

(1-033)
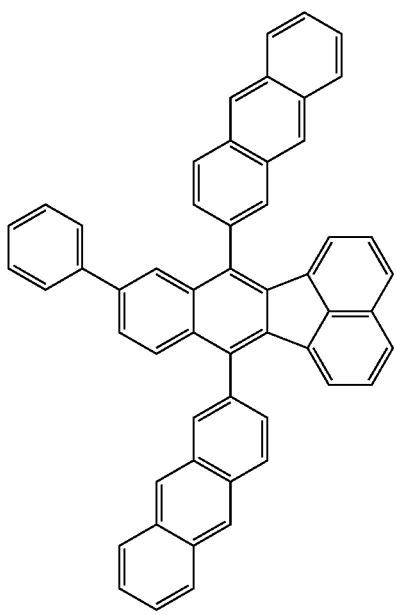
(1-034)
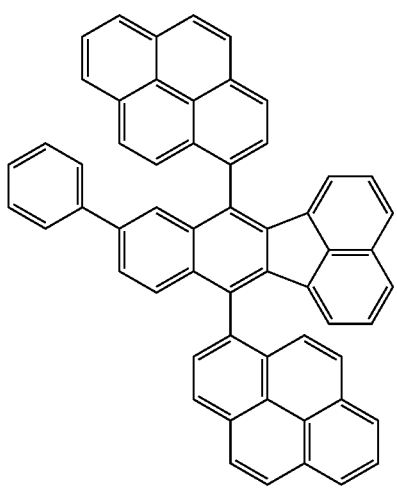
(1-035)
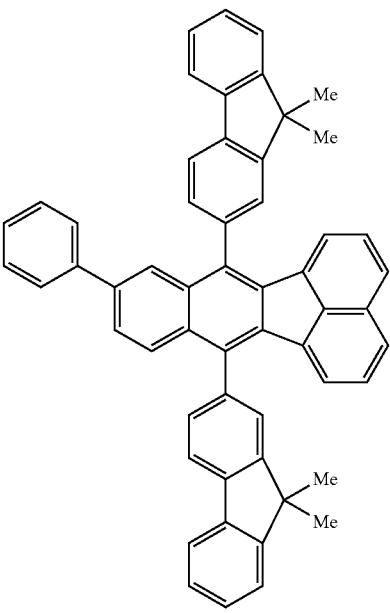
(1-036)
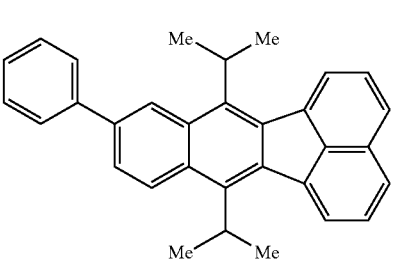
(1-037)
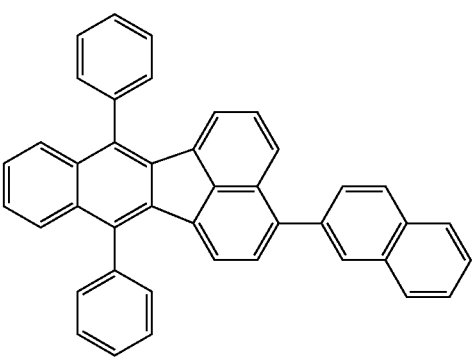

-continued
(1-038)
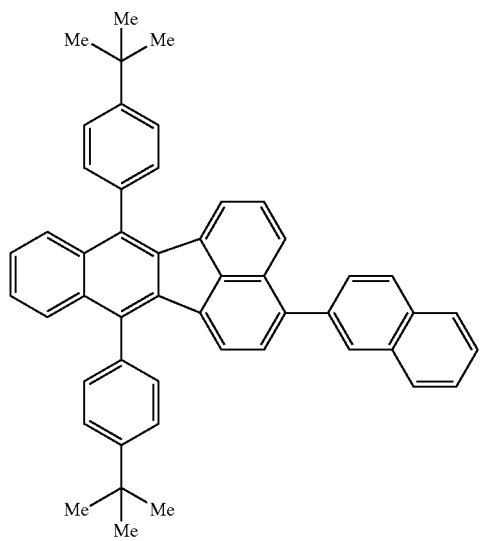
(1-039)
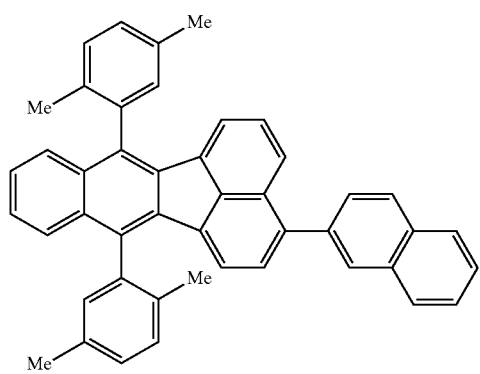
(1-040)
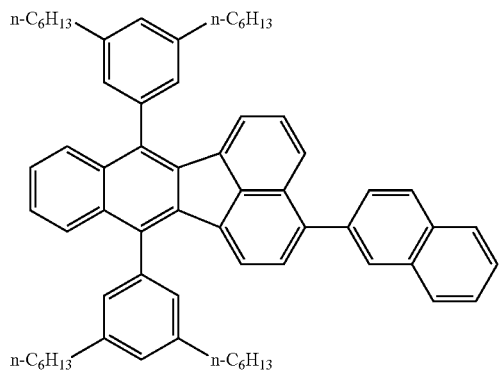
-continued
(1-041)
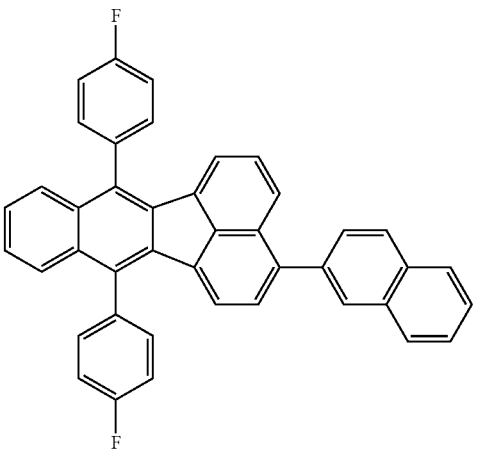
(1-042)
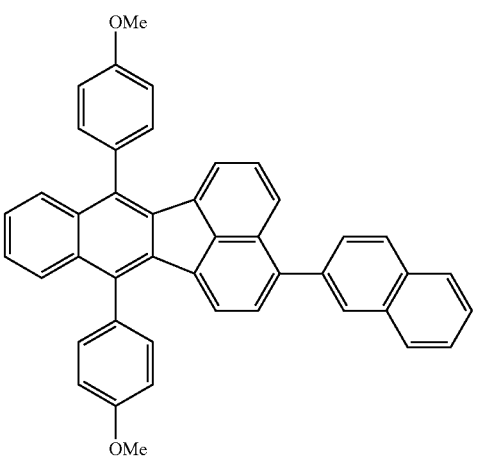
(1-043)
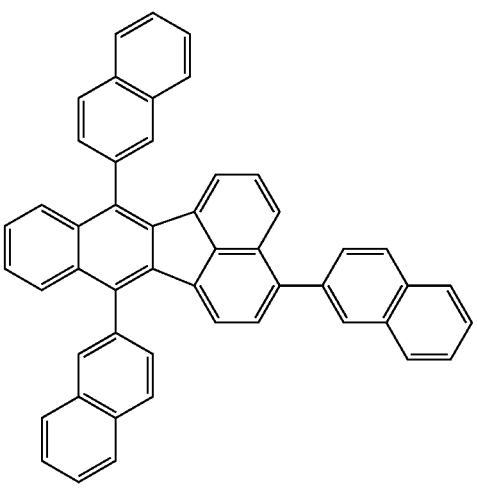

(1-044)
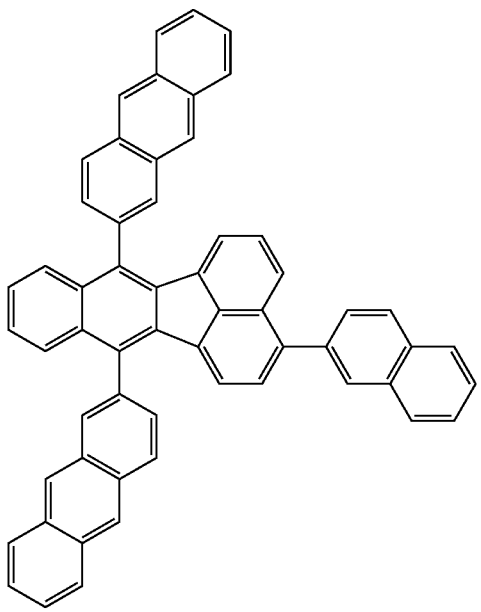
(1-045)
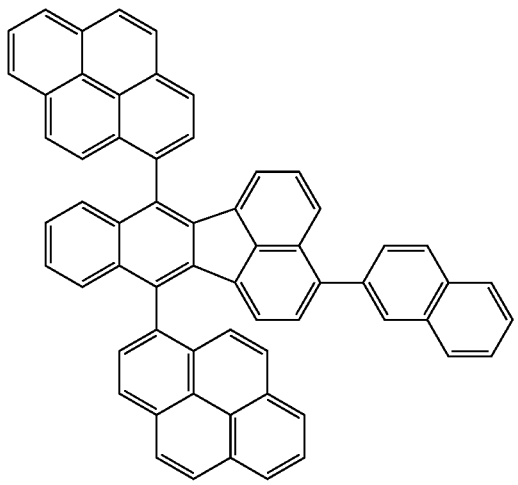
(1-046)
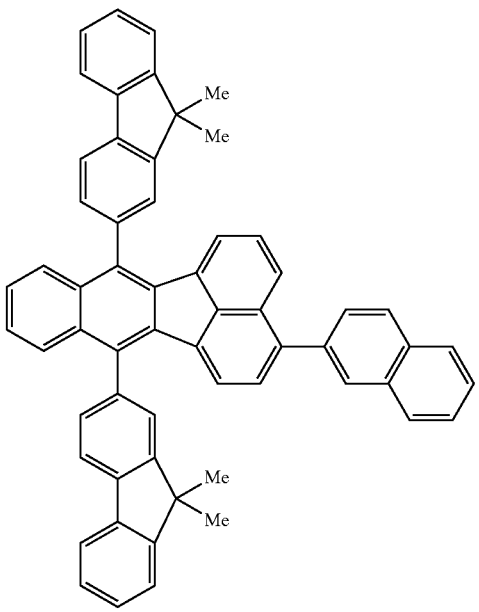
(1-047)
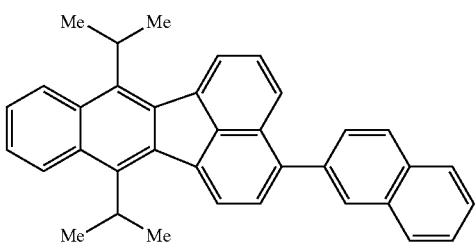
(1-048)
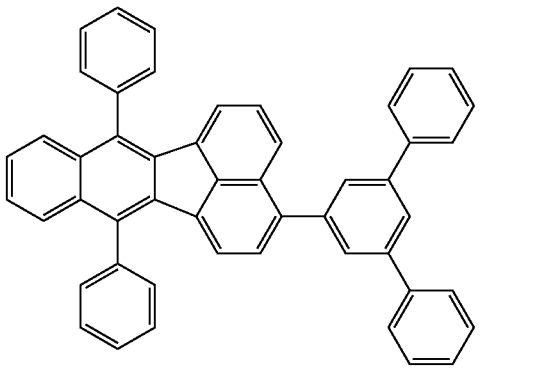

(1-049)
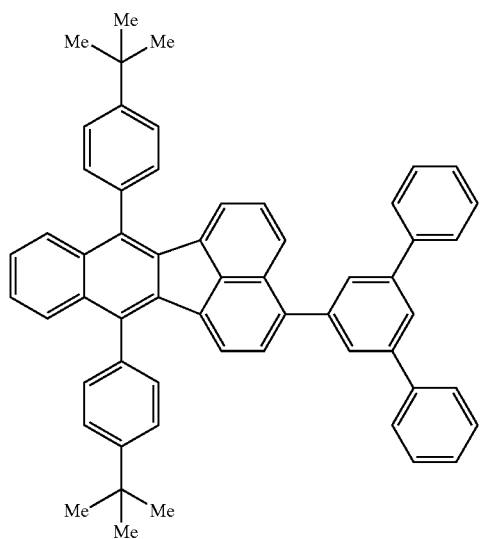
(1-052)
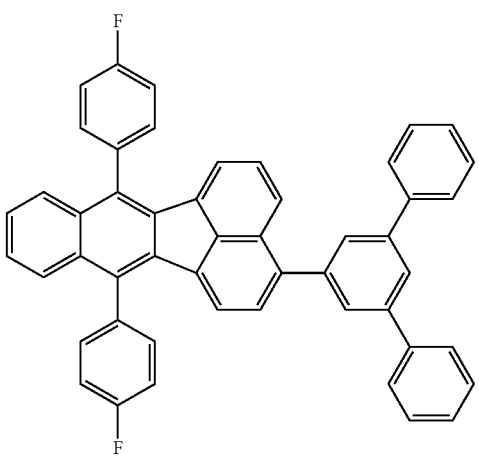
(1-050)
(1-053)
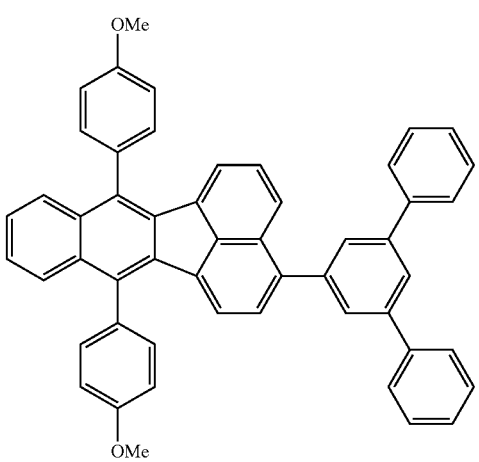
(1-051)
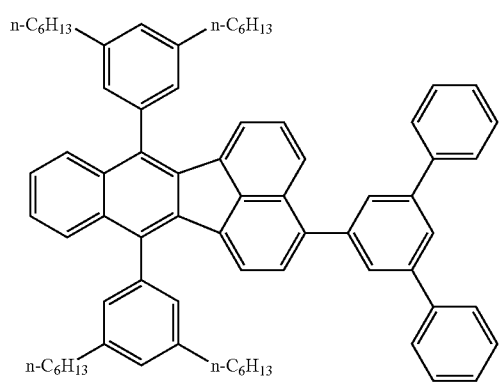
(1-054)
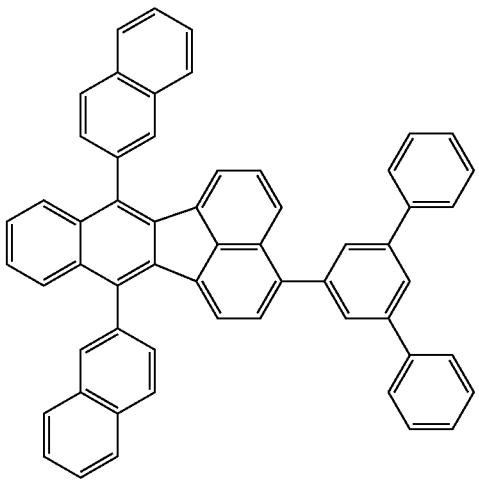

-continued
(1-055)
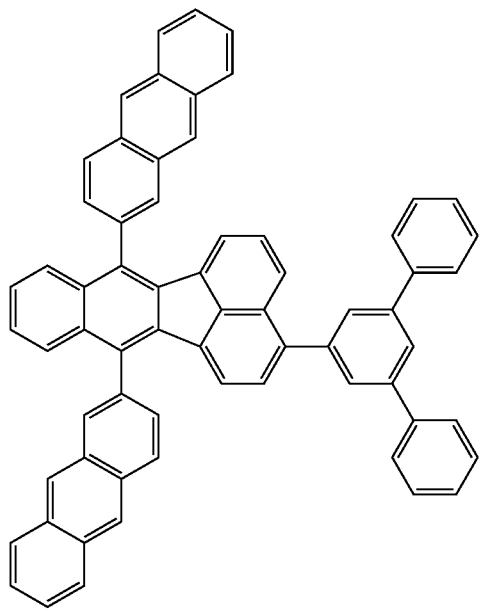
(1-056)
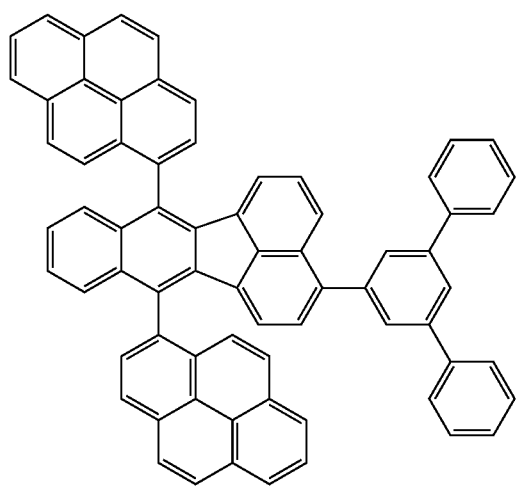
(1-057)
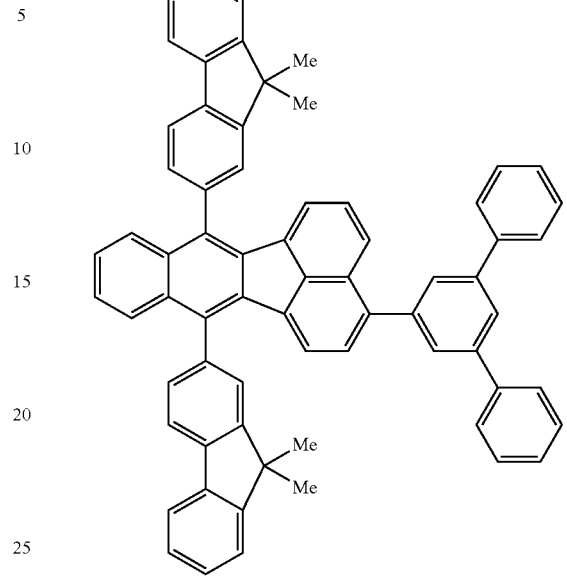
(1-058)
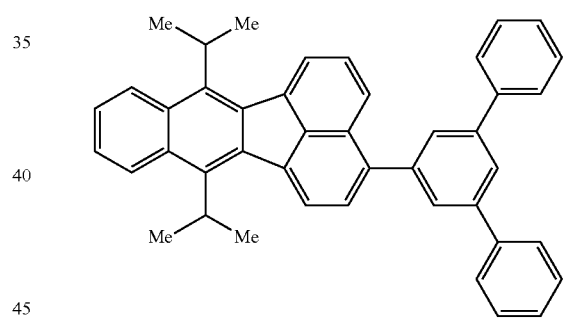
(1-059)
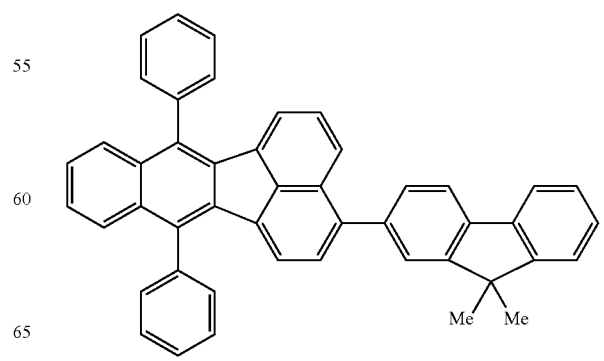

(1-060)

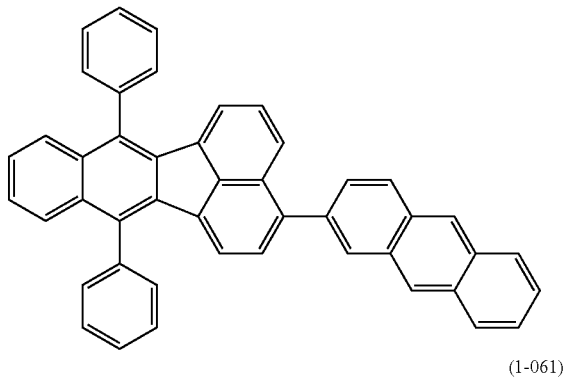

(1-061)

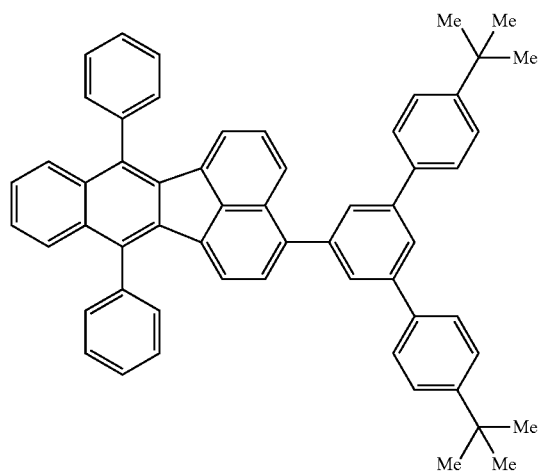

In the above-described formula (1), Ar¹ represents an unsubstituted or substituted aromatic hydrocarbon group or an unsubstituted or substituted aromatic heterocyclic group. The substituent includes an alkyl group, an aryl group, a monovalent aromatic heterocyclic group, a group represented by —O—R$^4$, or the like.

The aromatic hydrocarbon group has a carbon atom number of usually 6 to 60, preferably 6 to 48, more preferably 6 to 20, further preferably 6 to 14. The aromatic hydrocarbon group is a (2+aa)-valent aromatic hydrocarbon group, preferably a 3- or 4-valent aromatic hydrocarbon group, more preferably a 3-valent aromatic hydrocarbon group.

The aromatic heterocyclic group has a carbon atom number of usually 3 to 60, preferably 3 to 20. The aromatic heterocyclic group is a (2+aa)-valent aromatic heterocyclic group, more preferably a 3- or 4-valent aromatic heterocyclic group, further preferably a 3-valent aromatic heterocyclic group.

In the above-described formula (1), Ar¹ is preferably an unsubstituted or substituted aromatic hydrocarbon group, more preferably a 3- or 4-valent aromatic hydrocarbon group, further preferably a 3-valent aromatic hydrocarbon group, since light emission efficiency and durability thereof are excellent. "n-Valent aromatic hydrocarbon group" means an atomic group obtained by removing from an aromatic hydrocarbon n hydrogen atoms among hydrogen atoms directly linked to its aromatic ring, and includes groups having a condensed ring structure.

The aromatic hydrocarbon includes benzene, naphthalene, anthracene, 1-tetracene, pyrene, perylene, fluorene, phenanthrene, chrysene, coronene and the like.

As the constitutional unit represented by the above-described formula (1), constitutional units represented by the following formula (4) are preferable since light emission efficiency and durability thereof are excellent and synthesis of a polymer compound becomes easy.

(4)

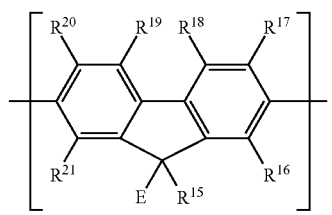

[in the formula (4), $R^{15}$ represents a hydrogen atom, an alkyl group, an aryl group, a monovalent aromatic heterocyclic group, a group represented by —O—R$^4$, or a group represented by E, and these groups may have a substituent. $R^{16}$, $R^{17}$, $R^{18}$, $R^{19}$, $R^{20}$ and $R^{21}$ each independently represent a hydrogen atom, an alkyl group, an aryl group, a monovalent aromatic heterocyclic group or a group represented by —O—R$^4$, and these groups may have a substituent. $R^4$ is defined above. When there are a plurality of $R^4$s, these may be the same or different. $R^{17}$ and $R^{18}$, and $R^{19}$ and $R^{20}$ may each be linked to each other to form a ring. E is defined above.]

In the above-described formula (4), it is preferable that $R^{15}$ represents an alkyl group, an aryl group or a monovalent aromatic heterocyclic group.

In the above-described formula (4), it is preferable that $R^{16}$, $R^{17}$, $R^{20}$ and $R^{21}$ represent a hydrogen atom, it is more preferable that $R^{16}$, $R^{17}$, $R^{18}$, $R^{19}$, $R^{20}$ and $R^{21}$ represent a hydrogen atom.

In the above-described formula (4), it is preferable that $R^{15}$ represents an alkyl group, an aryl group or a monovalent aromatic heterocyclic group and $R^{16}$, $R^{17}$, $R^{20}$ and $R^{21}$ represent a hydrogen atom, it is more preferable that $R^{15}$ represents an alkyl group, an aryl group or a monovalent aromatic heterocyclic group and $R^{16}$, $R^{17}$, $R^{18}$, $R^{19}$, $R^{20}$ and $R^{21}$ represent a hydrogen atom, since light emission efficiency and durability thereof are excellent.

As the constitutional unit represented by the above-described formula (1), constitutional units represented by the following formulae (1-101) to (1-114) are preferable since light emission efficiency and durability thereof are excellent.

(1-101)

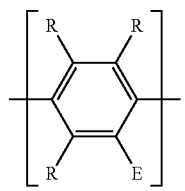

(1-102)

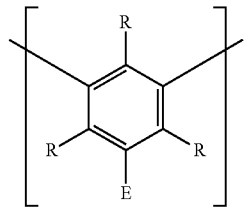

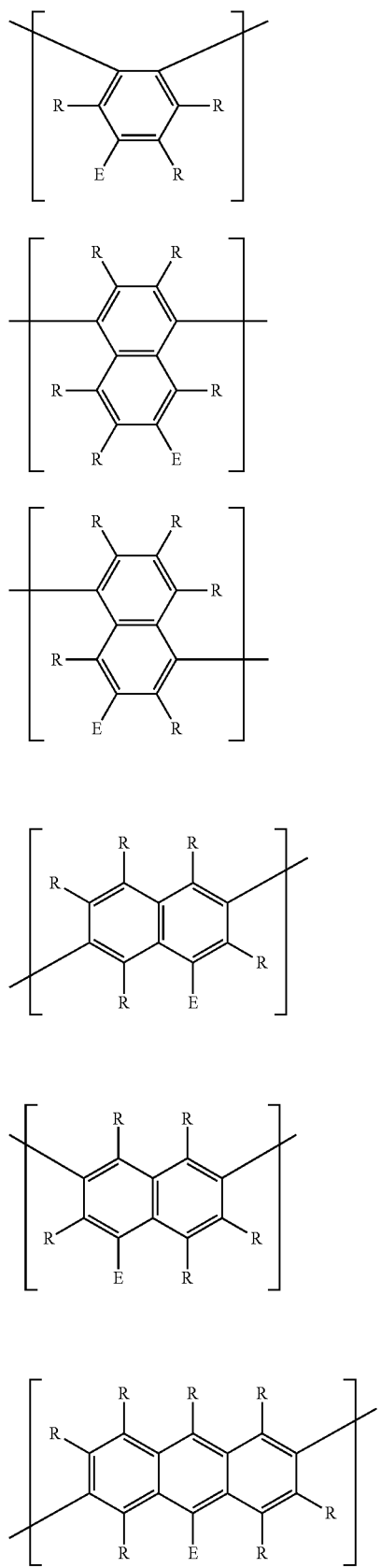
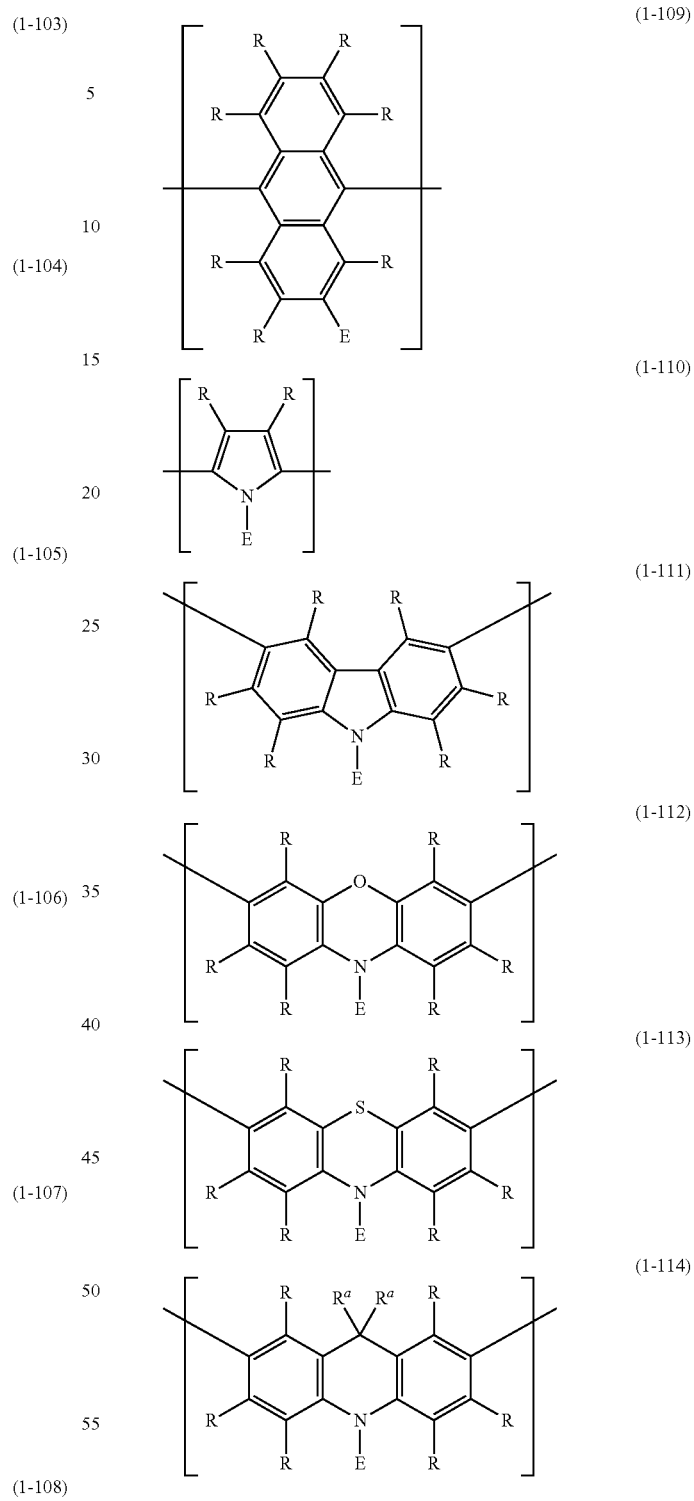

[in the formula, R represents a hydrogen atom, an alkyl group, an aryl group, a monovalent aromatic heterocyclic group, a group represented by —O—$R^A$, a group represented by —S—$R^A$, a group represented by —C(=O)—$R^A$, a group represented by —C(=O)—O—$R^A$, a cyano group or a fluorine atom. The alkyl group, the aryl group, the monovalent aromatic heterocyclic group, the group represented by —O—$R^A$, the group represented by —S—$R^A$, the group represented by —C(=O)—$R^A$ and the group represented by —C(=O)—O—$R^A$ may have a substituent. $R^a$ represents an alkyl group, an aryl group or a monovalent aromatic heterocyclic group, and these groups may have a substituent. E is defined above. A plurality of Rs may be the same or different. A plurality of $R^a$s may be the same or different. $R^A$ is defined above.]

[Second Constitutional Unit]

It is preferable that the polymer compound according to the present invention contains a constitutional unit represented by the following formula (5) (hereinafter, referred to as "second constitutional unit"), since light emission efficiency and durability thereof are excellent.

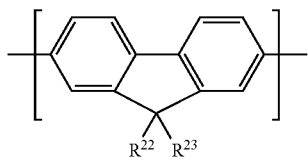 (5)

[in the formula (5), $R^{22}$ and $R^{23}$ each independently represent an alkyl group, an aryl group or a monovalent aromatic heterocyclic group, and these groups may have a substituent. $R^{22}$ and $R^{23}$ are different from the group represented by E.]

In the above-described formula (5), the alkyl group represented by $R^{22}$ and $R^{23}$ includes a methyl group, an ethyl group, a propyl group, an isopropyl group, a butyl group, a sec-butyl group, an isobutyl group, a pentyl group, a 2-methylbutyl group, an isoamyl group, a hexyl group, a heptyl group, an octyl group, a 2-ethylhexyl group, a nonyl group, a decyl group, a 3,7-dimethyloctyl group, a dodecyl group and the like. These groups may have a substituent.

In the above-described formula (5), the aryl group represented by $R^{22}$ and $R^{23}$ includes an unsubstituted or substituted phenyl group, an unsubstituted or substituted 1-naphthyl group, an unsubstituted or substituted 2-naphthyl group and the like.

In the above-described formula (5), the monovalent aromatic heterocyclic groups represented by $R^{22}$ and $R^{23}$ are the same as explained and exemplified for the above-described monovalent aromatic heterocyclic group represented by $R^1$.

In the above-described formula (5), $R^{22}$ and $R^{23}$ represent preferably a substituted or unsubstituted aryl group, or a substituted or unsubstituted alkyl group, more preferably an unsubstituted aryl group; an aryl group substituted by an alkyl group, an alkoxy group, an aryl group or a substituted amino group; an unsubstituted alkyl group; an alkyl group substituted by an alkyl group, an alkoxy group, an aryl group or a substituted amino group, further preferably a 4-tolyl group, a 4-butylphenyl group, a 4-tert-butylphenyl group, a 4-hexylphenyl group, a 4-octylphenyl group, a 4-(2-ethylhexyl)phenyl group, a 4-(3,7-dimethyloctyl)phenyl group, a 3-tolyl group, a 3-butylphenyl group, a 3-tert-butylphenyl group, a 3-hexylphenyl group, a 3-octylphenyl group, a 3-(2-ethylhexyl)phenyl group, a 3-(3,7-dimethyloctyl)phenyl group, a 3,5-dimethylphenyl group, a 3,5-di-(tert-butyl)phenyl group, a 3,5-dihexylphenyl group, a 3,5-dioctylphenyl group, a 3,4-dihexylphenyl group, a 3,4-dioctylphenyl group, a 4-hexyloxyphenyl group, a 4-octyloxyphenyl group, a 4-(2-ethoxy)ethoxyphenyl group, a 4-(4'-tert-butylbiphenylyl) group, a 9,9-dihexylfluoren-2-yl group, a 9,9-dioctylfluoren-2-yl group, a pentyl group, a neopentyl group, a hexyl group, a heptyl group, a 2-ethylhexyl group, an octyl group, a 3,7-dimethyloctyl group, a nonyl group, a decyl group, a dodecyl group, a 2-ethyldecyl group or a 4-butyloctyl group, since the heat resistance and the solubility of the polymer compound according to the present invention are excellent.

These second constitutional units may be contained singly or in combination in a polymer compound.

[Third Constitutional Unit]

It is preferable that the polymer compound according to the present invention contains a constitutional unit represented by the following formula (6) (hereinafter, referred to as "third constitutional unit"):

 (6)

[in the formula (6), $Ar^2$ represents an arylene group, a divalent aromatic heterocyclic group or a divalent group formed by linking two or more identical or different groups selected from the group consisting of arylene groups and divalent aromatic heterocyclic groups. $Ar^2$ may have at least one substituent selected from the group consisting of an alkyl group, an aryl group, a monovalent aromatic heterocyclic group, a group represented by —O—$R^A$, a group represented by —S—$R^A$, a group represented by —C(=O)—$R^A$, a group represented by —C(=O)—O—$R^A$, a group represented by —N($R^A$)$_2$, a cyano group and a fluorine atom. $R^A$ is defined above. When there are a plurality of $R^A$s, these may be the same or different. The constitutional unit represented by the formula (6) is different from the constitutional unit represented by the above-described formulae (1) and (5).], since durability thereof is excellent.

In the above-described formula (6), the group represented by —S—$R^A$ may be any of linear, branched or cyclic, and includes alkylthio groups having a carbon atom number of usually 1 to 20 and arylthio groups having a carbon atom number of usually 6 to 60.

In the above-described formula (6), the group represented by the above-described —C(=O)—$R^A$ may be any of linear, branched or cyclic, and includes alkylcarbonyl groups having a carbon atom number of usually 1 to 20 and arylcarbonyl groups having a carbon atom number of usually 6 to 60.

In the above-described formula (6), the group represented by the above-described —C(=O)—O—$R^A$ may be any of linear, branched or cyclic, and includes alkyloxycarbonyl groups having a carbon atom number of usually 1 to 20 and aryloxycarbonyl groups having a carbon atom number of usually 6 to 60.

In the above-described formula (6), the group represented by the above-described —N($R^A$)$_2$ includes amino groups substituted by two groups selected from the group consisting of alkyl groups having a carbon atom number of usually 1 to 20 and aryl groups having a carbon atom number of usually 6 to 60.

In the above-described formula (6), the arylene group represented by $Ar^2$ has a carbon atom number of usually 6 to 60, preferably 6 to 48, more preferably 6 to 30, further preferably 6 to 14. This carbon atom number does not include the carbon atom number of a substituent. The above-described arylene group includes phenylene groups such as a 1,4-phenylene group (the formula (6-001)), a 1,3-phenylene group (the formula (6-002)), a 1,2-phenylene group (the formula (6-003)) and the like; naphthalenediyl groups such as a naphthalene-1,4-diyl group (the formula (6-004)), a naphthalene-1,5-diyl group (the formula (6-005)), a naphthalene-2,6-diyl group (the formula (6-006)), a naphthalene-2,7-diyl group (the formula (6-007)) and the like; dihydrophenanthrenediyl groups such as a 4,5-dihydrophenanthrene-2,7-diyl group (the formula (6-008)) and the like; a fluorene-3,6-diyl group (the formula (6-009)); benzofluorenediyl groups represented by the formulae (6-010) to (6-012); anthracenediyl groups such as an anthracene-2,6-diyl group (the formula (6-013)), an anthracene-9,10-diyl group (the formula (6-014)) and the like; etc. A hydrogen atom in these arylene groups may be substituted by an alkyl group, an aryl group, a monovalent aromatic heterocyclic group, a group represented by —O—$R^A$, a group represented by —S—$R^A$, a group represented by —C(=O)—$R^A$, a group represented by —C(=O)—O—$R^A$, a group represented by —N($R^A$)$_2$, a cyano group or a fluorine atom.

(6-001)
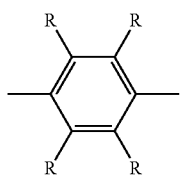

(6-002)
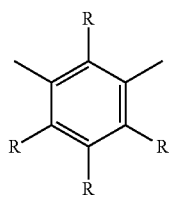

(6-003)
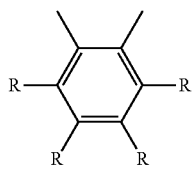

(6-004)
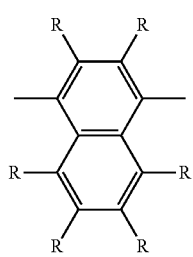

(6-005)
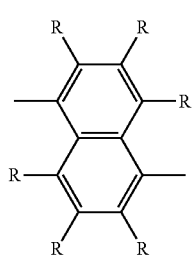

(6-006)
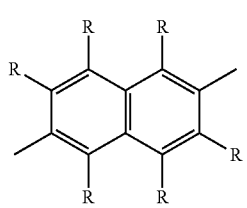

(6-007)
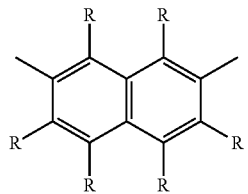

(6-008)
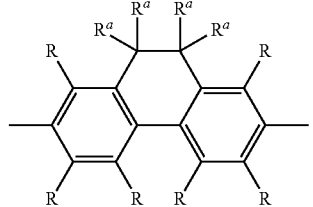

(6-009)
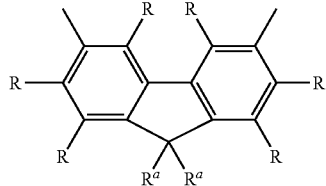

(6-010)
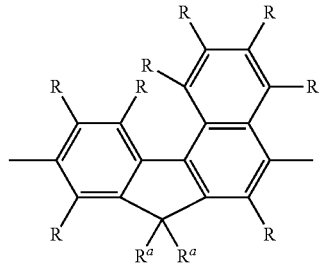

(6-011)
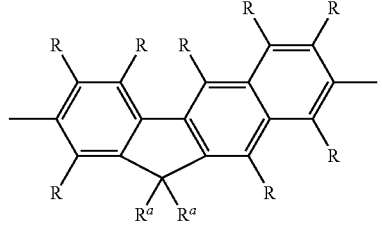

(6-012)
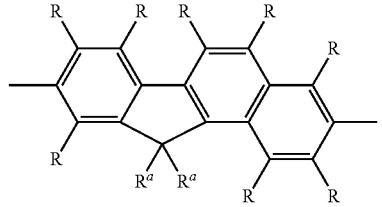

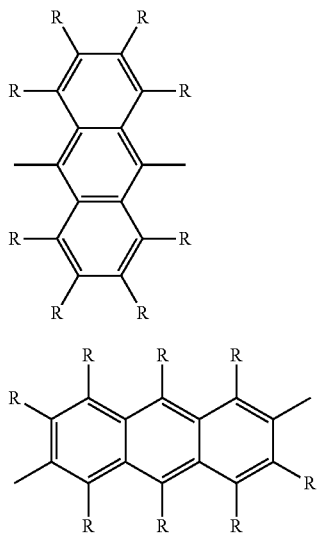
(6-013)

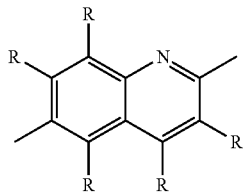
(6-101)

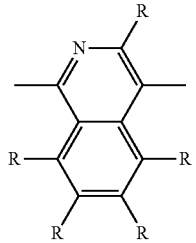
(6-102)

(6-014)

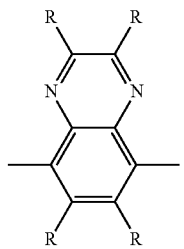
(6-103)

[in the formulae (6-001) to (6-014), R and $R^a$ each independently represent the same meaning as described above.]

In the above-described formula (6), the divalent aromatic heterocyclic group represented by $Ar^2$ is preferably a divalent condensed aromatic heterocyclic group, since the stability of the polymer compound according to the present invention is excellent. This divalent condensed aromatic heterocyclic group has a carbon atom number of usually 8 to 60, preferably 8 to 20. This carbon atom number does not include the carbon atom number of a substituent. The above-described divalent condensed aromatic heterocyclic group includes quinolinediyl groups such as a quinoline-2,6-diyl group (the formula (6-101)) and the like; isoquinolinediyl groups such as an isoquinoline-1,4-diyl group (the formula (6-102)) and the like; quinoxalinediyl groups such as a quinoxaline-5,8-diyl group (the formula (6-103)) and the like; carbazolediyl groups such as a carbazole-3,6-diyl group (the formula (6-104)), a carbazole-2,7-diyl group (the formula (6-105)) and the like; dibenzofurandiyl groups such as a dibenzofuran-4,7-diyl group (the formula (6-106)), a dibenzofuran-3,8-diyl group (the formula (6-107)) and the like; dibenzothiophenediyl groups such as a dibenzothiophene-4,7-diyl group (the formula (6-108)), a dibenzothiophene-3,8-diyl group (the formula (6-109)) and the like; dibenzosilolediyl groups such as a dibenzosilole-4,7-diyl group (the formula (6-110)), a dibenzosilole-3,8-diyl group (the formula (6-111)) and the like; phenoxazinediyl groups such as a phenoxazine-3,7-diyl group (the formula (6-112)), a phenoxazine-2,8-diyl group (the formula (6-113)) and the like; phenothiazinediyl groups such as a phenothiazine-3,7-diyl group (the formula (6-114)), a phenothiazine-2,8-diyl group (the formula (6-115)) and the like; dihydroacridinediyl groups such as a dihydroacridine-2,7-diyl group (the formula (6-116)) and the like; a divalent group represented by the formula (6-117); etc. A hydrogen atom in these divalent condensed aromatic heterocyclic groups may be substituted by an alkyl group, an aryl group, a monovalent aromatic heterocyclic group, a group represented by —O—$R^A$, a group represented by —S—$R^A$, a group represented by —C(=O)—$R^A$, a group represented by —C(=O)—O—$R^A$, a cyano group or a fluorine atom.

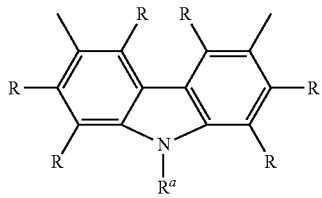
(6-104)

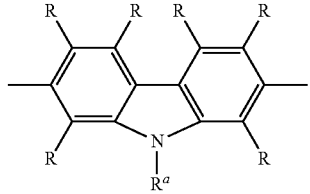
(6-105)

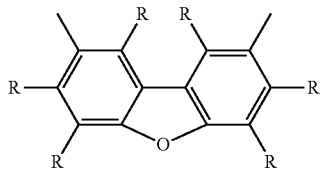
(6-106)

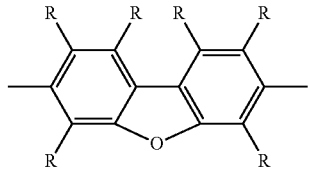
(6-107)

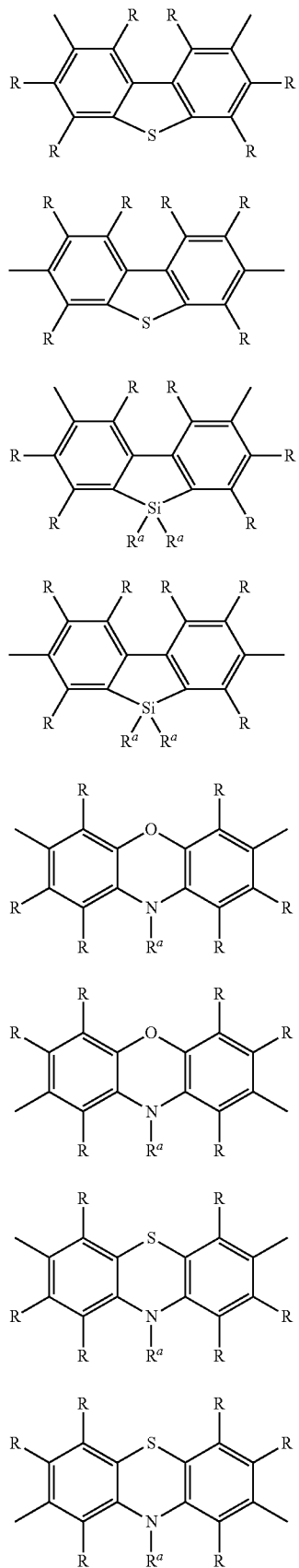

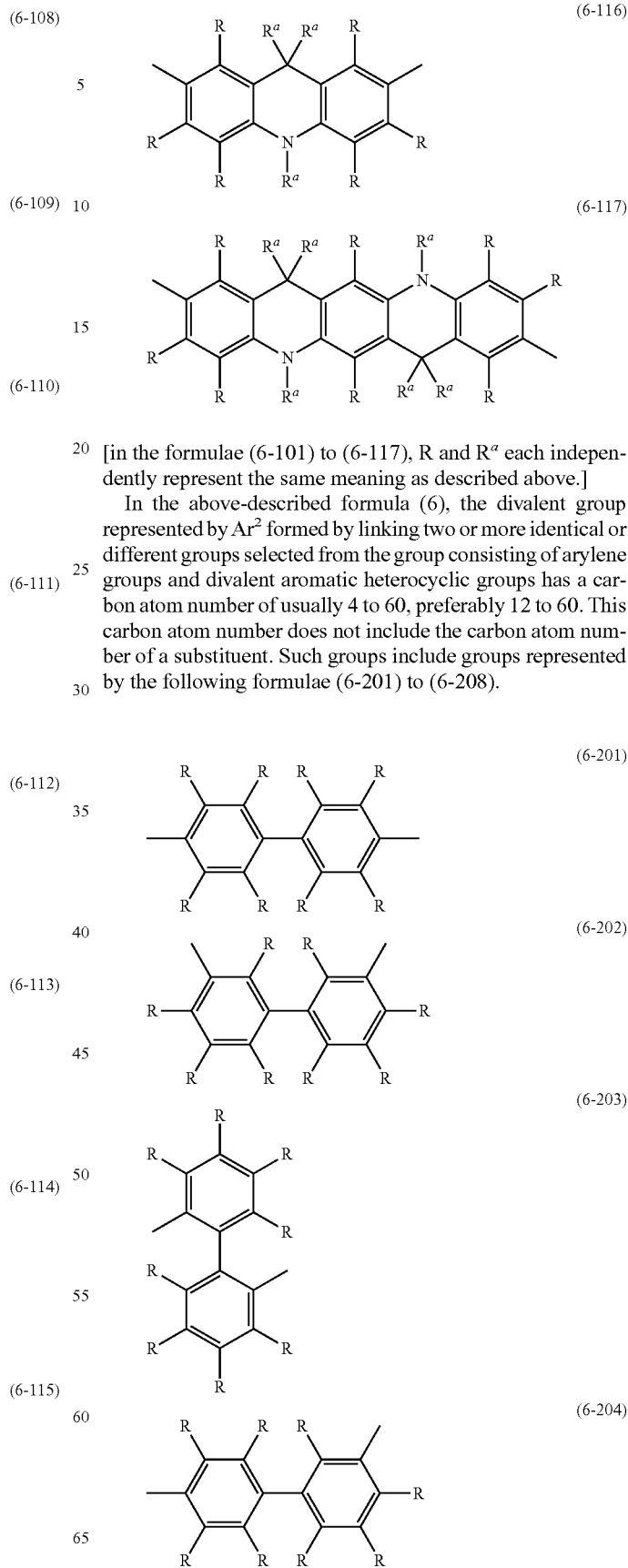

[in the formulae (6-101) to (6-117), R and $R^a$ each independently represent the same meaning as described above.]

In the above-described formula (6), the divalent group represented by $Ar^2$ formed by linking two or more identical or different groups selected from the group consisting of arylene groups and divalent aromatic heterocyclic groups has a carbon atom number of usually 4 to 60, preferably 12 to 60. This carbon atom number does not include the carbon atom number of a substituent. Such groups include groups represented by the following formulae (6-201) to (6-208).

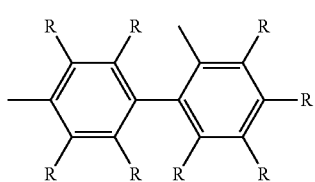
(6-205)

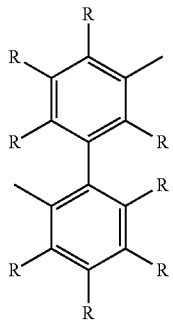
(6-206)

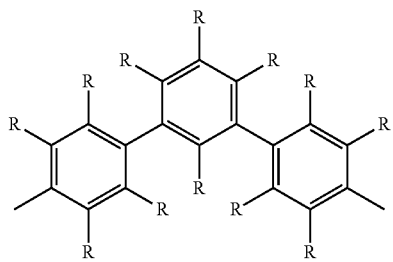
(6-207)

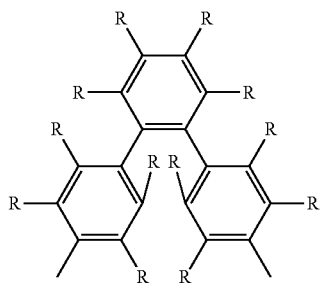
(6-208)

[in the formulae (6-201) to (6-208), R is defined above.]

In the above-described formula (6), $Ar^2$ represents preferably a 1,4-phenylene group (the formula (6-001)), a 1,3-phenylene group (the formula (6-002)), a 9,10-dihydrophenanthrene-2,7-diyl group (the formula (6-008)), a fluorene-3,6-diyl group (the formula (6-009)), a benzofluorenediyl group represented by the formulae (6-010) to (6-012), an anthracene-2,6-diyl group (the formula (6-013)), an anthracene-9,10-diyl group (the formula (6-014)), a carbazole-3,6-diyl group (the formula (6-104)), a carbazole-2,7-diyl group (the formula (6-105)), a dibenzofuran-4,7-diyl group (the formula (6-106)), a dibenzofuran-3,8-diyl group (the formula (6-107)), a dibenzothiophene-4,7-diyl group (the formula (6-108)), a dibenzothiophene-3,8-diyl group (the formula (6-109)), a dibenzosilole-4,7-diyl group (the formula (6-110)), a dibenzosilole-3,8-diyl group (the formula (6-111)), a phenoxazine-3,7-diyl group (the formula (6-112)), a phenothiazine-3,7-diyl group (the formula (6-114)), a dihydroacridine-2,7-diyl group (the formula (6-116)), a divalent group represented by the formula (6-117), a divalent group represented by the formula (6-201), a divalent group represented by the formula (6-202), or a divalent group represented by the formula (6-207), and it is more preferable that R represents a hydrogen atom, an alkyl group, an aryl group or a monovalent aromatic heterocyclic group (especially, a hydrogen atom or an alkyl group) and $R^a$ represents an alkyl group or an aryl group, in these groups, since the chemical stability of the polymer compound according to the present invention and the light emission efficiency of a light emitting device using this polymer compound are excellent.

These third constitutional units may be contained singly or in combination in the polymer compound.

[Fourth Constitutional Unit]

It is preferable that the polymer compound according to the present invention contains a constitutional unit represented by the following formula (7) (hereinafter, referred to as "fourth constitutional unit"):

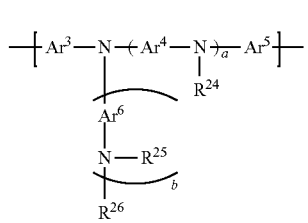
(7)

[in the formula (7), $Ar^3$, $Ar^4$, $Ar^5$ and $Ar^6$ each independently represent an unsubstituted or substituted arylene group, an unsubstituted or substituted divalent aromatic heterocyclic group or a divalent group formed by linking two or more identical or different groups selected from the group consisting of arylene groups and divalent aromatic heterocyclic groups. $Ar^3$ and $Ar^4$, $Ar^3$ and $Ar^6$, and $Ar^4$ and $Ar^5$ may each be linked via a single bond or linked via a group represented by —O—, —S—, —C(=O)—, —C(=O)—O—, —N($R^A$)—, —C(=O)—N($R^A$)— or —C($R^A$)$_2$— to form a ring. $R^A$ is defined above. When there are a plurality of $R^A$s, these may be the same or different. $R^{24}$, $R^{25}$ and $R^{26}$ each independently represent a hydrogen atom, an alkyl group, an aryl group, a monovalent heterocyclic group or an arylalkyl group, and these groups may have a substituent. a represents an integer of 0 to 3, and b represents 0 or 1.],
since the light emission efficiency and the durability of a light emitting device obtained by using this polymer compound are excellent.

"$Ar^3$ and $Ar^4$, $Ar^3$ and $Ar^6$, and $Ar^4$ and $Ar^5$ are each linked via a single bond" denotes that "$Ar^3$ and $Ar^4$, $Ar^3$ and $Ar^6$, and $Ar^4$ and $Ar^5$ are each directly linked". In the above-described formula (7), the arylene group represented by $Ar^3$, $Ar^4$, $Ar^5$ and $Ar^6$ includes groups represented by the following formula (6-301) and the same groups as the groups explained and exemplified as the above-described arylene group represented by $Ar^2$.

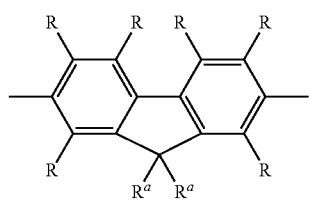
(6-301)

[in the formula (6-301), R and $R^a$ each independently represent the same meaning as described above.]

In the above-described formula (7), the divalent aromatic heterocyclic groups represented by $Ar^3$, $Ar^4$, $Ar^5$ and $Ar^6$ are the same as explained and exemplified as the above-described divalent aromatic heterocyclic group represented by $Ar^2$.

In the above-described formula (7), the divalent group represented by $Ar^3$, $Ar^4$, $Ar^5$ and $Ar^6$ formed by linking two or more identical or different groups selected from the group consisting of arylene groups and divalent aromatic heterocyclic groups is defined above, and includes also groups combined with the group represented by the above-described formula (6-301).

In the above-described formula (7), the group represented by $Ar^3$, $Ar^4$, $Ar^5$ and $Ar^6$ is preferably an unsubstituted or substituted arylene group, since the stability of the polymer compound of the present invention is excellent and the light emission efficiency of a light emitting device using this polymer compound is excellent.

In the above-described formula (7), $R^{24}$, $R^{25}$ and $R^{26}$ represent preferably an alkyl group, an aryl group or a monovalent aromatic heterocyclic group, more preferably an aryl group, since the stability of the polymer compound according to the present invention and the light emission efficiency of a light emitting device using this polymer compound are excellent.

In the above-described formula (7), when $Ar^3$ and $Ar^4$, $Ar^3$ and $Ar^6$, and $Ar^4$ and $Ar^5$ are each linked to each other to form a ring, this ring is usually a 5- to 7-membered ring.

The constitutional unit represented by the above-described formula (7) includes preferably constitutional units represented by the following formulae (7-001) to (7-005).

(7-001)

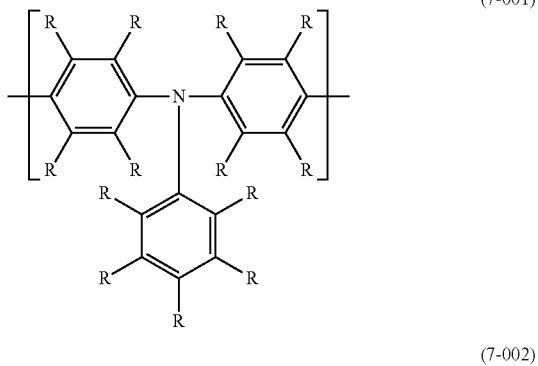

(7-002)

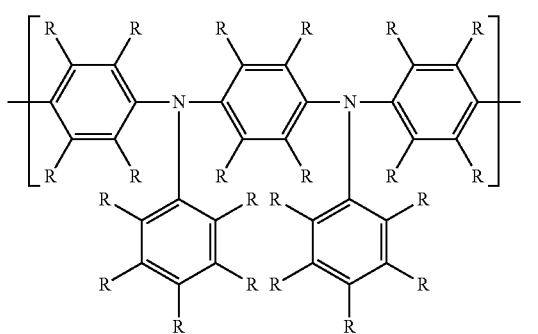

(7-003)

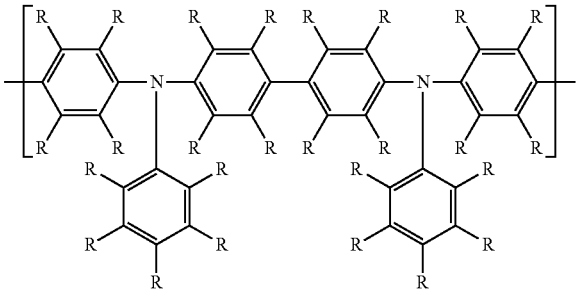

(7-004)

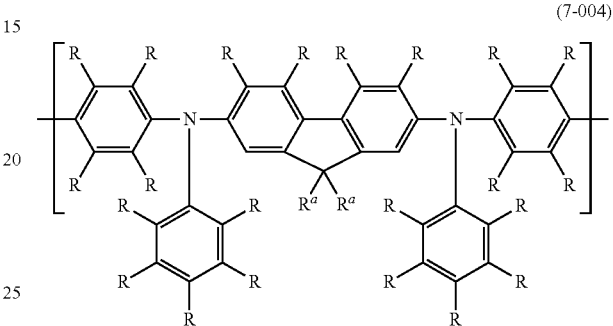

(7-005)

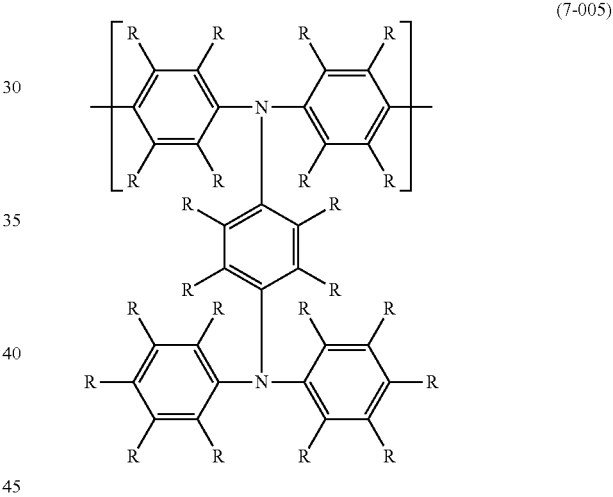

[in the formulae (7-001) to (7-005), R and $R^a$ each independently represent the same meaning as described above.]

The constitutional unit represented by the above-described formula (7) includes preferably constitutional units represented by the above-described formulae (7-001) to (7-005) in which R represents a hydrogen atom, an alkyl group, an aryl group or a monovalent aromatic heterocyclic group (especially, a hydrogen atom or an alkyl group) and $R^a$ represents an alkyl group or an aryl group, since the stability of the polymer compound according to the present invention and the light emission efficiency of a light emitting device using this polymer compound are excellent.

These fourth constitutional units may be contained singly or in combination in the polymer compound.

As the polymer compound according to the present invention, preferable are polymer compounds comprising a first constitutional unit represented by the above-described formula (1) and a second constitutional unit represented by the above-described formula (5), from the standpoint of durability.

As the polymer compound according to the present invention, preferable are polymer compounds comprising a first constitutional unit represented by the above-described formula (1), a second constitutional unit represented by the above-described formula (5), and at least one constitutional unit selected from the group consisting of third constitutional units represented by the above-described formula (6) and fourth constitutional units represented by the above-described general formula (7), more preferable are polymer compounds comprising a first constitutional unit represented by the above-described formula (1), a second constitutional unit represented by the above-described formula (5) and a fourth constitutional unit represented by the above-described formula (7), from the standpoint of light emission efficiency and durability.

As the polymer compound according to the present invention, preferable are conjugated polymer compounds, since the light emission efficiency of a light emitting device obtained by using this polymer compound is excellent.

[Constitution of Polymer Compound According to the Present Invention]

In the polymer compound according to the present invention, the content of the above-described first constitutional unit with respect to the total content of the above-described first constitutional unit, the above-described second constitutional unit, the above-described third constitutional unit and the above-described fourth constitutional unit is preferably 0.01 to 90 mol %, more preferably 0.1 to 50 mol %, further preferably 0.1 to 20 mol %, particularly preferably 0.5 to 10 mol %, since the light emission efficiency of a light emitting device obtained by using this polymer compound is excellent.

In the polymer compound according to the present invention, the total content of the above-described first constitutional unit, the above-described second constitutional unit, the above-described third constitutional unit and the above-described fourth constitutional unit with respect to the total amount of the above-described polymer compound is preferably 80 to 100 wt %, more preferably 90 to 100 wt %, since the light emission efficiency of a light emitting device obtained by using this polymer compound is excellent.

When the polymer compound according to the present invention contains a fourth constitutional unit, the content of the fourth constitutional unit with respect to the total content of the above-described first constitutional unit, the above-described second constitutional unit, the above-described third constitutional unit and the above-described fourth constitutional unit is preferably 0.5 mol % or more, more preferably 1 mol % or more. The upper limit of the above-described content is preferably 20 mol %, more preferably 10 mol %, since light emission efficiency and durability thereof are excellent.

The polymer compound according to the present invention includes polymer compounds P1 to P20 combining a first constitutional unit, a second constitutional unit, a third constitutional unit and a fourth constitutional unit. Here, the total content of the first constitutional unit, the second constitutional unit, the third constitutional unit and the fourth constitutional unit in the polymer compounds P1 to P20 is 100 wt % with respect to the total amount of the polymer compound.

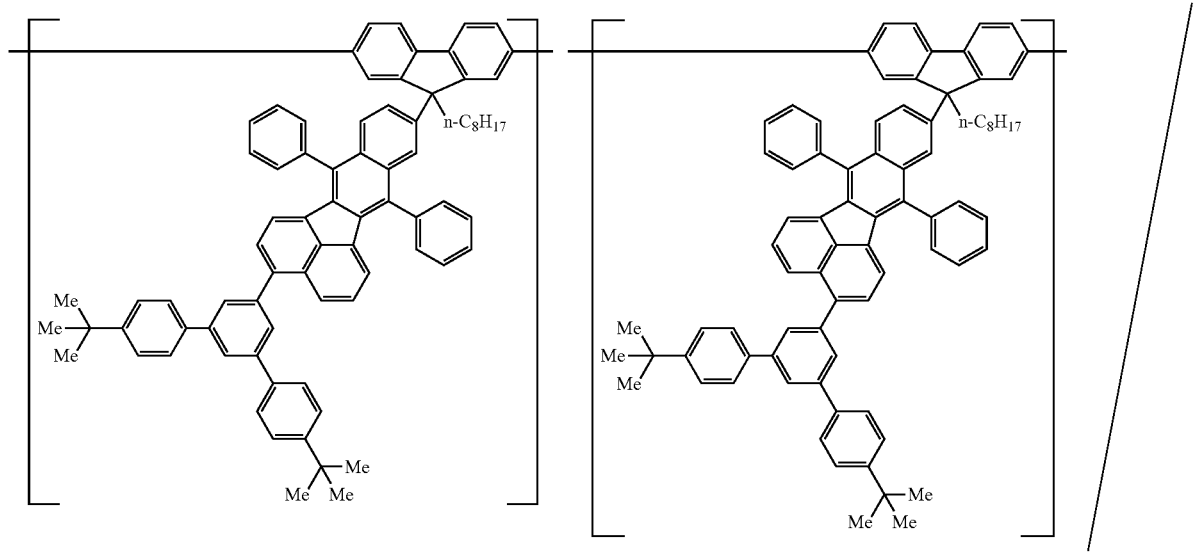

P1

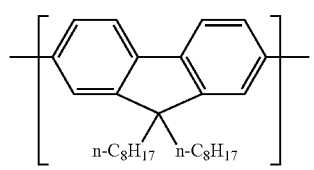

-continued
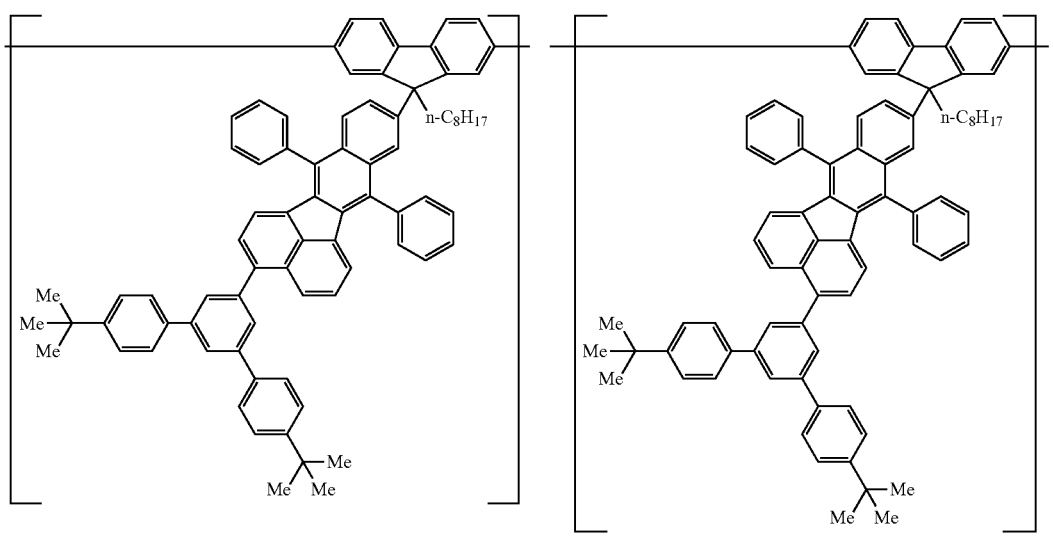
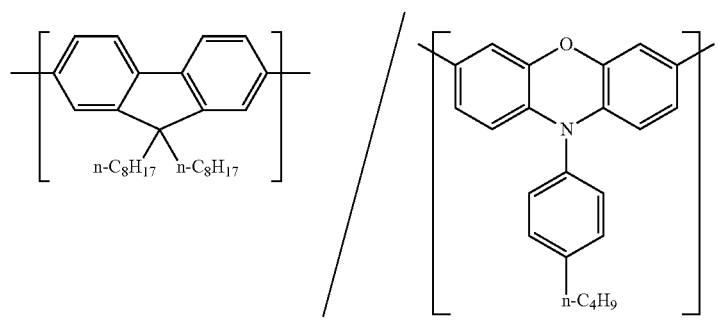
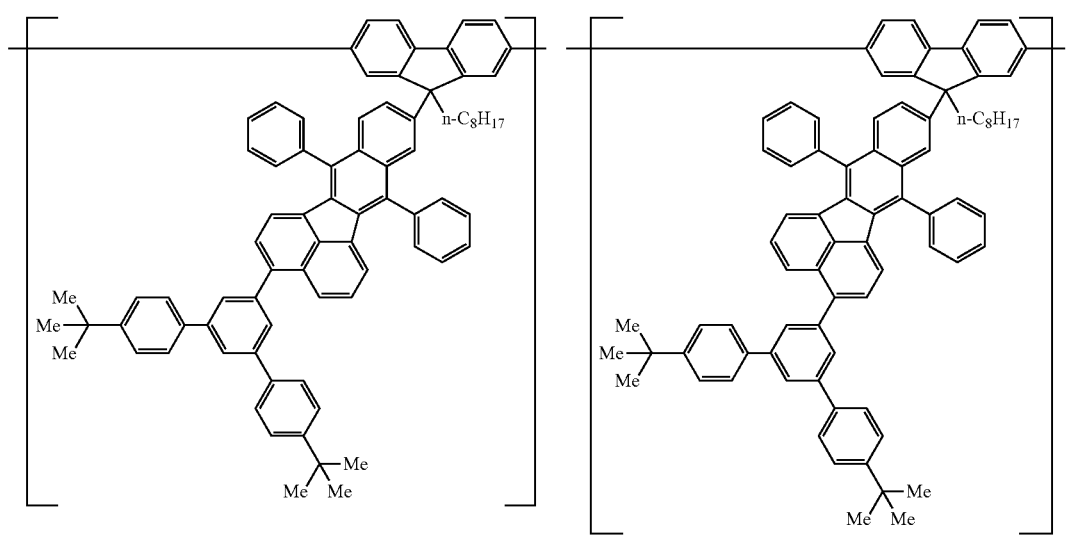

-continued
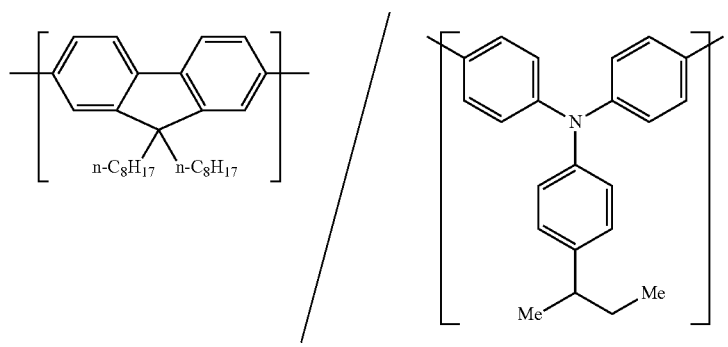
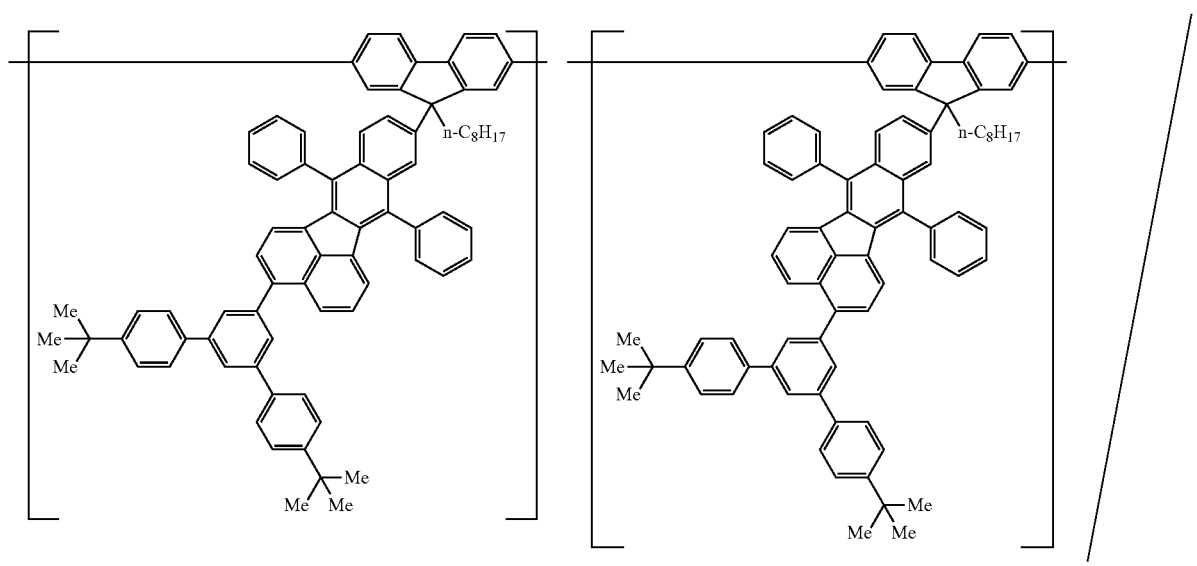
P4
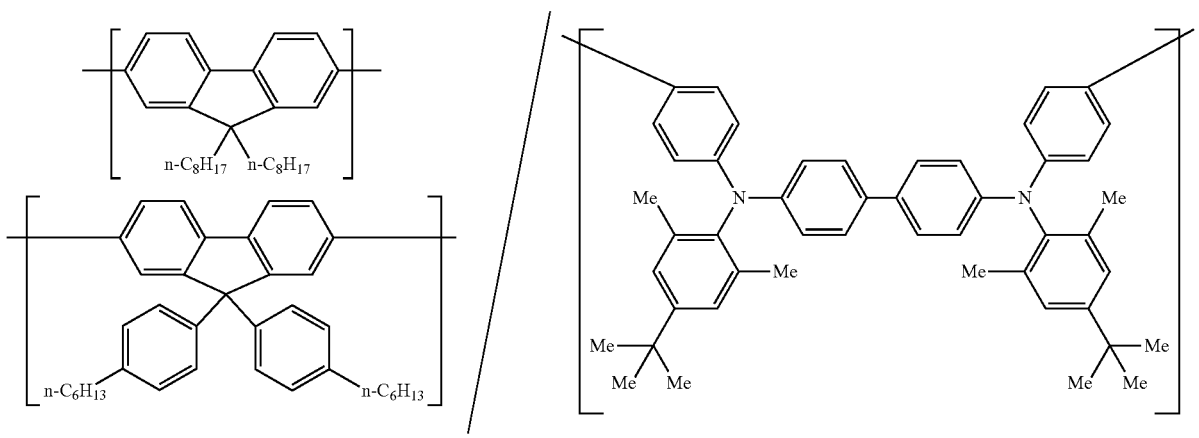

-continued
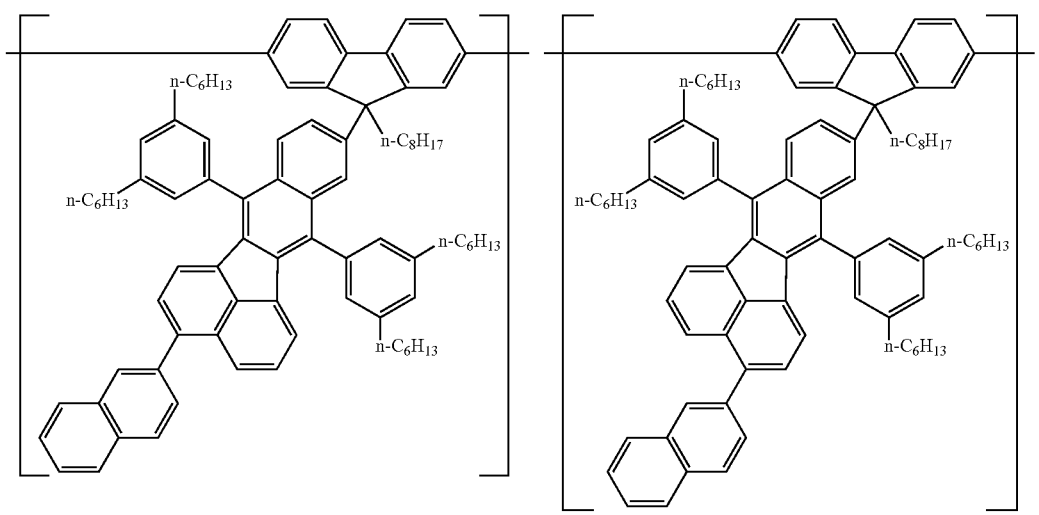
P5
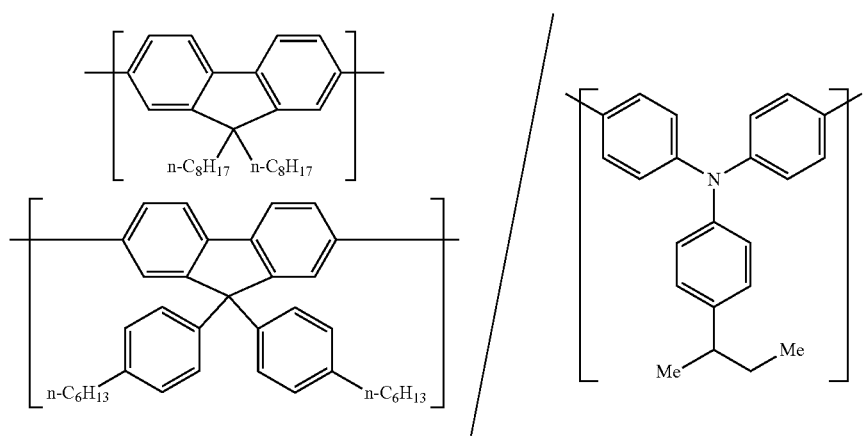
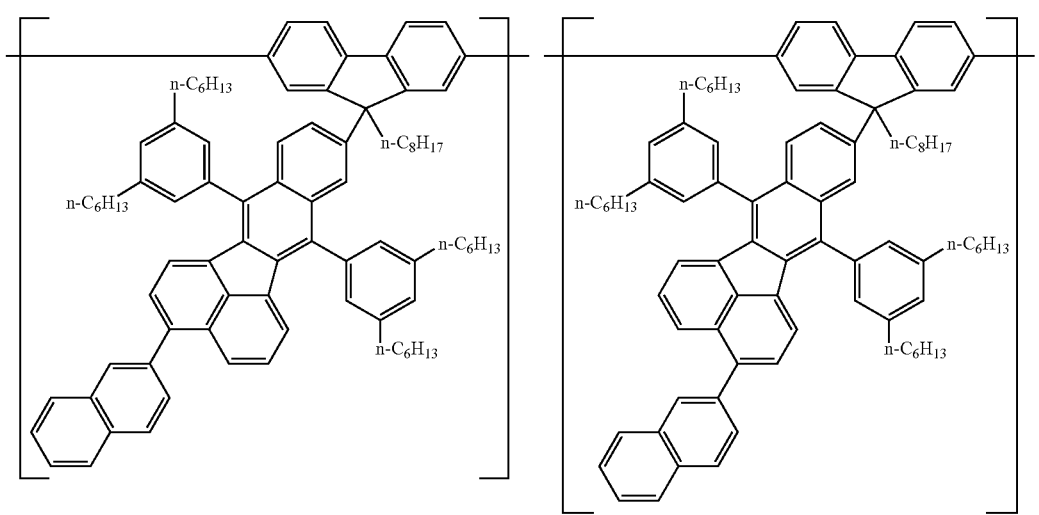
P6

57
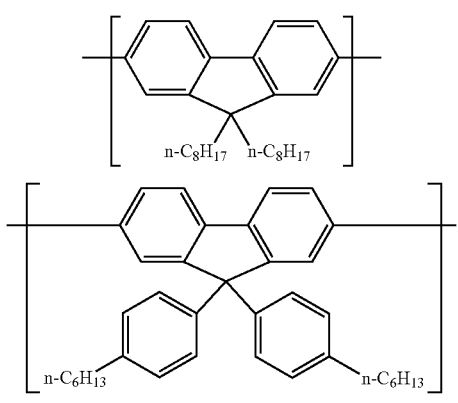
58
-continued
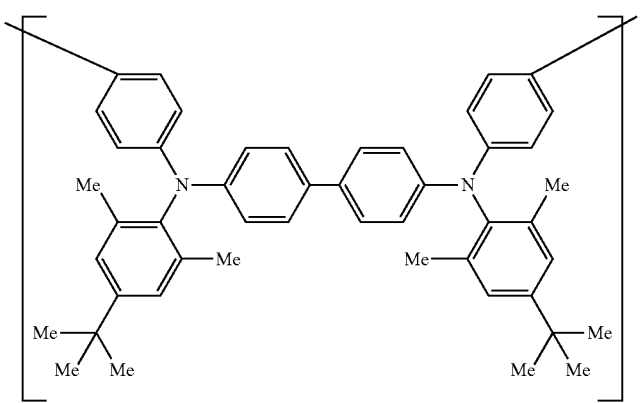
P7
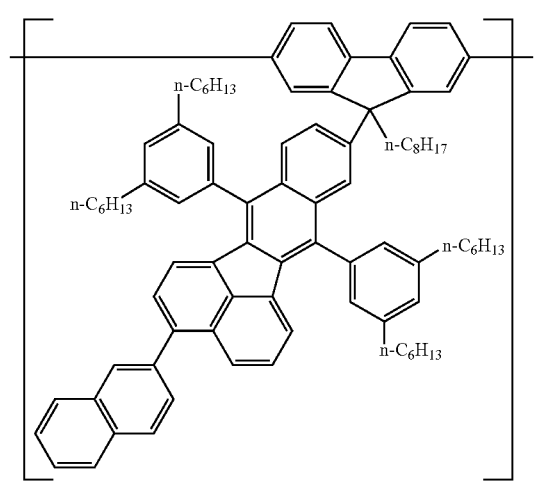
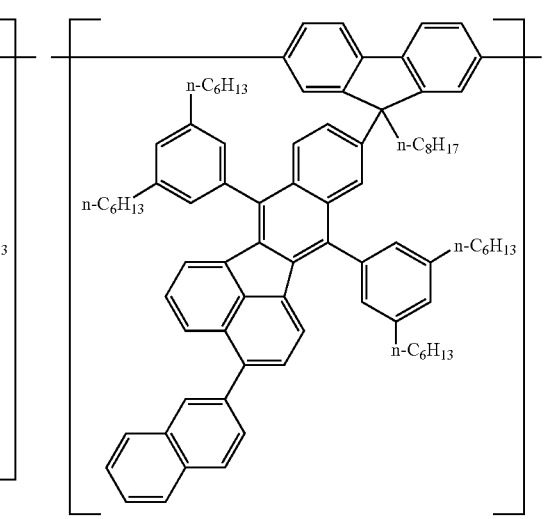
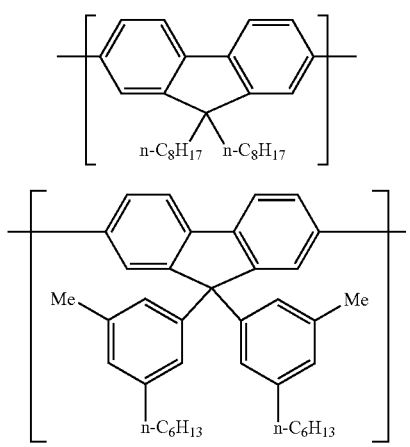
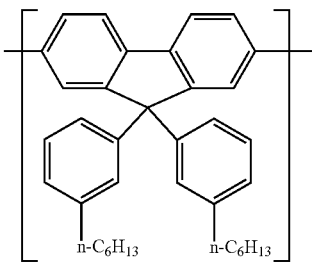

-continued
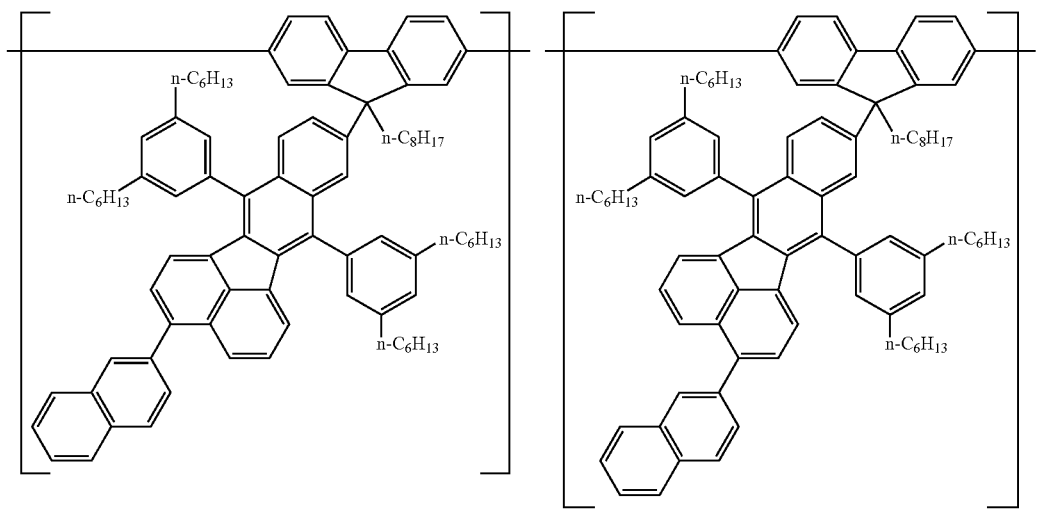
P8
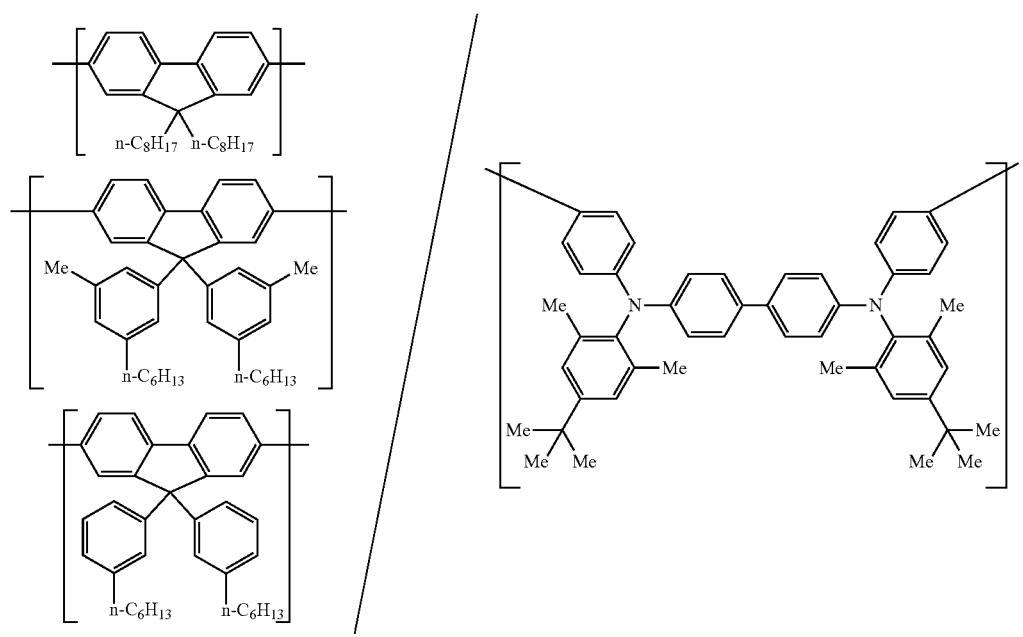

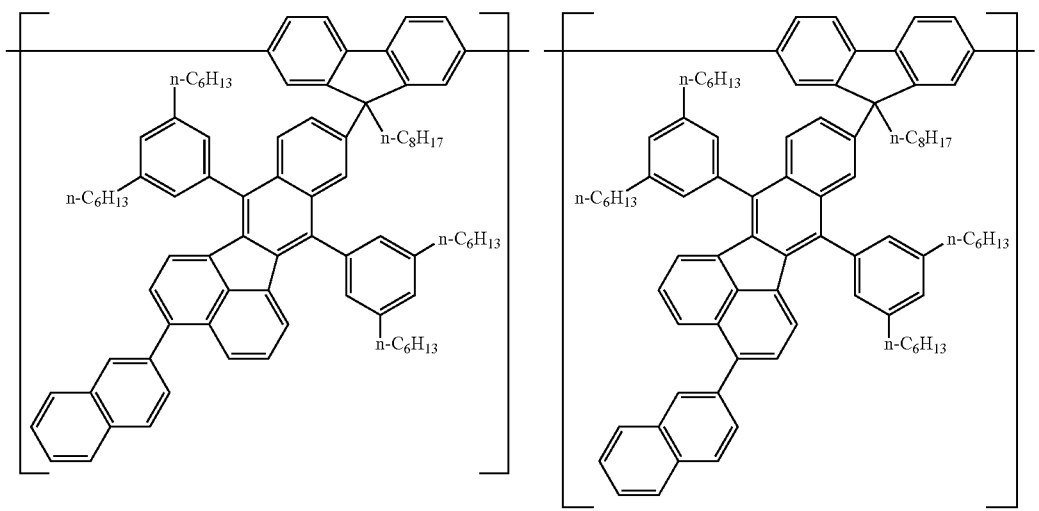
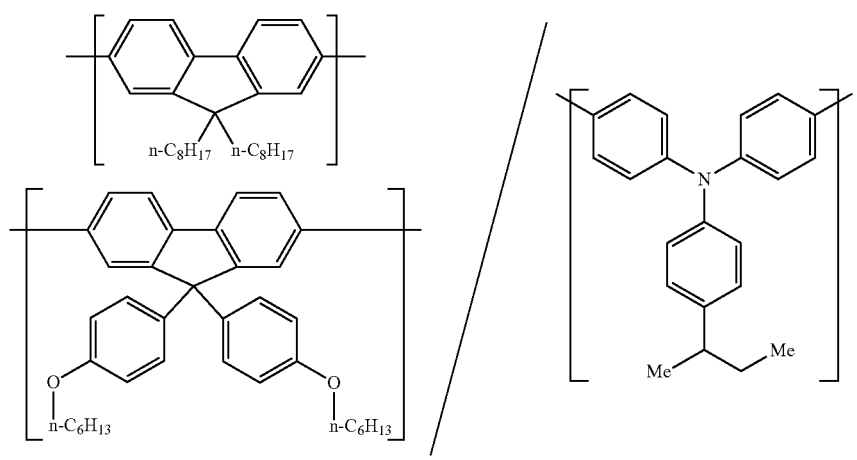
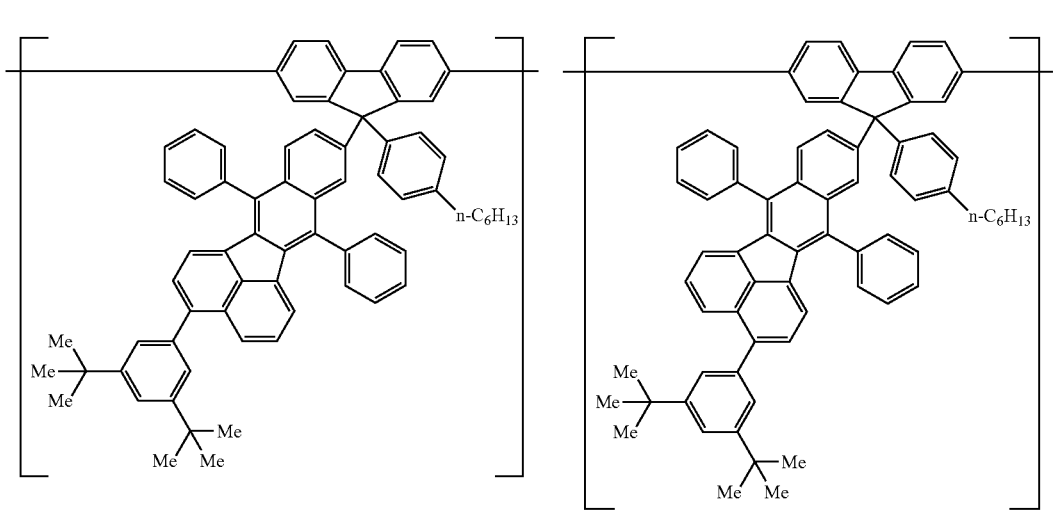

-continued
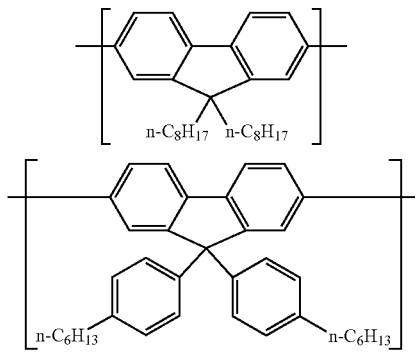
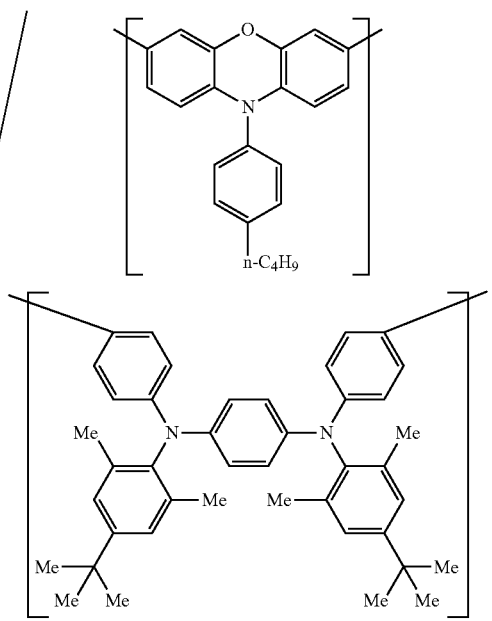
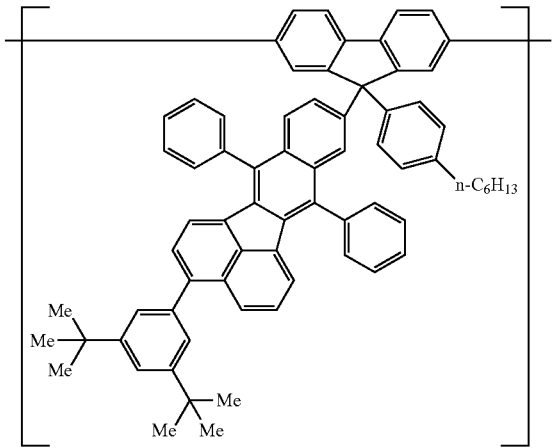
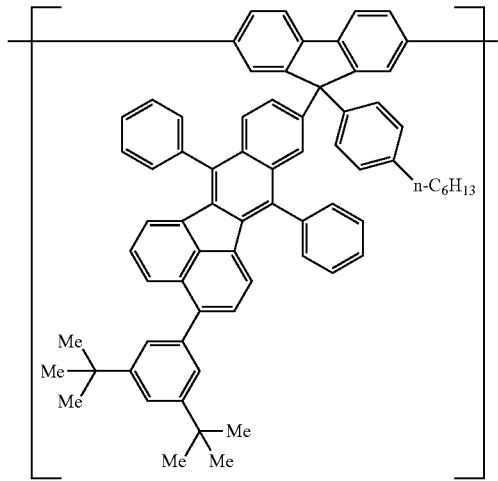
P11
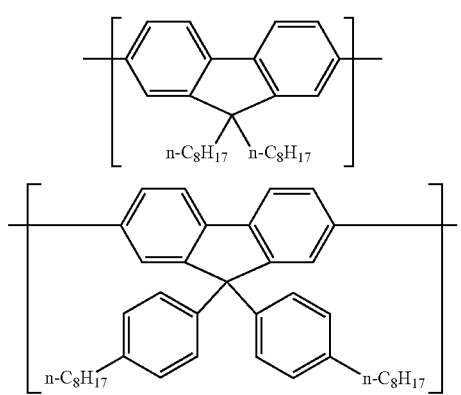
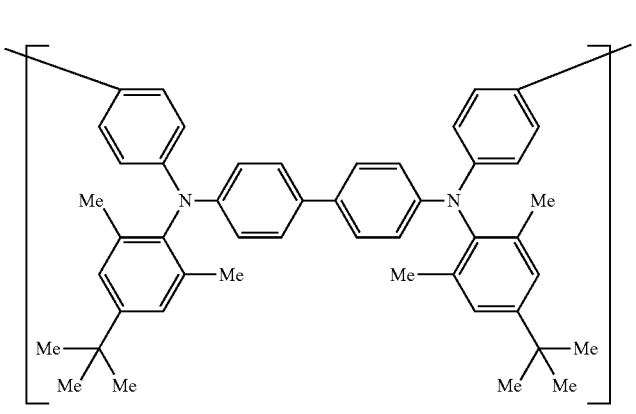

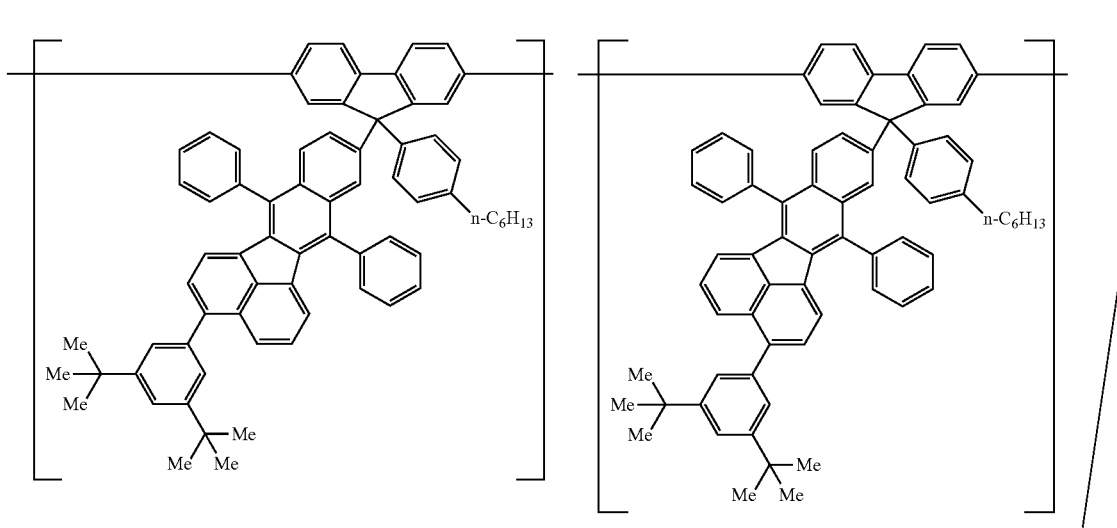
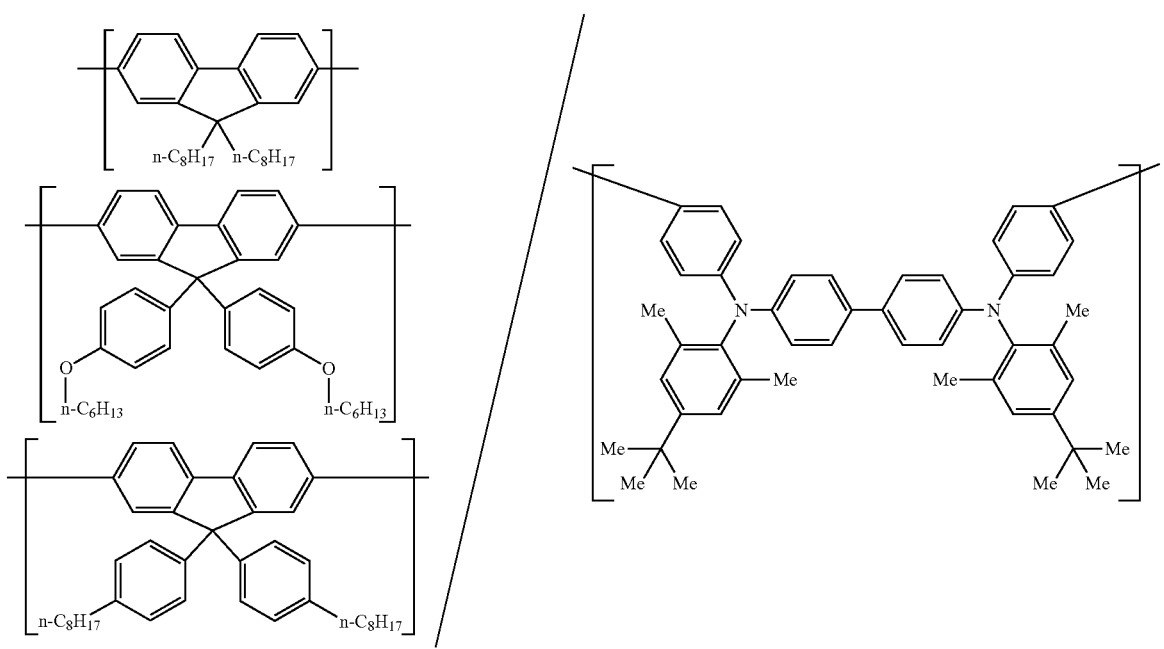
P12

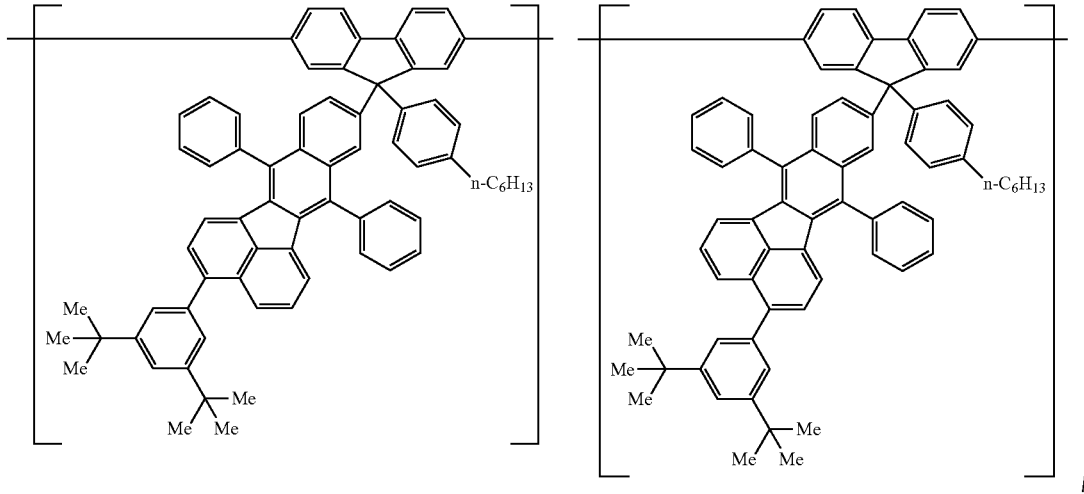
P13
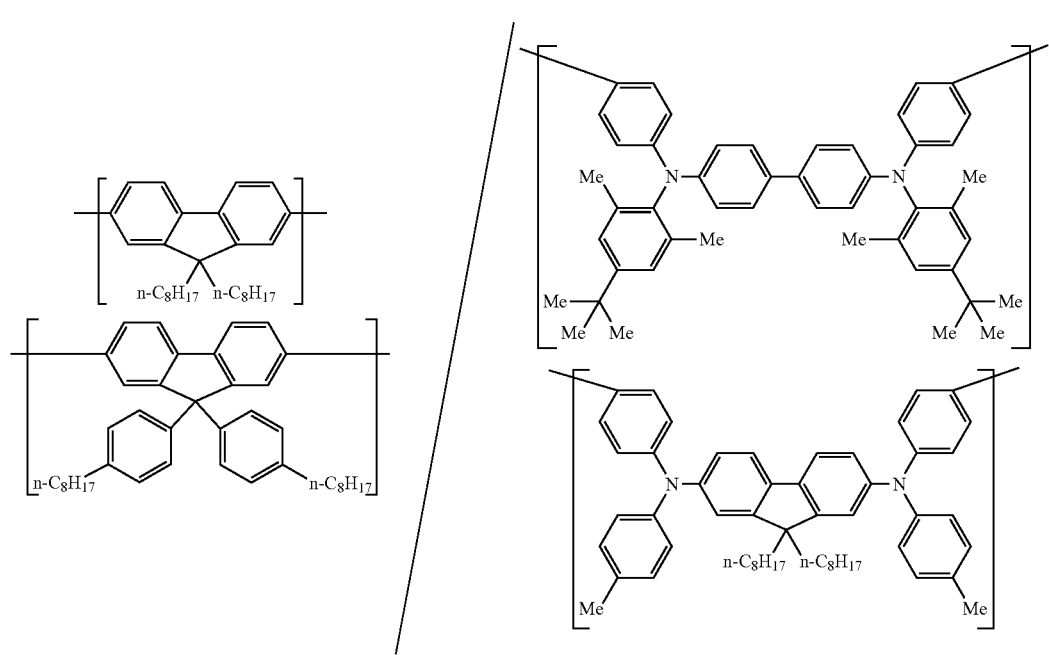

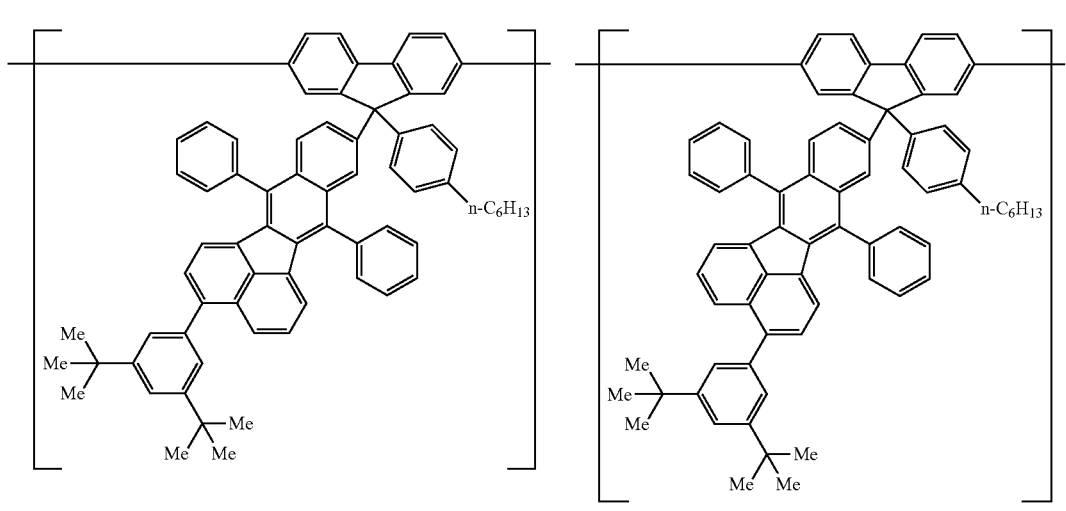
P14
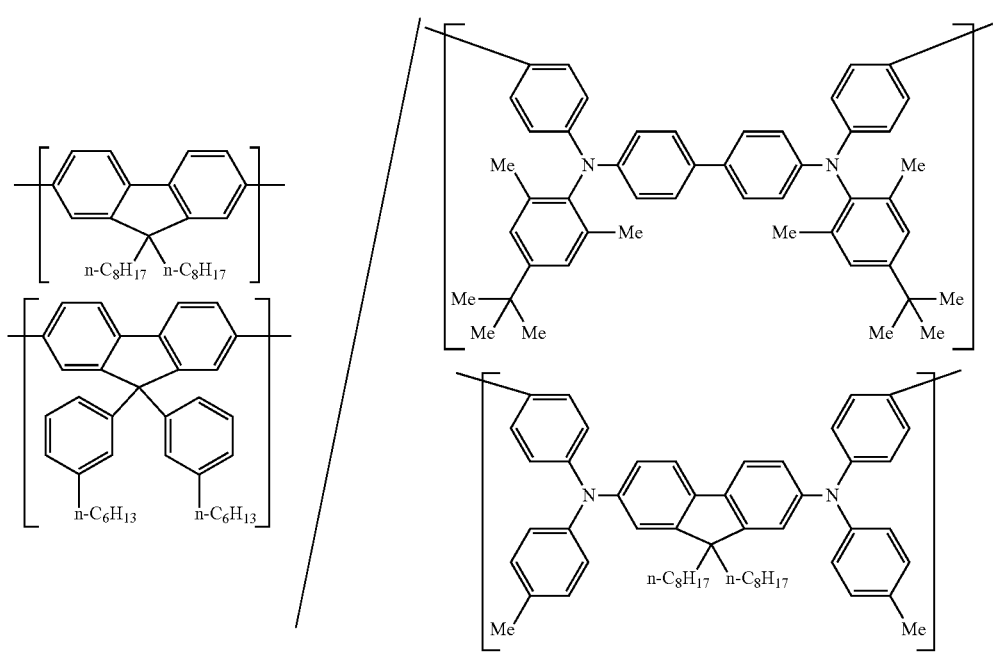

-continued
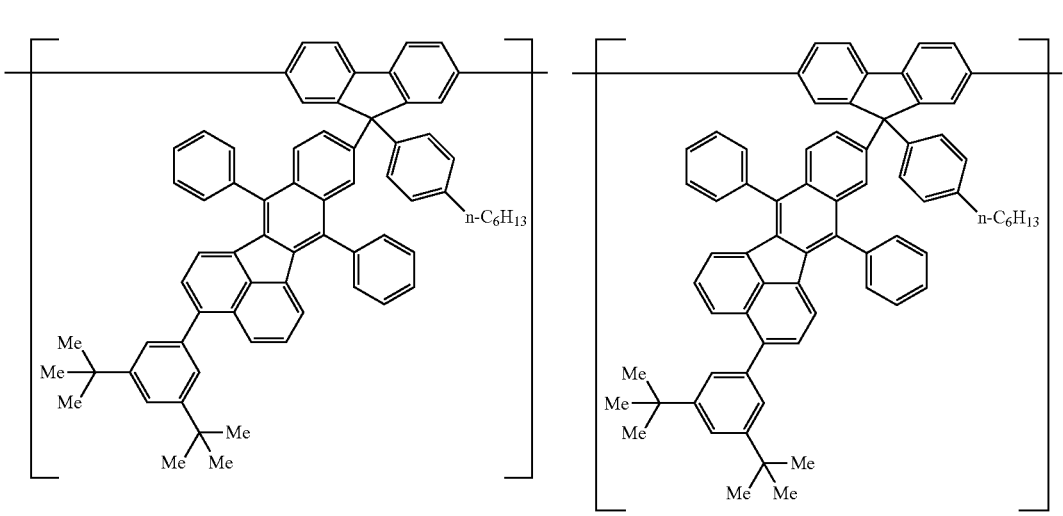
P15
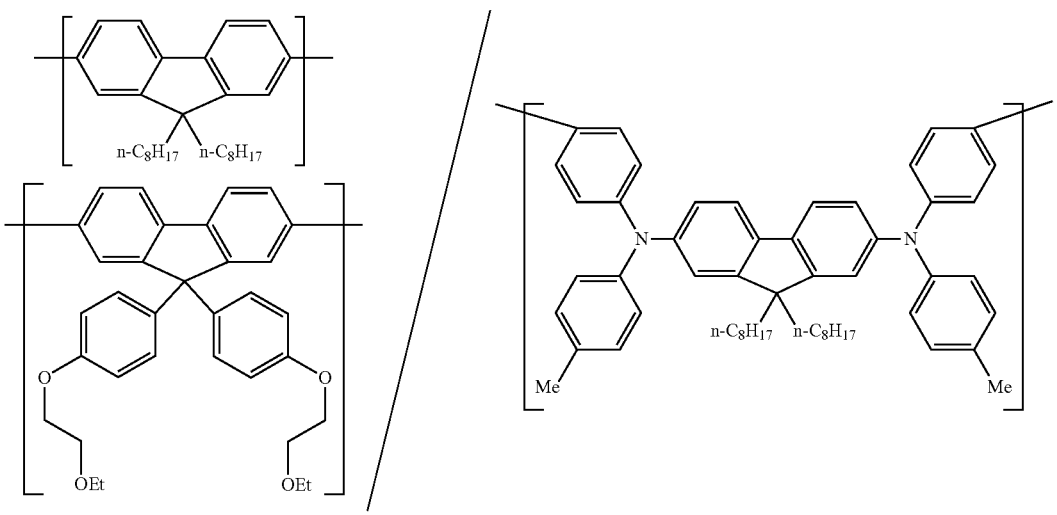
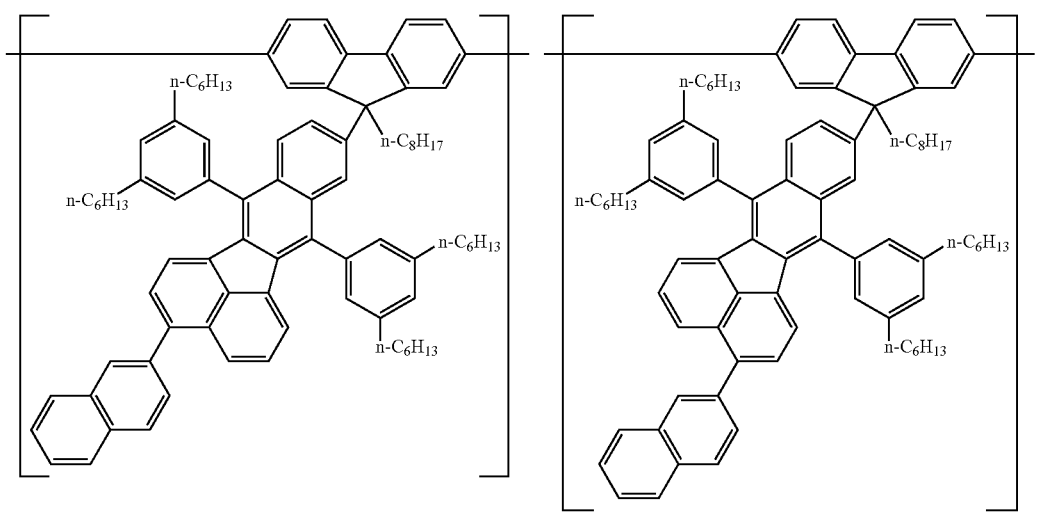
P16

-continued
73
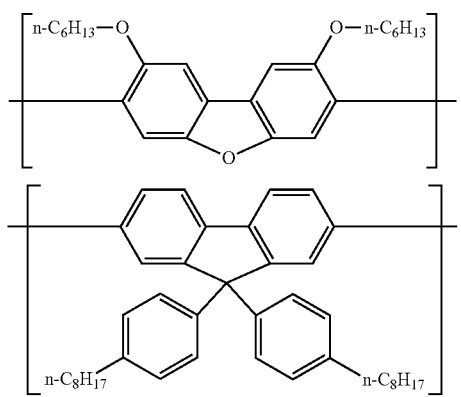
74
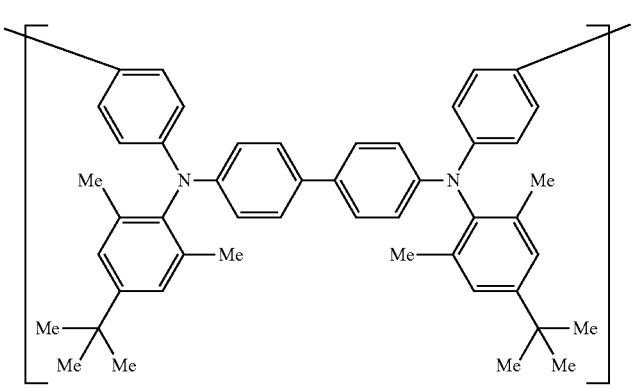
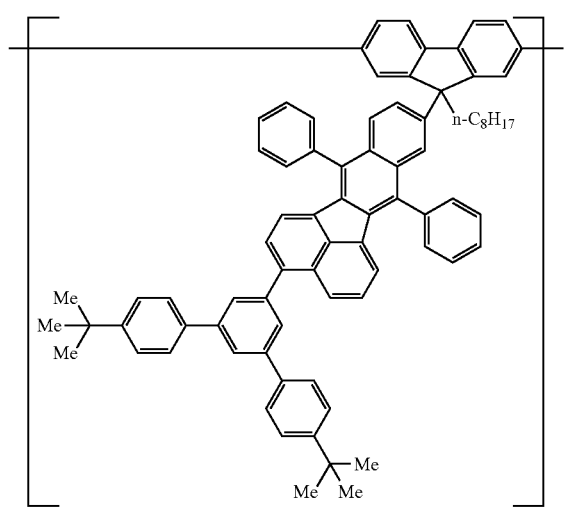
P17
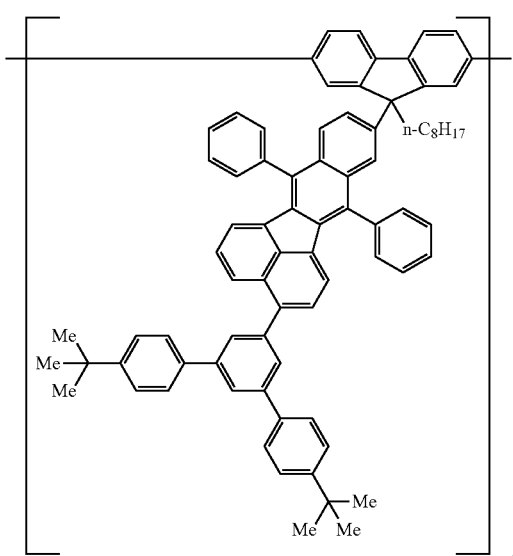
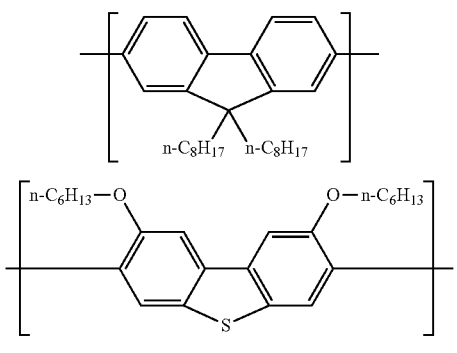
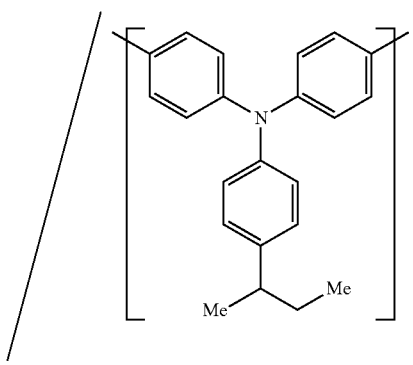

-continued
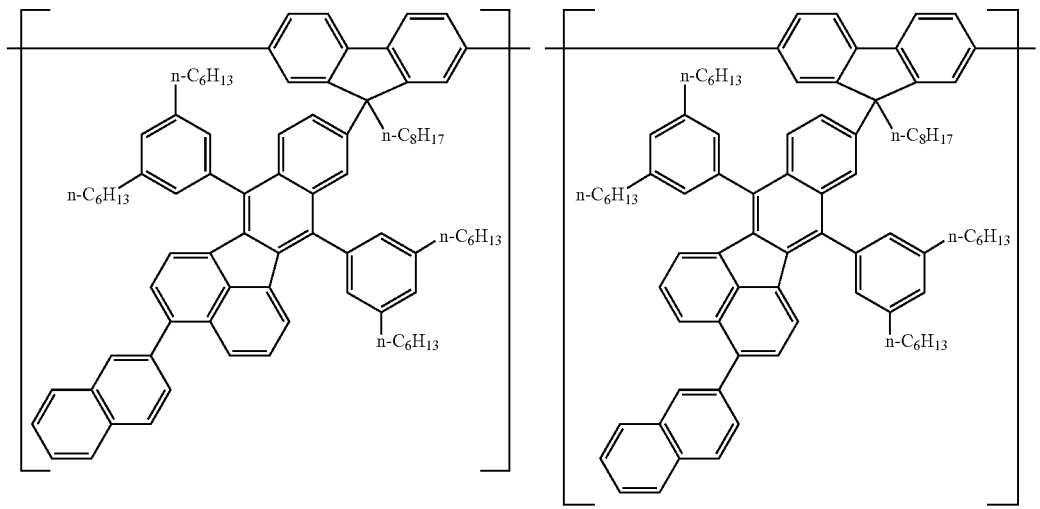
P18
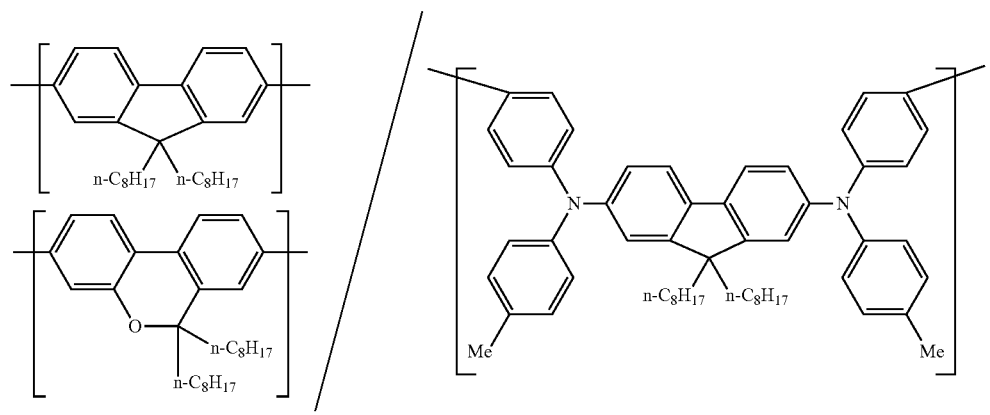
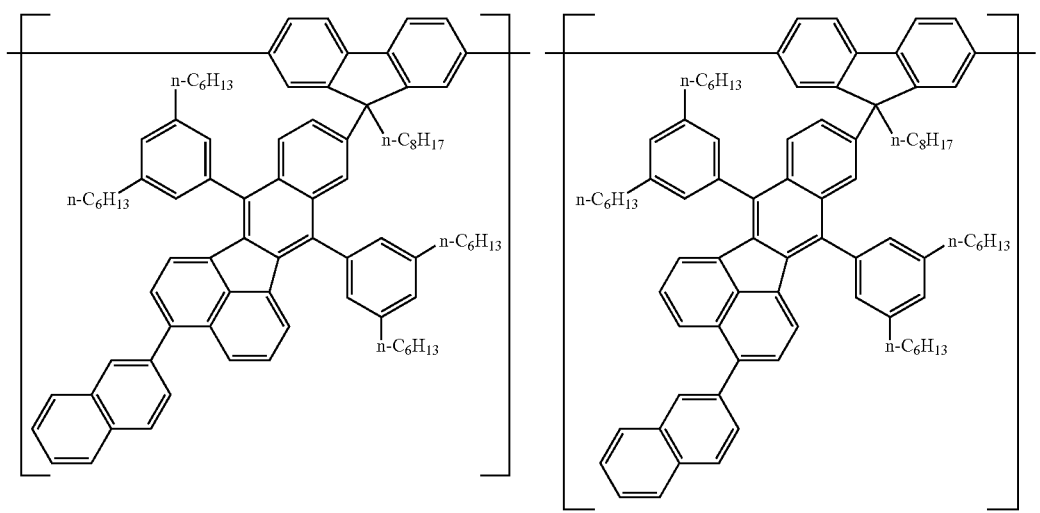
P19

-continued
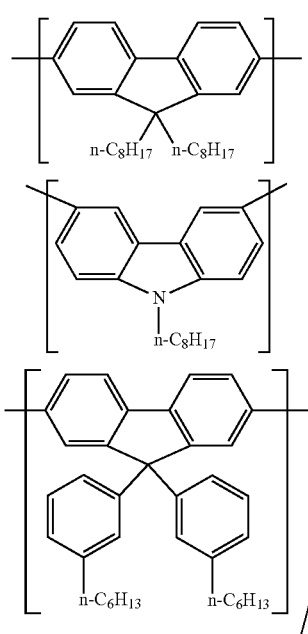
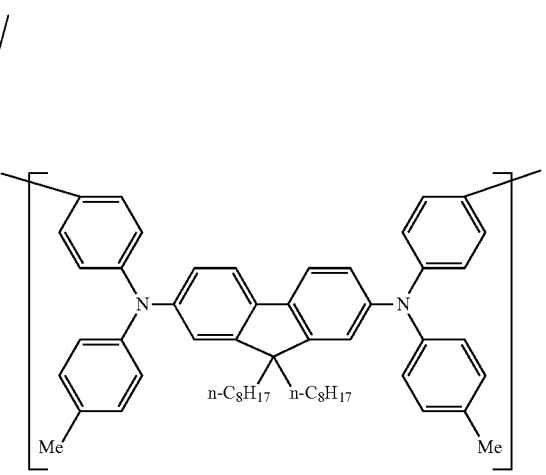
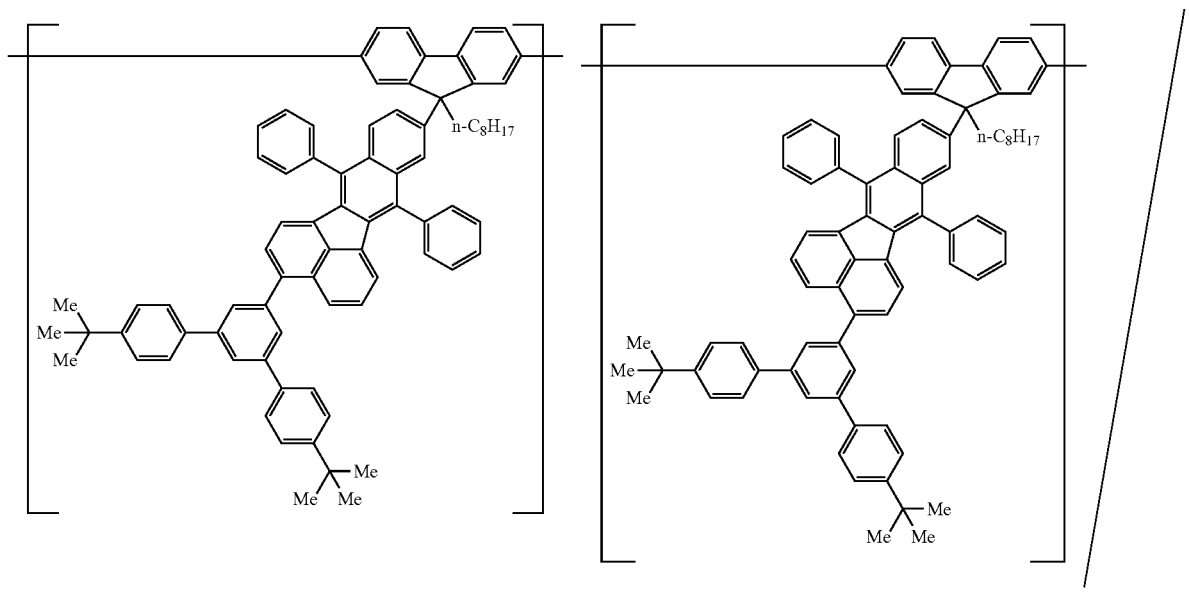
P20

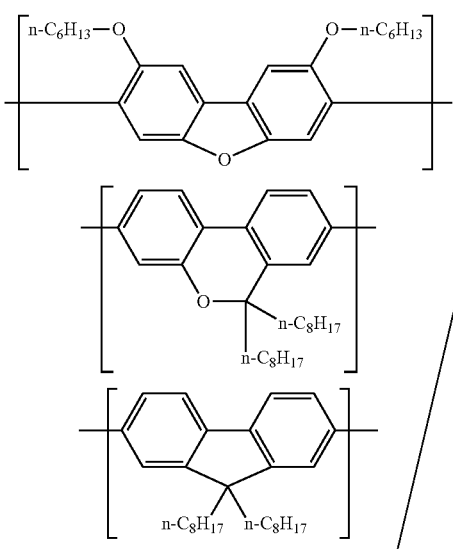

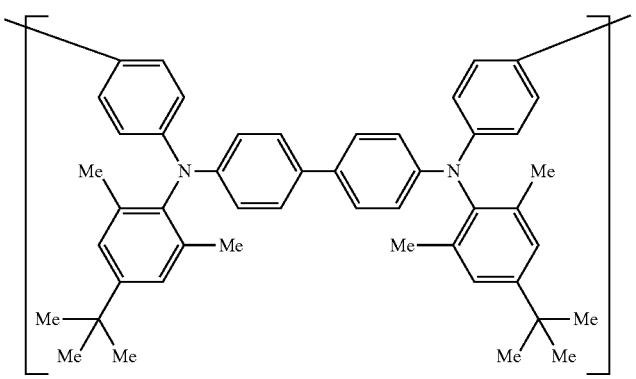

In the polymer compound according to the present invention, if a polymerization active group remains intact at the end group, there is a possibility of lowering of the light emitting property and the life of a light emitting device fabricated using this polymer compound. Thus, it is preferable that the end group is a stable group (for example, an aryl group or a monovalent aromatic heterocyclic group).

The polymer compound of the present invention may be any copolymer, and may be any of, for example, a block copolymer, a random copolymer, an alternative copolymer, a graft copolymer and the like.

The polymer compound according to the present invention is useful as a light emitting material, a charge transporting material or the like, and in use, may also be used in the form of a polymer composition described later together with other compounds.

The polymer compound according to the present invention has a polystyrene-equivalent number-average molecular weight (Mn) according to gel permeation chromatography (hereinafter, referred to as "GPC".) of usually $1 \times 10^3$ to $1 \times 10^8$, preferably $1 \times 10^4$ to $1 \times 10^6$.

The polymer compound according to the present invention has a polystyrene-equivalent weight-average molecular weight (Mw) of usually $1 \times 10^3$ to $1 \times 10^8$, and since film formability, and the light emission efficiency of a light emitting device obtained from this polymer compound are excellent, of preferably $1 \times 10^4$ to $5 \times 10^6$.

The polymer compound according to the present invention has a glass transition temperature of preferably 70° C. or more, more preferably 100° C. or more, since durability against various processes for fabricating a light emitting device and the like and stability and heat resistance against heat generation during driving of a light emitting device are excellent.

<Method of Producing Polymer Compound>

The polymer compound according to the present invention may be produced by any methods, and preferable embodiments thereof will be illustrated below.

When the polymer compound according to the present invention is a polymer compound comprising a first constitutional unit represented by the above-described formula (1) and a second constitutional unit represented by the above-described formula (5), this polymer compound can be produced by a method comprising a step of dissolving a compound represented by the following formula (1M) and a compound represented by the following formula (5M) if necessary in an organic solvent and polymerizing them by a polymerization method such as known ary-aryl coupling and the like using an alkali, a suitable catalyst, and a compound as a ligand.

(1M)

[in the formula (1M), $Ar^1$ and E each independently represent the same meaning as described above. $Z^1$ and $Z^2$ each independently represent any group selected from the group consisting of the above-described Substituent Group A and the above-described Substituent Group B. aa is an integer of 1 or more.]

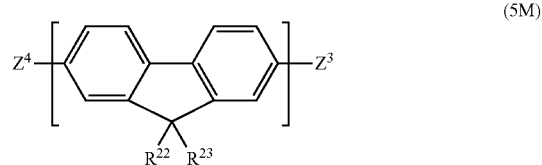

(5M)

[in the formula (5M), $R^{22}$ and $R^{23}$ each independently represent the same meaning as described above. $Z^3$ and $Z^4$ each independently represent any group selected from the group consisting of the above-described Substituent Group A and the above-described Substituent Group B.]

When the polymer compound according to the present invention is a polymer compound comprising at least one constitutional unit selected from the group consisting of a first constitutional unit represented by the above-described formula (1), a second constitutional unit represented by the above-described formula (5), a third constitutional unit represented by the following formula (6) and a fourth constitutional unit represented by the following formula (7), this polymer compound can be produced by a method comprising a step of dissolving a compound represented by the above-described formula (1M), a compound represented by the above-described formula (5M), a compound represented by the following formula (6M) and/or a compound represented by the following formula (7M) if necessary in an organic solvent and copolymerizing them by a polymerization method such as known aryl-aryl coupling and the like using an alkali, a suitable catalyst, and a compound as a ligand.

$$Z^6\!-\!\!\left[\mathrm{Ar}^2\right]\!-\!Z^5 \tag{6M}$$

[in the formula (6M), $Ar^2$ is defined above. $Z^5$ and $Z^6$ each independently represent a group selected from the group consisting of the above-described Substituent Group A and the above-described Substituent Group B.]

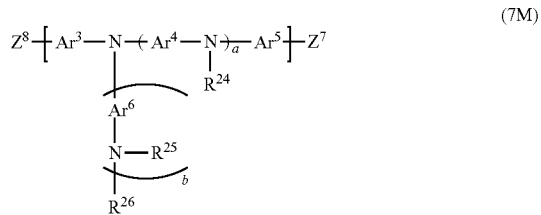

(7M)

[in the formula (7M), $Ar^2$, $Ar^4$, $Ar^5$ and $Ar^6$ each independently represent the same meaning as described above. $Z^7$ and $Z^8$ each independently represent a group selected from the group consisting of the above-described Substituent Group A and the above-described Substituent Group B.]

The alkyl group represented by $R^{27}$, $R^{28}$ and $R^{29}$ includes a methyl group, an ethyl group, a propyl group, an isopropyl group, a butyl group, a sec-butyl group, an isobutyl group, a pentyl group, a 2-methylbutyl group, an isoamyl group, a hexyl group, a heptyl group, an octyl group, a 2-ethylhexyl group, a nonyl group, a decyl group, a 3,7-dimethyloctyl group, a dodecyl group and the like, and these groups may have a substituent. These alkyl groups have a carbon atom number of usually 1 to 20, preferably 1 to 15, more preferably 1 to 10.

The aryl group represented by $R^{27}$ is the same as explained and exemplified as the aryl group represented by $R^1$ in the above-described formula (2), and a phenyl group, a 4-tolyl group, a 4-methoxya phenyl group, a 4-nitrophenyl group, a 3-nitrophenyl group, a 2-nitrophenyl group and 4-trifluoromethylphenyl group are preferable since synthesis thereof is easy and reactivity in polymerization is excellent.

The group represented by —O—S(=O)$_2$R$^{27}$ includes a methanesulfonyloxy group, a trifluoromethanesulfonyloxy group, a phenylsulfonyloxy group, a 4-methylphenylsulfonyloxy group, a 4-trifluoromethylphenylsulfonyloxy group and the like.

The group represented by —B(OR$^{28}$)$_2$ includes groups represented by the following formulae, and the like.

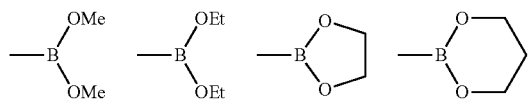

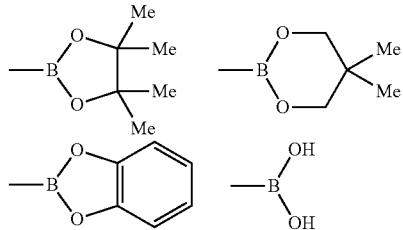

The group represented by —BF$_4^-$Q$^1$ includes —BF$_4^-$K$^+$ and the like.

The group represented by —Sn(R$^{36}$)$_3$ includes a trimethylstannyl group, a triethylstannyl group, a tributylstannyl group and the like.

In the above-described formula (5M), $Z^3$ and $Z^4$ each independently represent a group selected from the group consisting of the above-described Substituent Group A and the following Substituent Group B, and when both $Z^1$ and $Z^2$ in the above-described formula (1M) represent a group selected from the above-described Substituent Group A, then, at least one of $Z^3$ and $Z^4$ is a group selected from the above-described Substituent Group B, and when both $Z^1$ and $Z^2$ in the above-described formula (1M) represent a group selected from the above-described Substituent Group B, then, at least one of $Z^3$ and $Z^4$ is a group selected from the above-described Substituent Group A.

As the compound represented by the above-described formula (1M), the compound represented by the above-described formula (5M), the compound represented by the above-described formula (6M) and the compound represented by the above-described formula (7M), those synthesized and isolated previously may be used, or those synthesized in the reaction system may be used as they are. When the resultant polymer compound is used in a light emitting device, its purity tends to influence the performance of the light emitting device. Therefore, it is preferable that these compounds are purified by methods such as distillation, sublimation purification, recrystallization and the like.

The above-described polymerization method includes a method of polymerization by the Suzuki coupling reaction (Chemical Review (Chem. Rev.), vol. 95, pp. 2457-2483 (1995)), a method of polymerization by the Grignard reaction (Bull. Chem. Soc. Jpn., vol. 51, p. 2091 (1978)), a method of polymerization with a Ni(0) catalyst (Progress in Polymer Science, vol. 17, pp. 1153 to 1205, 1992), a method using the Stille coupling reaction (European Polymer Journal, vol. 41, pp. 2923-2933 (2005)), and the like. Of them, the method of polymerization by the Suzuki coupling reaction and the method of polymerization with a Ni(0) catalyst are preferable since synthesis of raw materials is easy and the operation of the polymerization reaction is simple, and owing to easiness of control of the structure of a polymer compound, more preferable are methods of polymerization by an aryl-aryl cross coupling reaction such as the Suzuki coupling reaction, the Grignard reaction, the Stille coupling reaction and the like, particularly preferable are methods of polymerization by the Suzuki coupling reaction.

As the group selected from the group consisting of Substituent Group A and Substituent Group B, suitable groups may be advantageously selected depending on the kind of the polymerization reaction, and when the method of polymerization by the Suzuki coupling reaction is selected, a chlorine atom, a bromine atom and an iodine atom are preferable and a bromine atom is more preferable as the group selected from Substituent Group A and a group represented by —B(OR$^{28}$)$_2$ is preferable as the group selected from Substituent Group B, since synthesis thereof is simple and handling of each compound is easy.

The above-described polymerization method includes methods of reacting a compound represented by the above-described formula (1M), a compound represented by the above-described formula (5M), a compound represented by the above-described formula (6M) and/or a compound represented by the above-described formula (7M), if necessary, together with a suitable catalyst and a suitable base. When the method of polymerization by the Suzuki coupling reaction is selected, the ratio of the total molar number of groups selected from Substituent Group A to the total molar number of groups selected from Substituent Group B, carried on the compound represented by the above-described formula (1M), the compound represented by the above-described formula (5M), the compound represented by the above-described formula (6M) and the compound represented by the above-described formula (7M), may be advantageously adjusted, for obtaining a polymer compound having a desired molecular weight. Usually, the ratio of the total molar number of groups selected from Substituent Group B to the total molar number of groups selected from Substituent Group A is preferably 0.95 to 1.05, more preferably 0.98 to 1.02, further preferably 0.99 to 1.01.

In the method of producing the polymer compound according to the present invention, the charge ratio of the compound represented by the above-described formula (1M) with respect to all compounds is preferably 0.1 mol % or more, and preferably 20 mol % or less. By this, a polymer compound in which the ratio of the constitutional unit represented by the above-described formula (1) with respect to the sum of all constitutional units is 0.1 to 20 mol % can be produced easily.

In the method of producing the polymer compound according to the present invention, it is preferable that a monomer is polymerized in the presence of a catalyst. The catalyst includes transition metal complexes such as palladium complexes such as palladium[tetrakis(triphenylphosphine)], [tris(dibenzylideneacetone)]dipalladium, palladium acetate, dichlorobistriphenylphosphinepalladium and the like, and complexes obtained by coordination of a ligand such as triphenylphosphine, tri-tert-butylphosphine, tricyclohexylphosphine and the like to these transition metal complexes, in the case of polymerization by the Suzuki coupling reaction.

In the case of polymerization with a Ni(0) catalyst, the Ni(0) catalyst includes transition metal complexes such as nickel complexes such as nickel[tetrakis(triphenylphosphine)], [1,3-bis(diphenylphosphino)propane]dichloronickel, [bis(1,4-cyclooctadiene)]nickel and the like, and complexes obtained by coordination of a ligand such as triphenylphosphine, tri-tert-butylphosphine, tricyclohexylphosphine, diphenylphosphinopropane, bipyridyl and the like to these transition metal complexes.

As the above-described catalyst, those synthesized previously may be used, or those prepared in the reaction system may be used as they are. These catalysts may be used singly or in combination.

The use amount of the catalyst may advantageously be an effective amount as the catalyst, and for example, usually 0.0001 to 300 mol %, preferably 0.001 to 50 mol %, more preferably 0.01 to 20 mol %, in terms of the molar number of a transition metal, with respect to 100 mol % of the sum of all compounds in the polymerization reaction.

In polymerization by the Suzuki coupling reaction, a base is preferably used, and the base includes inorganic bases such as sodium carbonate, potassium carbonate, cesium carbonate, potassium fluoride, cesium fluoride, tripotassium phosphate and the like, and organic bases such as tetrabutylammonium fluoride, tetrabutylammonium chloride, tetrabutylammonium bromide, tetraethylammonium hydroxide, tetrabutylammonium hydroxide and the like.

The use amount of the base is usually 50 to 2000 mol %, preferably 100 to 1000 mol %, with respect to 100 mol % of the sum of all compounds in the polymerization reaction.

The polymerization reaction may be carried out in the absence of a solvent or in the presence of a solvent, and usually carried out in the presence of an organic solvent. Here, the organic solvent includes toluene, xylene, mesitylene, tetrahydrofuran, 1,4-dioxane, dimethoxyethane, N,N-dimethylacetamide, N,N-dimethylformamide and the like. It is desirable to use a solvent subjected to a deoxidation treatment since the molecular weight can be controlled. The organic solvents may be used singly or in combination.

The use amount of the organic solvent is an amount with which the total concentration of all monomers in the polymerization reaction is preferably 0.1 to 90 wt %, more preferably 1 to 50 wt %, further preferably 2 to 30 wt %.

The reaction temperature of the polymerization reaction is preferably −100 to 200° C., more preferably −80 to 150° C., further preferably 0 to 120° C.

The reaction time is usually 1 hour or more, preferably 2 to 500 hours.

In the case of use of a compound having a group represented by —MgY$^1$ as the group represented by Z$^1$ to Z$^8$ in the method of producing the polymer compound according to the present invention, the polymerization reaction is preferably carried out under dehydration conditions. In contrast, when the polymerization reaction is the Suzuki coupling reaction, the base to be used may be used as an aqueous solution, and as the solvent, water may be used in addition to the above-described organic solvent.

For avoiding remaining of a polymerization active group at the end of the polymer compound according to the present invention in the polymerization reaction, a compound represented by the following formula (9) may be used as a chain terminating agent. By this, a compound in which its end is an aryl group or a monovalent aromatic heterocyclic group can be obtained.

Z$^9$—Ar$^7$           (9)

[in the formula (9), Ar$^7$ represents an aryl group or a monovalent aromatic heterocyclic group. Z$^9$ represents a group selected from the group consisting of Substituent Group A and Substituent Group B.]

In the above-described formula (9), the aryl group and the monovalent aromatic heterocyclic group represented by Ar$^7$ are the same as explained and exemplified as the above-described aryl group and monovalent aromatic heterocyclic group.

A post treatment of the polymerization reaction can be carried out by known methods, and for example, can be carried out by a method in which the reaction solution after the polymerization reaction is added to a lower alcohol such as methanol and the like to cause deposition of a precipitate which is then filtrated and dried.

When the purity of the polymer compound according to the present invention is low, it may advantageously be purified by usual methods such as recrystallization, reprecipitation, continuous extraction by a Soxhlet extractor, column chromatography and the like, and when the polymer compound according to the present invention is used in a light emitting device, its purity exerts an influence on device performances such as a light emission property and the like, thus, it is preferable to carry out purification treatments such as reprecipitation purification, chromatographic fractionation and the like, after condensation polymerization.

As the method of producing a compound represented by the above-described formula (1M), a method of producing a compound represented by the following formula (4M) will be explained as one example.

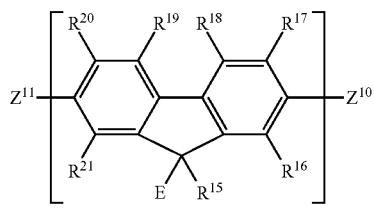

(4M)

[in the formula (4), $R^{15}$, $R^{16}$, $R^{17}$, $R^{18}$, $R^{19}$, $R^{20}$, $R^{21}$ and E each independently represent the same meaning as described above. $Z^{10}$ and $Z^{11}$ each independently represent a group selected from the group consisting of the above-described Substituent Group A and Group B.]

The method of producing a compound represented by the above-described formula (4) includes routes represented by the following reaction formula (R1) or the following reaction formula ($R^2$):

(R1)

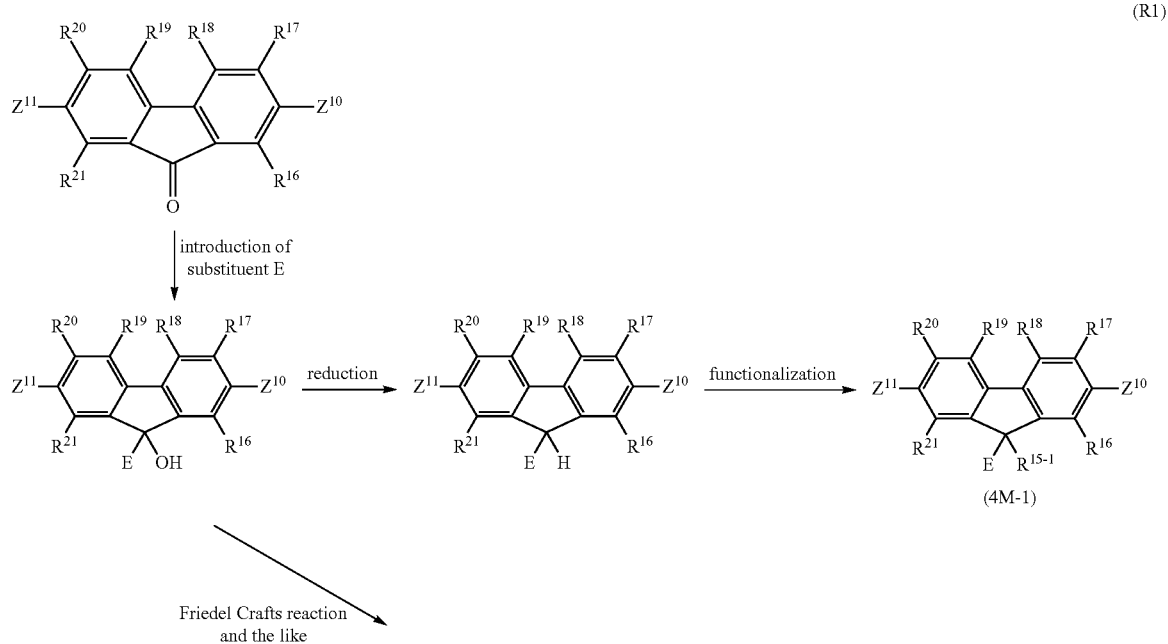

(4M-1)

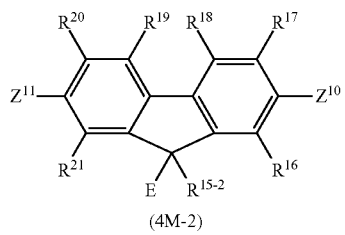

(4M-2)

(R2)

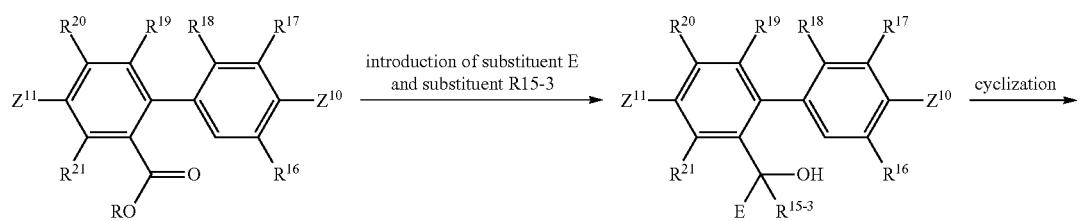

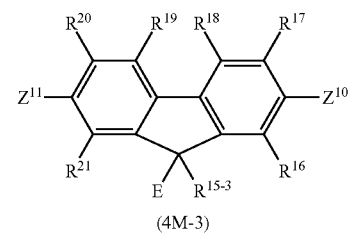

(4M-3)

[in the formulae (R1) and (R2), $R^{16}$, $R^{17}$, $R^{18}$, $R^{19}$, $R^{20}$, $R^{21}$ and E each independently represent the same meaning as described above. $R^{15-1}$, $R^{15-2}$ and $R^{15-3}$ each independently represent an alkyl group, an aryl group or a monovalent aromatic heterocyclic group. $Z^{10}$ and $Z^{11}$ each independently represent a group selected from the group consisting of Substituent Group A and Substituent Group B.], according to known production methods.

The alkyl group, the aryl group and the monovalent aromatic heterocyclic group represented by $R^{15-1}$, $R^{15-2}$ and $R^{15-3}$ are the same as explained and exemplified as the alkyl group, the aryl group and the monovalent aromatic heterocyclic group represented by $R^1$ described above.

$Z^{10}$ and $Z^{11}$ represent preferably a group selected from Substituent Group A, more preferably a halogen atom, since synthesis of a monomer compound is easy.

In the step of "introduction of substituent E", preferable reactors include compounds represented by the following formula (10):

$$E-Z^{12} \quad (10)$$

[in the formula (10), $Z^{12}$ represents a group selected from Substituent Group A. E is defined above.].

In the above-described formula (10), $Z^{12}$ represents preferably a halogen atom, since handling of the compound is easy.

The substituent E can be introduced, by converting a compound represented by the above-described formula (10) into a Grignard reagent or a lithium salt.

Examples of the compound represented by the above-described formula (10) include bromofluoranthene represented by the following formula:

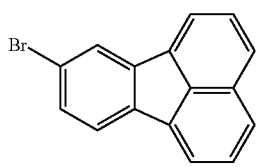 [SMILES: Brc1ccc2c(c1)-c1cccc3cccc-2c13]

described in Polycyclic Aromatic Compounds, 11(1-4), 261-266; 1996, 3-bromodiphenylbenzofluoranthene represented by the following formula:

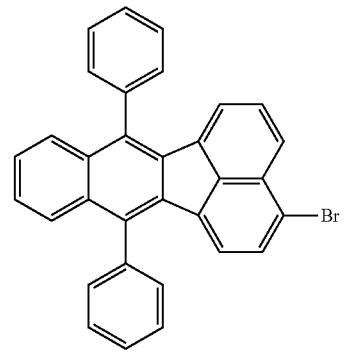 [SMILES: Brc1ccc2c3c(cccc13)-c1c-2c(-c2ccccc2)c2ccccc2c1-c1ccccc1]

described in Journal of Organic Chemistry, 62(3), 530-537; 1997, and 9- or 10-bromodiphenylbenzofluoranthene which can be produced by the following reaction formula:

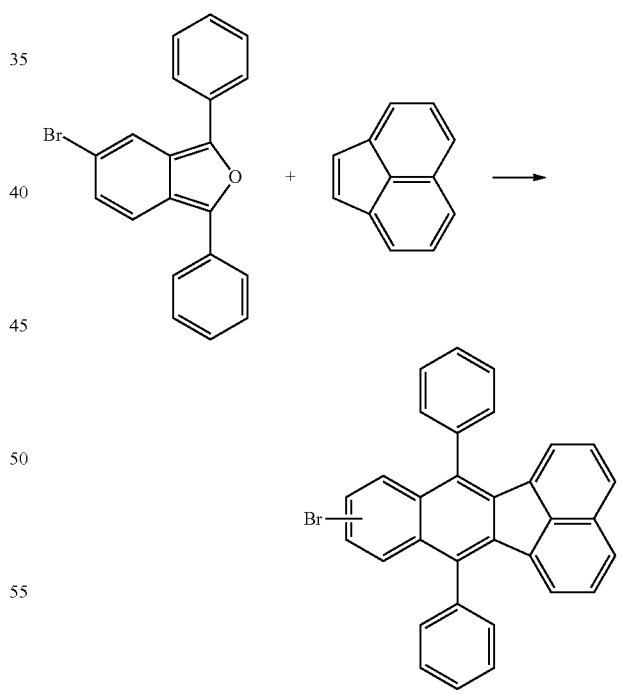

The compound in the formulae may have a substituent.

<Polymer Composition>

The polymer composition according to the present invention comprises the polymer compound according to the present invention and at least one material selected from the group consisting of hole transporting materials, electron transporting materials and light emitting materials.

The hole transporting material includes polyvinylcarbazole and derivatives thereof, polysilane and derivatives thereof, polysiloxane derivatives having an aromatic amine on the side chain or the main chain, pyrazoline derivatives, arylamine derivatives, stilbene derivatives, polyaniline and derivatives thereof, polythiophene and derivatives thereof, polypyrrole and derivatives thereof, poly(p-phenylenevinylene) and derivatives thereof, poly(2,5-thienylenevinylene) and derivatives thereof, and the like. Additionally, compounds described in JP-A No. 63-70257, JP-A No. 63-175860, JP-A No. 2-135359, JP-A No. 2-135361, JP-A No. 2-209988, JP-A No. 3-37992 and JP-A No. 3-152184 are also listed.

The content of the hole transporting material is preferably 1 to 500 parts by weight, more preferably 5 to 200 parts by weight, with respect to 100 parts by weight of the polymer compound in the polymer composition.

The electron transporting material includes oxadiazole derivatives, anthraquinodimethane and derivatives thereof, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, metal complexes of 8-hydroxyquinoline and derivatives thereof, polyquinoline and derivatives thereof, polyquinoxaline and derivatives thereof, polyfluorene and derivatives thereof, and the like. Additionally, compounds described in JP-A No. 63-70257, JP-A No. 63-175860, JP-A No. 2-135359, JP-A No. 2-135361, JP-A No. 2-209988, JP-A No. 3-37992 and JP-A No. 3-152184 are also listed.

The content of the electron transporting material is preferably 1 to 500 parts by weight, more preferably 5 to 200 parts by weight, with respect to 100 parts by weight the polymer compound in the polymer composition.

The light emitting material includes low molecular weight fluorescent light emitting materials and phosphorescent light emitting materials, and the like. Examples of the light emitting material include naphthalene derivatives, anthracene and derivatives thereof, perylene and derivatives thereof, dyes such as polymethine dyes, xanthene dyes, coumarin dyes, cyanine dyes and the like, metal complexes having 8-hydroxyquinoline as a ligand, metal complexes having a 8-hydroxyquinoline derivative as a ligand, other fluorescent metal complexes, aromatic amines, tetraphenylcyclopentadiene and derivatives thereof, tetraphenylbutadiene and derivatives thereof, low molecular weight fluorescent materials such as stilbene compounds, silicon-containing aromatic compounds, oxazole compounds, furoxan compounds, thiazole compounds, tetraarylmethane compounds, thiadiazole compounds, pyrazole compounds, metacyclophane compounds, acetylene compounds and the like, metal complexes such as iridium complexes, platinum complexes and the like, triplet light emitting complexes. Additionally, compounds described in JP-A No. 57-51781, JP-A No. 59-194393 and the like are also listed.

The content of the light emitting material is 1 to 500 parts by weight, more preferably 5 to 200 parts by weight, with respect to 100 parts by weight of the polymer compound in the polymer composition. As the light emitting material, the light emitting material of the present invention is preferably used.

<Solution>

The polymer compound according to the present invention may also be dissolved or dispersed in an organic solvent to prepare a solution. This solution or dispersion is called an ink, a liquid composition or the like. The above-described solution may contain at least one material selected from the group consisting of hole transporting materials, electron transporting materials and light emitting materials, in addition to the polymer compound.

Here, the organic solvent includes chlorine-based solvents such as chloroform, methylene chloride, 1,2-dichloroethane, 1,1,2-trichloroethane, chlorobenzene, o-dichlorobenzene and the like; ether solvents such as tetrahydrofuran, dioxane and the like; aromatic hydrocarbon solvents such as toluene, xylene, trimethylbenzene, mesitylene and the like; aliphatic hydrocarbon solvents such as cyclohexane, methylcyclohexane, n-pentane, n-hexane, n-heptane, n-octane, n-nonane, n-decane and the like; ketone solvents such as acetone, methyl ethyl ketone, cyclohexanone and the like; ester solvents such as ethyl acetate, butyl acetate, methyl benzoate, ethyl cellosolve acetate and the like; polyhydric alcohols such as ethylene glycol, ethylene glycol monobutyl ether, ethylene glycol monoethyl ether, ethylene glycol monomethyl ether, dimethoxyethane, propylene glycol, diethoxymethane, triethylene glycol monoethyl ether, glycerin, 1,2-hexanediol and the like, and derivatives thereof; alcoholic solvents such as methanol, ethanol, propanol, isopropanol, cyclohexanol and the like; sulfoxide solvents such as dimethyl sulfoxide and the like; amide solvents such as N-methyl-2-pyrrolidone, N,N-dimethylformamide and the like, etc. These organic solvents may be used singly or in combination. Among these organic solvents, organic solvents having a structure containing a benzene ring and having a melting point of 0° C. or lower and a boiling point of 100° C. or higher are preferable since excellent viscosity and film formability are obtained.

According to the above-described solution, an organic film comprising the polymer compound according to the present invention can be produced easily. Specifically, an organic film comprising the polymer compound according to the present invention is obtained by coating the above-described solution on a substrate and distilling off an organic solvent by heating, pressure reduction and the like. The conditions for distilling off an organic solvent can be changed depending on the organic solvent to be used, and for example, it can be carried out under heating at about 50 to 150° C. and pressure reduction to about $10^{-3}$ Pa.

For the coating, use can be made of coating methods such as a spin coat method, a casting method, a microgravure method, a gravure coat method, a bar coat method, a roll coat method, a wire bar coat method, a dip coat method, a slit coat method, a capillary coat method, a spray coat method, a screen printing method, a flexo printing method, an offset printing method, an inkjet print method, a nozzle coat method and the like.

The suitable viscosity of the above-described solution varies depending on the printing method, and it is preferably 0.5 to 500 mPa·s at 25° C. When the above-described solution passes through a discharge apparatus such as in an inkjet print method, the viscosity at 25° C. is preferably 0.5 to 20 mPa·s, for preventing clogging and flying curving in discharging.

<Organic Film>

The organic film according to the present invention contains the polymer compound according to the present invention or the polymer composition according to the present invention. The organic film according to the present invention can be easily produced from the above-described solution as described above.

The organic film according to the present invention can be suitably used as a light emitting layer in a light emitting device described later. The organic film according to the present invention can be suitably used also in an organic semiconductor device. Since the organic film according to the present invention contains the above-described polymer compound, when the organic film is used as a light emitting layer of a light emitting device, the light emission efficiency of the light emitting device is significantly excellent.

<Organic Semiconductor Device>

By use of the organic film according to the present invention, an organic semiconductor device can also be fabricated. As the organic semiconductor device, organic film solar batteries and electric field effect type organic transistors are exemplified. Specifically, the above-described organic film is formed on a Si substrate carrying a gate electrode and an insulation film composed of $SiO_2$ and the like formed thereon, and a source electrode and a drain electrode are formed with Au and the like, thus, an electric field effect type organic transistor can be obtained.

<Light Emitting Device>

The light emitting device according to the present invention has the above-described organic film. In preferable embodiments, the light emitting device according to the present invention has an anode, a cathode, and a layer present between the anode and the cathode and comprising the above-described polymer compound. Here, the layer comprising the above-described polymer compound is preferably a layer composed of the above-described organic film, and it is preferable that this layer functions as a light emitting layer. A case in which the layer comprising the above-described polymer compound functions as a light emitting layer will be exemplified below as one preferable embodiment.

The constitution of the light emitting device according to the present invention includes the following structures (a) to (d). "/" denotes that before and after layers thereof are laminated adjacently (for example, "anode/light emitting layer" means that an anode and a light emitting layer are laminated adjacently.).

(a) anode/light emitting layer/cathode
(b) anode/hole transporting layer/light emitting layer/cathode
(c) anode/light emitting layer/electron transporting layer/cathode
(d) anode/hole transporting layer/light emitting layer/electron transporting layer/cathode The light emitting layer is a layer having a function of emitting light, the hole transporting layer is a layer having a function of transporting holes, and the electron transporting layer is a layer having a function of transporting electrons. The hole transporting layer and the electron transporting layer are collectively called a charge transporting layer in some cases. The hole transporting layer adjacent to the light emitting layer is called an interlayer layer in some cases.

Lamination and film formation of each layer can be carried out by using a solution comprising constituent components of each layer. For lamination and film formation from a solution, use can be made of coating methods such as a spin coat method, a casting method, a microgravure coat method, a gravure coat method, a bar coat method, a roll coat method, a wire bar coat method, a dip coat method, a slit coat method, a capillary coat method, a spray coat method, a screen printing method, a flexo printing method, an offset printing method, an inkjet print method, a nozzle coat method and the like.

The thickness of the light emitting layer may advantageously be selected so as to give suitable values of driving voltage and light emission efficiency, and is usually 1 nm to 1 μm, preferably 2 nm to 500 nm, further preferably 5 nm to 200 nm.

It is preferable that the hole transporting layer contains the hole transporting material described above. Though film formation of the hole transporting layer may be carried out by any methods, when the hole transporting material is a polymer compound, it is preferable that film formation is carried out from a solution comprising the hole transporting material and when the hole transporting material is a low molecular weight compound, it is preferable that film formation is carried out from a mixed solution comprising a polymer binder and the hole transporting material. As the film formation method, the same methods as the above-described coating methods can be used.

As the above-described polymer binder, those not extremely disturbing charge transportation and showing no strong absorption against visible light are preferable. The polymer binder includes polycarbonate, polyacrylate, polymethyl acrylate, polymethyl methacrylate, polystyrene, polyvinyl chloride, polysiloxane and the like.

The thickness of the hole transporting layer may advantageously be selected so as to give suitable values of driving voltage and light emission efficiency, and a thickness causing no formation of pin holes is necessary, and when the thickness is too large, the driving voltage of a device increases undesirably. Therefore, the thickness of the hole transporting layer is usually 1 nm to 1 μm, preferably 2 nm to 500 nm, further preferably 5 nm to 200 nm.

It is preferable that the electron transporting layer contains the electron transporting material described above. Though film formation of the electron transporting layer may be carried out by any methods, when the electron transporting material is a polymer compound, preferable are a method of film formation from a solution comprising the electron transporting material, a method of melting the electron transporting material to form a film, and the like. When the electron transporting material is a low molecular weight compound, preferable are a method of film formation by a vacuum vapor deposition method using a powder of the electron transporting material, a method of film formation from a solution comprising the electron transporting material, a method of melting the electron transporting material to form a film, and the like. As the method of film formation from a solution comprising the electron transporting material, the same methods as the above-described coating methods are exemplified. A polymer binder may also be contained in the solution.

As the above-described polymer binder, those not extremely disturbing charge transportation and showing no strong absorption against visible light are preferable. The polymer binder includes poly(N-vinylcarbazole), polyaniline and derivatives thereof, polythiophene and derivatives thereof, poly(p-phenylenevinylene) and derivatives thereof, poly(2,5-thienylenevinylene) and derivatives thereof, polycarbonate, polyacrylate, polymethyl acrylate, polymethyl methacrylate, polystyrene, polyvinyl chloride, polysiloxane and the like.

The thickness of the electron transporting layer may advantageously be selected so as to give suitable values of driving voltage and light emission efficiency, and a thickness causing no formation of pin holes is necessary, and when the thickness is too large, the driving voltage of a device increases undesirably. Therefore, the thickness of the electron transporting layer is usually 1 nm to 1 μm, preferably 2 nm to 500 nm, further preferably 5 nm to 200 nm.

Among charge transporting layers disposed adjacent to an electrode, those having a function of improving charge injection efficiency from an electrode and having an effect of lowering the driving voltage of a device are particularly called a charge injection layer (hole injection layer, electron injection layer) in some cases. For improving close adhesion with an electrode or improving charge injection from an electron, the above-described charge injection layer and an insulation layer may be disposed next to an electrode, and for improving close adhesion of an interface or preventing mixing, a thin buffer layer may be inserted into an interface of a charge transporting layer and a light emitting layer. The order and number of layers to be laminated, and the thickness of each layer may advantageously be selected in view of light emission efficiency and device life.

Light emitting devices having a charge injection layer include those having the following structures (e) to (p).
(e) anode/charge injection layer/light emitting layer/cathode
(f) anode/light emitting layer/charge injection layer/cathode
(g) anode/charge injection layer/light emitting layer/charge injection layer/cathode
(h) anode/charge injection layer/hole transporting layer/light emitting layer/cathode
(i) anode/hole transporting layer/light emitting layer/charge injection layer/cathode
(j) anode/charge injection layer/hole transporting layer/light emitting layer/charge injection layer/cathode
(k) anode/charge injection layer/light emitting layer/charge transporting layer/cathode
(l) anode/light emitting layer/electron transporting layer/charge injection layer/cathode
(m) anode/charge injection layer/light emitting layer/electron transporting layer/charge injection layer/cathode
(n) anode/charge injection layer/hole transporting layer/light emitting layer/charge transporting layer/cathode
(o) anode/hole transporting layer/light emitting layer/electron transporting layer/charge injection layer/cathode
(p) anode/charge injection layer/hole transporting layer/light emitting layer/electron transporting layer/charge injection layer/cathode The charge injection layer includes (I) a layer comprising an electric conductive polymer, (II) a layer disposed between an anode and a hole transporting layer and comprising a material having ionization potential of a value between an anode material in the anode and a hole transporting material in the hole transporting layer, (III) a layer disposed between a cathode and an electron transporting layer and comprising a material having electron affinity of a value between a cathode material in the cathode and an electron transporting material in the electron transporting layer; and the like.

When the charge injection layer is a layer comprising an electric conductive polymer, the electric conductivity of the electric conductive polymer is preferably $10^{-5}$ S/cm to $10^3$ S/cm, and for decreasing leak current between light emission picture elements, more preferably $10^{-5}$ S/cm to $10^2$ S/cm, particularly preferably $10^{-5}$ S/cm to $10^1$ S/cm. For satisfying such a range, the electric conductive polymer may be doped with a suitable amount of ions.

As the kind of ions to be doped, an anion is used in the case of a hole injection layer and a cation is used in the case of an electron injection layer. The anion includes a polystyrenesulfonic ion, an alkylbenzenesulfonic ion, a camphorsulfonic ion and the like, and the cation includes a lithium ion, a sodium ion, a potassium ion, a tetrabutylammonium ion and the like.

The thickness of the charge injection layer is preferably 1 to 100 nm, more preferably 2 to 50 nm.

The electric conductive polymer may advantageously be selected depending on a relation with the materials of an electrode and an adjacent layer, and includes electric conductive polymers such as polyaniline and its derivatives, polythiophene and its derivatives, polypyrrole and its derivatives, polyphenylenevinylene and its derivatives, polythienylenevinylene and its derivatives, polyquinoline and its derivatives, polyquinoxaline and its derivatives, polymers comprising an aromatic amine structure in the main chain or the side chain, and the like. The charge injection layer includes also layers comprising metal phthalocyanines (copper phthalocyanine and the like), carbon and the like.

The insulation layer has a function of making charge injection easy. The thickness of this insulation layer is usually 0.1 to 20 nm, preferably 0.5 to 10 nm, more preferably 1 to 5 nm. As the material used in the insulation layer, metal fluorides, metal oxides, organic insulating materials and the like are mentioned.

Light emitting devices having an insulation layer include those having the following structures (q) to (ab).
(q) anode/insulation layer/light emitting layer/cathode
(r) anode/light emitting layer/insulation layer/cathode
(s) anode/insulation layer/light emitting layer/insulation layer/cathode
(t) anode/insulation layer/hole transporting layer/light emitting layer/cathode
(u) anode/hole transporting layer/light emitting layer/insulation layer/cathode
(v) anode/insulation layer/hole transporting layer/light emitting layer/insulation layer/cathode
(w) anode/insulation layer/light emitting layer/electron transporting layer/cathode
(x) anode/light emitting layer/electron transporting layer/insulation layer/cathode
(y) anode/insulation layer/light emitting layer/electron transporting layer/insulation layer/cathode
(z) anode/insulation layer/hole transporting layer/light emitting layer/electron transporting layer/cathode
(aa) anode/hole transporting layer/light emitting layer/electron transporting layer/insulation layer/cathode
(ab) anode/insulation layer/hole transporting layer/light emitting layer/electron transporting layer/insulation layer/cathode It is preferable for the light emitting device according to the present invention to have a substrate next to an anode or a cathode. As the substrate, those showing no change in form and state in forming electrodes and layers are preferable, and substrates made of glass, plastic, polymer film, silicon and the like are mentioned. In the case of an opaque substrate, it is preferable that an electrode opposite to the electrode in contact with the substrate is transparent or semi-transparent.

In the light emitting device according to the present invention, it is usually preferable that at least one of electrodes consisting of an anode and cathode is transparent or semi-transparent, and the anode is transparent or semi-transparent.

As the material of the anode, an electric conductive metal oxide film, a semi-transparent metal film and the like are used. Specifically, films formed using electric conductive inorganic compounds such as indium oxide, zinc oxide, tin oxide, a composite oxide composed of indium.tin.oxide (ITO), a composite oxide composed of indium.zinc.oxide and the like, NESA and, gold, platinum, silver, copper and the like are used. As the anode, organic transparent electric conductive films made of polyaniline and derivatives thereof, polythiophene and derivatives thereof and the like may be used. For making charge injection easy, a layer made of a phthalocyanine derivative, an electric conductive polymer, carbon and the like or a layer made of a metal oxide, a metal fluoride, an organic insulation material and the like may be provided on the anode.

The anode fabrication method includes a vacuum vapor-deposition method, a sputtering method, an ion plating method, a plating method and the like.

The thickness of the anode can be selected in view of light transmission and electric conductivity, and it is usually 10 nm to 10 μm, preferably 20 nm to 1 μm, further preferably 50 nm to 500 nm.

As the cathode material, materials of small work function are preferable, and use is made of metals such as lithium, sodium, potassium, rubidium, cesium, beryllium, magnesium, calcium, strontium, barium, aluminum, scandium, vanadium, zinc, yttrium, indium, cerium, samarium, europium, terbium, ytterbium and the like, alloys comprising two or more of these metals, alloys comprising at least one of these metals and at least one of gold, silver, platinum, copper, manganese, titanium, cobalt, nickel, tungsten and tin, and graphite or graphite intercalation compounds, and the like.

As the cathode fabrication method, a vacuum vapor-deposition method, a sputtering method, a lamination method of thermally press-binding a metal film, and the like are used.

The thickness of the cathode can be selected in view of electric conductivity and durability, and it is usually 10 nm to 10 μm, preferably 20 nm to 1 μm, further preferably 50 nm to 500 nm.

A layer made of an electric conductive polymer, or a layer made of a metal oxide, a metal fluoride, an organic insulation material and the like, may be provided between a cathode and a light emitting layer or between a cathode and an electron transporting layer, and after fabrication of a cathode, a protective layer for protecting the light emitting device may be installed. For use of the light emitting device stably for a long period of time, it is preferable to install a protective layer and/or a protective cover, for protecting the device from outside.

As the protective layer, resins, metal oxides, metal fluorides, metal borides and the like can be used. As the protective cover, a glass plate, and a plastic plate having a surface which has been subjected to low water permeation treatment, and the like can be used, and a method in which the protective cover is pasted to a device substrate with a thermosetting resin or a photo-curing resin to attain sealing is suitably used. When a space is kept using a spacer, blemishing of a device can be prevented easily. If an inert gas such as nitrogen, argon and the like is filled in this space, oxidation of a cathode can be prevented, further, by placing a drying agent such as barium oxide and the like in this space, it becomes easy to suppress moisture adsorbed in a production process from imparting damages to the device.

A light emitting device comprising the polymer compound according to the present invention or the polymer composition according to the present invention is useful for surface light sources such as curved light sources, flat light source and the like (for example, illumination and the like); displays such as segment displays, dot matrix displays (for example, dot matrix flat display and the like), liquid crystal displays (for example, liquid crystal display, liquid crystal display backlight and the like), etc. The polymer compound according to the present invention is suitable as the material used for fabrication of these devices, and additionally, is useful also as laser dyes, organic solar battery materials, materials for conductive films such as organic transistor organic semiconductors, electric conductive films, organic semiconductor films and the like, materials of luminous films emitting fluorescence, materials of polymer electric field effect transistors, and the like.

For obtaining light emission in the form of plane using the light emitting device according to the present invention, it may be advantages to place a planar anode and a planar cathode so as to overlap. For obtaining light emission in the form of pattern, there are a method in which a mask having a window in the form of pattern is placed on the surface of the above-mentioned surface light emitting device, and a method in which either an anode or a cathode, or both electrodes are formed in the form pattern. By forming a pattern by any of these methods, and placing several electrodes so that on/off is independently possible, a segment display is obtained which can display digits, letters, simple marks and the like. Further, for providing a dot matrix display, it may be permissible that both an anode and a cathode are formed in the form of stripe, and placed so as to cross. By using a method in which several polymer compounds showing different emission colors are painted separately or a method in which a color filter or a fluorescence conversion filter is used, partial color display and multi-color display are made possible. In the case of a dot matrix display, passive driving is possible, and active driving may be carried out in combination with TFT and the like. These displays can be used for computers, televisions, portable terminals, cellular telephones, car navigations, video camera view finders, and the like.

EXAMPLES

Examples will be shown below for illustrating the present invention further in detail, but the present invention is not limited to them.

The polystyrene-equivalent number average molecular weight and weight average molecular weight of a polymer compound were measured under the following measurement conditions using gel permeation chromatography (GPC) (manufactured by Shimadzu Corporation, trade name: LC-10 Avp).

[Measurement Conditions]

A polymer compound to be measured was dissolved in tetrahydrofuran (THF) so as to give a concentration of about 0.05 wt %, and the solution was injected in an amount of 10 μL into GPC. Tetrahydrofuran was used as the mobile phase of GPC, and allowed to flow at a flow rate of 2.0 ml/min. As the column, PLgel MIXED-B (manufactured by Polymer Laboratories Ltd.) was used. As the detector, a differential refractive index detector (manufactured by Shimadzu Corp., trade name: RID-10A) was used.

Example 1

Synthesis of Compound 2

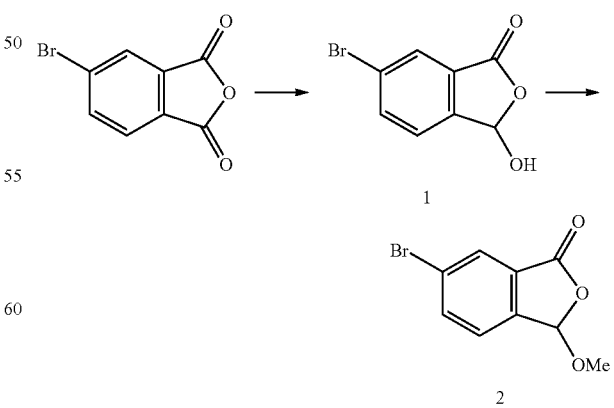

Into a 1 L four-necked recovery flask was charged 23.2 g (100.2 mmol) of 4-bromophthalic anhydride, and dissolved in THF (430 ml), then, a gas in the flask was purged with nitrogen. The temperature in the flask was decreased to −66° C., then, a lithium tri(tert-butoxy)aluminum hydride solution (100.2 ml, 100.2 mmol, 1.0M THF solution) was dropped. The reaction solution was stirred for 2 hours at −65° C. or lower, then, water (100 ml) and dilute hydrochloric acid (400 ml) were added. The reaction solution was separated, the aqueous layer was extracted with ethyl acetate (400 ml) twice, then, the organic layer was dried over anhydrous sodium sulfate, filtrated, and concentrated to obtain 23.5 g of a compound 1 as a white solid.

Into a 300 ml recovery flask was charged 23.5 g of the compound 1, dissolved in methanol (232 ml), then, a gas in the flask was purged with nitrogen. The resultant solution was heated at 80° C. for 6 hours. Thereafter, it was left to cool to obtain a solution which was then concentrated, and ethyl acetate (100 ml) and water (100 ml) were added to cause liquid separation. Further, the aqueous layer was extracted with ethyl acetate (100 ml). Next, the organic layer was washed with saturated saline (100 ml), then, the organic layer was dried over anhydrous sodium sulfate, filtrated, and concentrated to obtain 20.3 g of a compound 2 as a pale yellow oil.

Synthesis of Compound 3

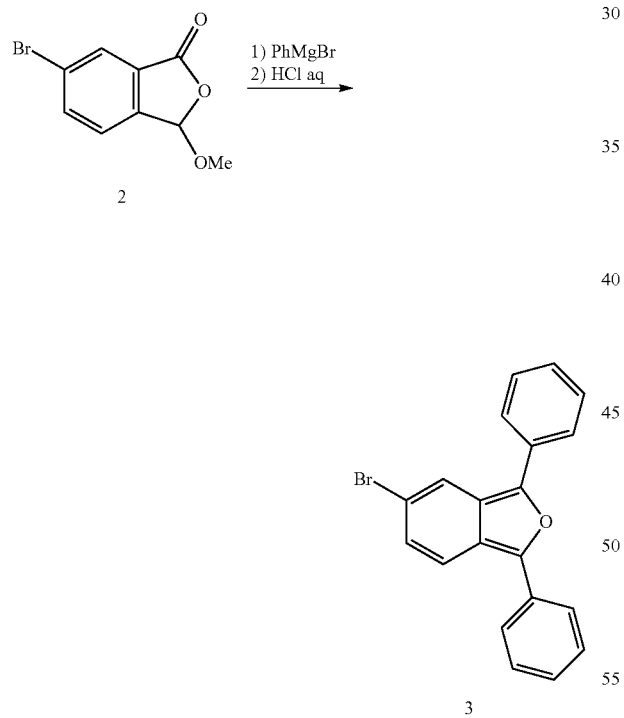

Into a 1 L four-necked recovery flask was charged the compound 2 (16.2 g), dissolved in THF (267 ml), then, a gas in the flask was purged with nitrogen. The resultant solution was cooled down to 0° C., then, phenylmagnesium bromide (110.0 ml, 1.0M THF solution) was dropped, and the mixture was left for 3 hours at this temperature, then, dilute hydrochloric acid (200 ml) was dropped. The reaction solution was liquid-separated, the aqueous layer was extracted with ethyl acetate (300 ml) twice, then, the organic layer was washed with water. The organic layer was dried over anhydrous sodium sulfate, filtrated, and concentrated to obtain 22.1 g of a compound 3.

Synthesis of Compound 5

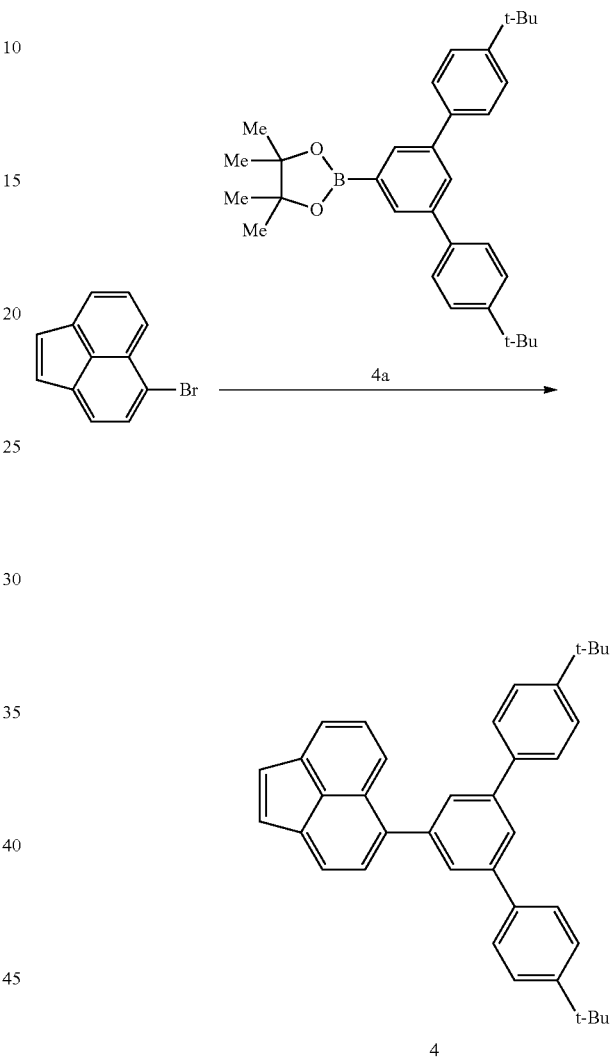

Under an argon atmosphere, into a 1 L three-necked flask were added 5-bromoacenaphthylene (10 g), a compound 4a (17.2 g), dichlorobis(triphenylphosphine)palladium (2.1 g) and toluene (550 ml), and the mixture was stirred and bubbled with argon for 10 minutes. To this were added 140 ml of a 2M potassium hydroxide aqueous solution and tetrabutylammonium bromide (0.6 mg), and the mixture was heated and stirred at 100° C. for 90 minutes. The temperature of the reaction solution was returned to room temperature, to stop the reaction. The aqueous layer was removed from the resultant solution, then, washed with 150 ml of water three times, and dehydrated with saturated saline. To this was added sodium sulfate to cause drying, then, the mixture was filtrated. After filtration, the resultant solution was concentrated under reduced pressure, then, purified by silica gel column chromatography using hexane/chloroform as a developing solvent, to obtain a compound 4 (13.5 g) as an orange powder.

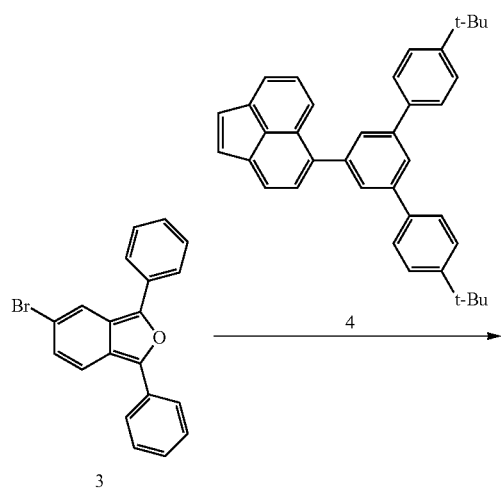

3

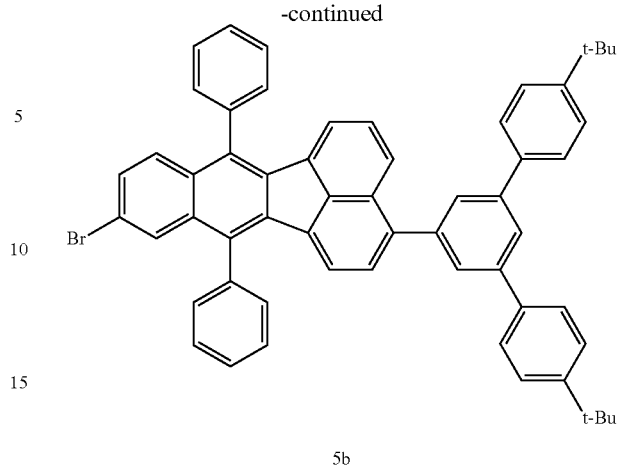

5b

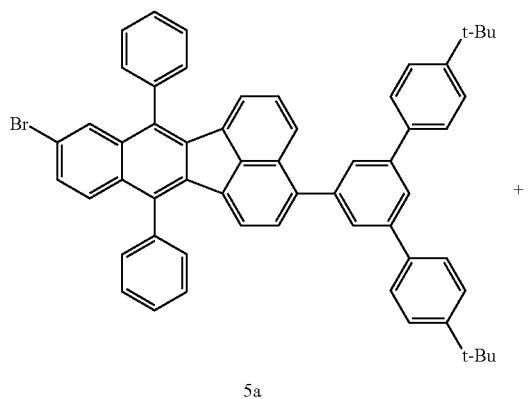

5a

The compound 3 (3.3 g), the compound 4 (5.0 g) and xylene (30 ml) were charged, and the mixture was heated in an oil bath of 150° C. for 2 hours. Thereafter, 0.54 g of p-TsOH was added to the reaction solution at 110° C., and the mixture was heated and stirred at this temperature for 2 hours. Then, after cooling down to room temperature, toluene and water were added and the mixture was stirred, liquid-separated and extracted to obtain an organic layer. This organic layer was washed with a 5 wt % sodium chloride aqueous solution and water, then, dried over anhydrous magnesium sulfate, concentrated and dried to give a solid. The resultant product was separated and purified by silica gel column chromatography (hexane/chloroform), to obtain 1.8 g of a compound 5 (mixture of compound 5a and compound 5b) (yellow-orange crystal).

LC-MS (APCI, positive): [M+H]$^+$823

Synthesis of Compound 6

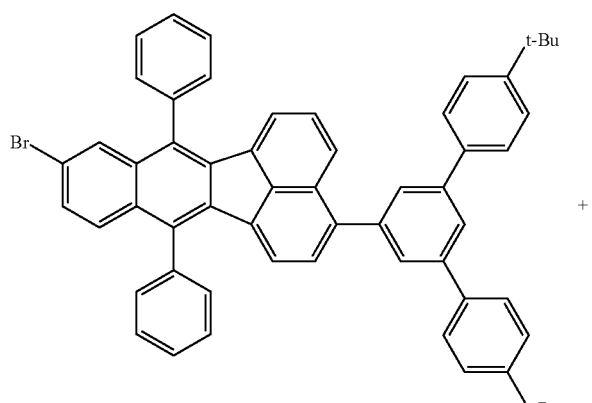

5a

-continued
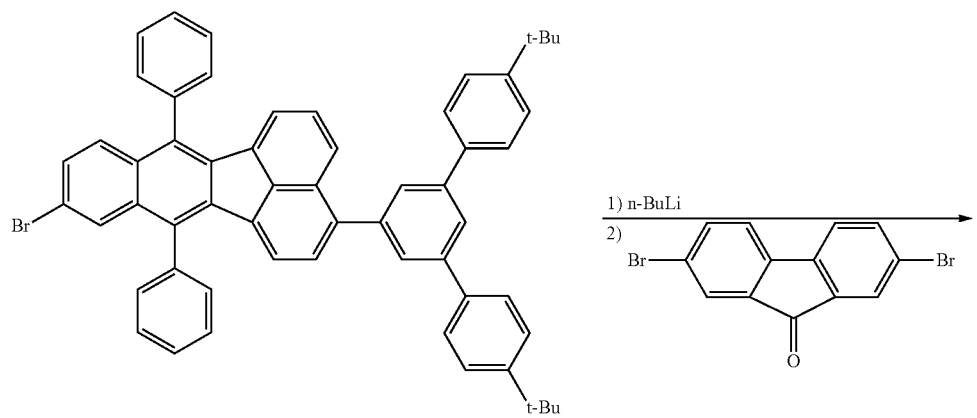
5b
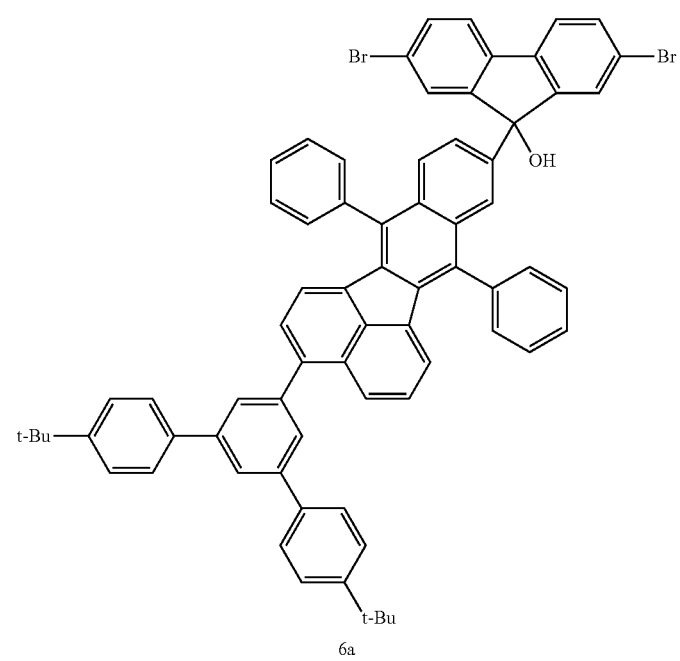
6a

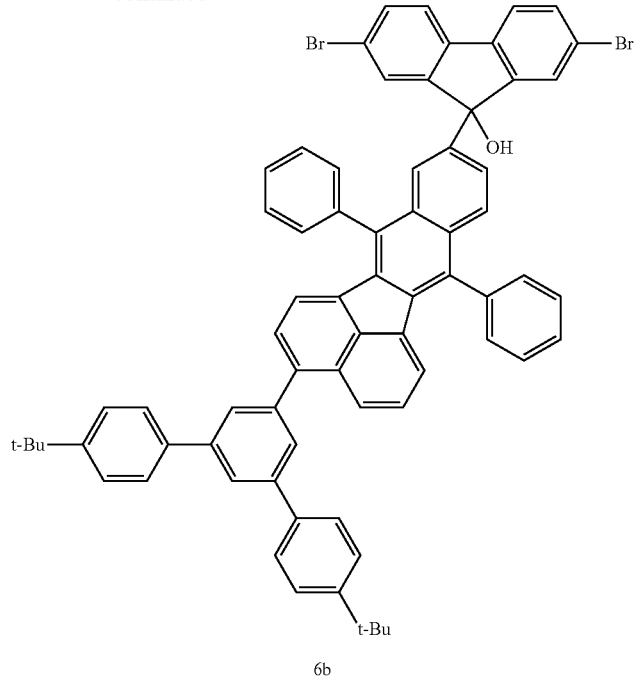 [SMILES: CC(C)(C)c1ccc(-c2cc(-c3ccc(C(C)(C)C)cc3)cc(-c3ccc4c5c(cccc35)-c3c-4c(-c4ccccc4)c4cc(C5(O)c6cc(Br)ccc6-c6ccc(Br)cc65)ccc4c3-c3ccccc3)c2)cc1]

6b

The compound 5 (3.2 g) was charged into a 100 ml glass vessel, then, an atmosphere in the vessel was purged with argon, and 18 ml of THF was dropped. Thereafter, the mixture was cooled to −70° C. or lower by a dry ice-acetone bath, and 1.39 ml of a 2.76M n-butyllithium/hexane solution was dropped over a period of about 10 minutes. Stirring thereof was continued under this condition for 30 minutes, then, a mixture of 1.23 g of 2,7-dibromofluorenone and 18 ml of THF was dropped over a period of 30 minutes. During dropping, the reaction solution changed from dark red-brown color to red color, and red-orange transparent liquid was obtained after one hour of the reaction. Thereafter, water was dropped into the reaction solution, and the mixture was extracted with toluene. The resultant organic layer was washed with water twice, then, dried over anhydrous magnesium sulfate, filtrated to obtain a solution which was then concentrated and dried to give a solid. The resultant product was separated and purified by silica gel column chromatography (hexane/toluene), to obtain 3.0 g of a compound 6 (mixture of compound 6a and compound 6b)(yellow-orange powder).

LC-MS (API-ES (ESI-KCl), positive): [M+K]$^+$ 1121

Synthesis of Compound 7

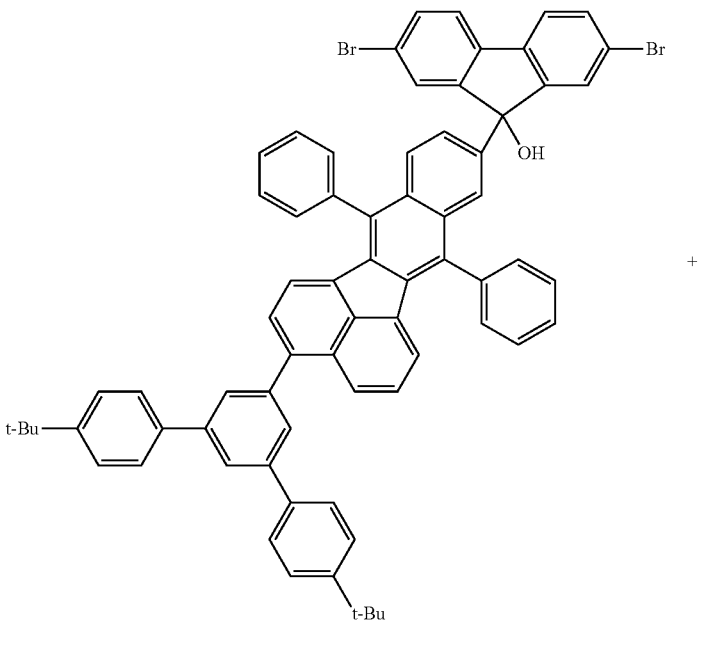

6a

+

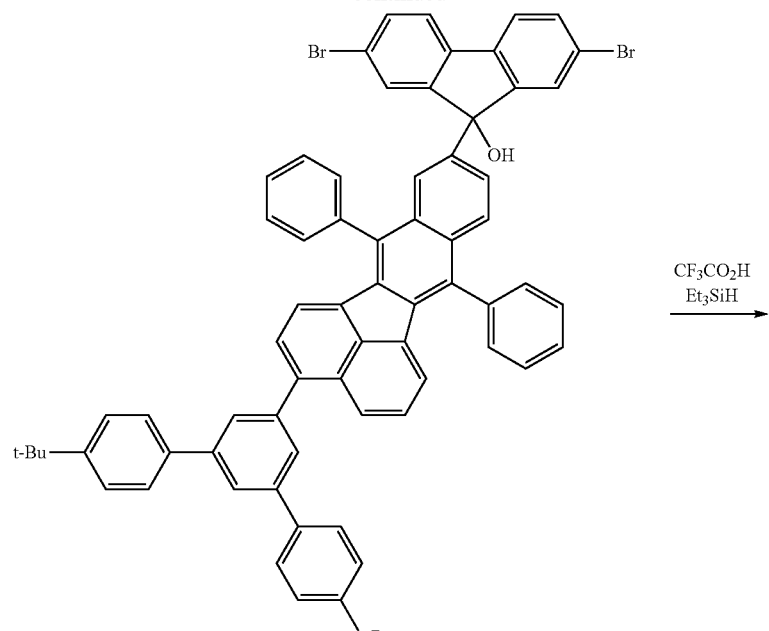
6b
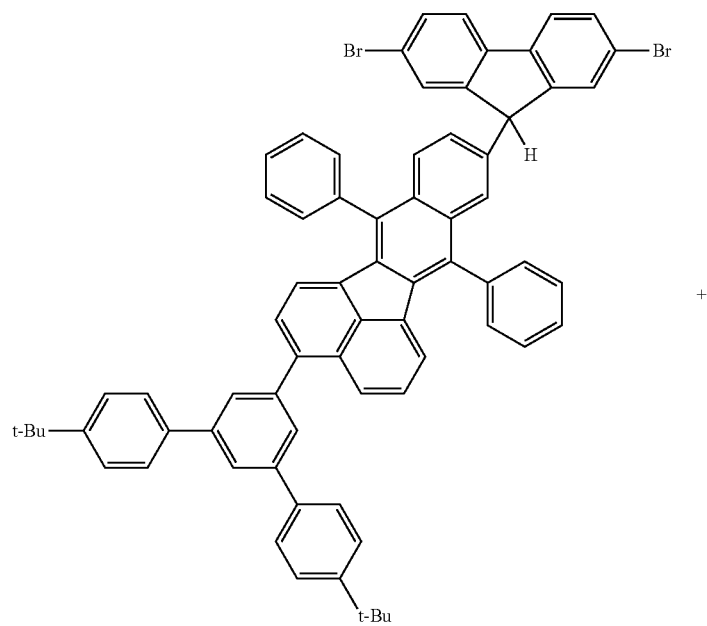
7a

-continued

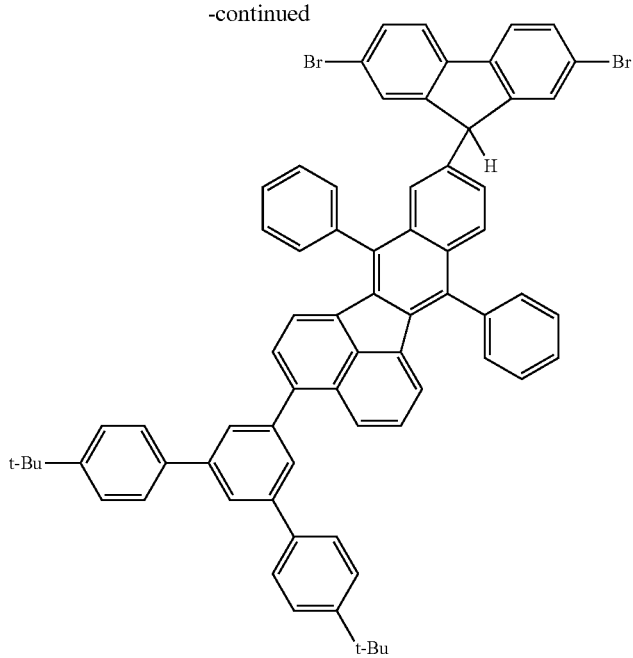

7b

The compound 6 (2.8 g) was charged into a 200 ml glass vessel then, an atmosphere in the vessel was purged with argon, and 54 ml of cyclohexane was dropped. Thereafter, 1.25 ml of triethylsilane was dropped into the reaction solution over a period of about 10 minutes at room temperature, and into this, 3.9 ml of trifluoroacetic acid was dropped over a period of about 30 minutes. Two hours after, water was dropped into this, and the mixture was extracted with 300 ml of chloroform and 300 ml of toluene. The resultant organic layer was washed with a 5 wt % dipotassium hydrogen phosphate aqueous solution and water, then, dried over anhydrous magnesium sulfate, filtrated to obtain a solution which was then concentrated and dried to obtain 2.8 g of a compound 7 (mixture of compound 7a and compound 7b) (pale brown solid).

LC-MS (APCI, negative): [M−H]− 1065

Synthesis of Compound 8

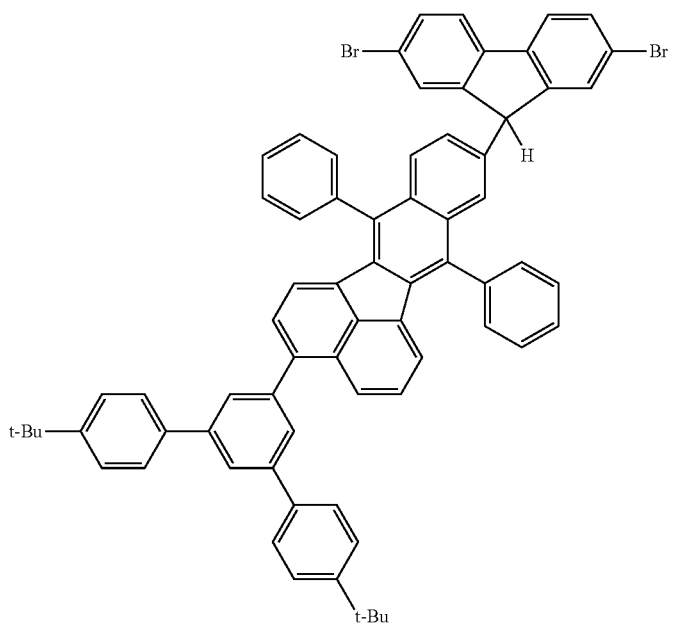

7a

+

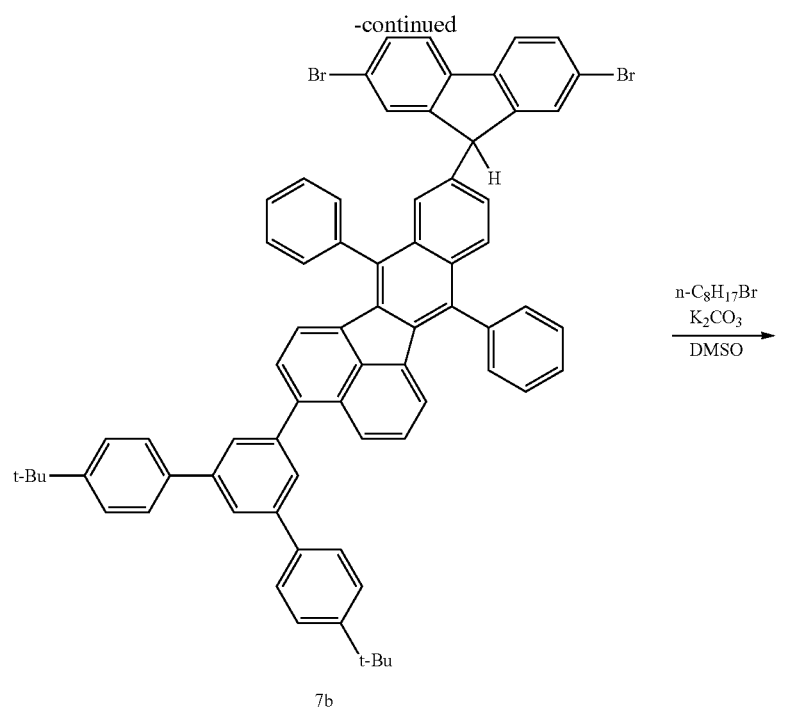
7b
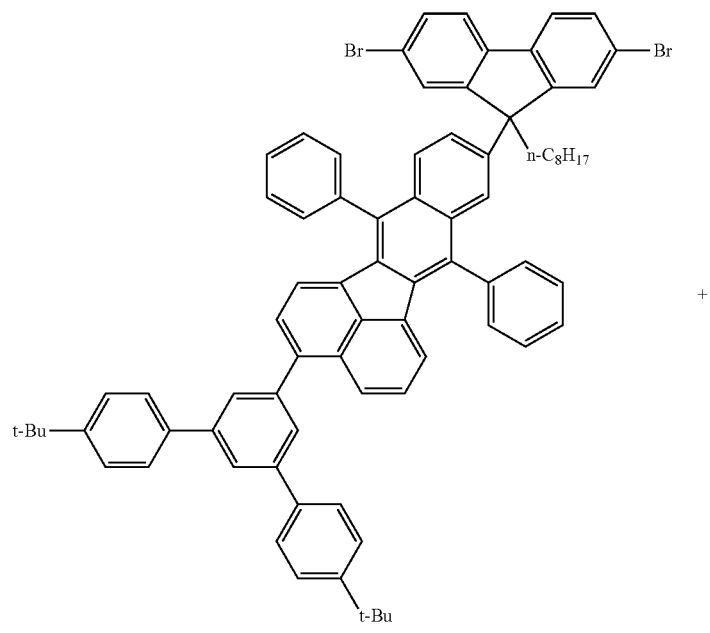
8a

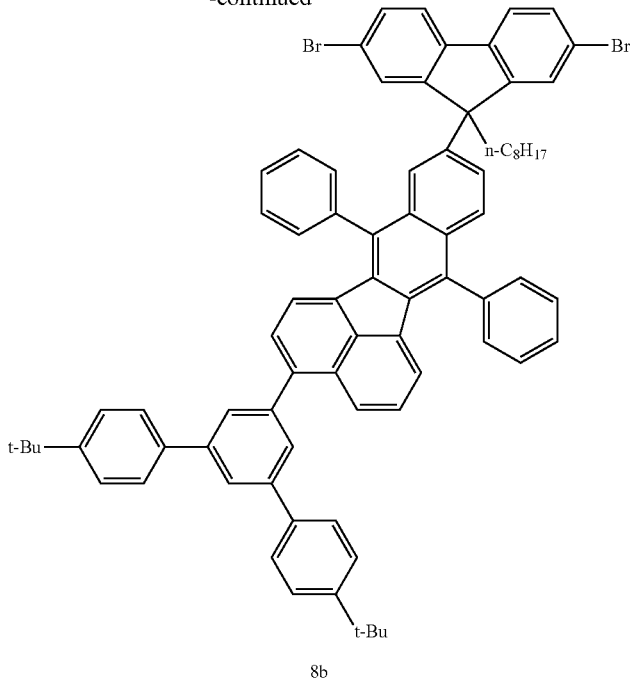

8b

The compound 7 (1.40 g) and 0.91 g of potassium carbonate were charged into a 50 ml glass vessel, then, an atmosphere in the vessel was purged with argon, and 1.01 g of n-octyl bromide, 21 ml of dimethyl sulfoxide (DMSO) and 9.6 ml of toluene were dropped. Thereafter, the above-described vessel was heated to around 115° C. Before heating, the reaction solution was a dark blue solution, however, after 30 minutes of heating, blue color disappeared to give a pale brown reaction solution. Further, the mixture was heated and stirred at 115 to 120° C. for 1 hour, then, cooled down to around room temperature. Thereafter, water was dropped into the reaction solution and the mixture was extracted with toluene, and washed with a 5 wt % sodium chloride aqueous solution and water, then, dried over anhydrous magnesium sulfate, filtrated to obtain a solution which was then concentrated and dried to give a solid. The resultant product was separated and purified by silica gel column chromatography, to obtain 1.2 g of a compound 8 (mixture of compound 8a and compound 8b) (yellow solid). According to H-NMR, the presence ratio (molar ratio) of the compound 8a to the compound 8b in the mixture was about 50:50.

LC-MS (API-ES (ESI-KCl), positive): [M+K]$^+$ 1217

Example 2

Synthesis of Compound 11

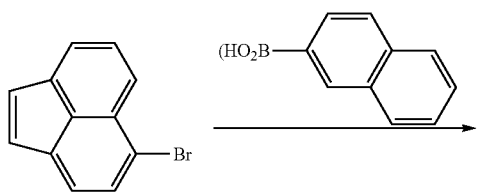

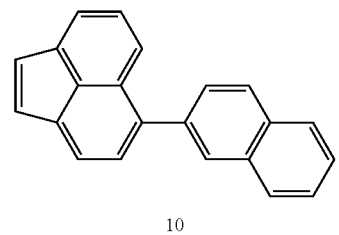

10

Under an argon atmosphere, into a 500 ml four-necked flask were added 5-bromoacenaphthylene (18 g), 2-naphthaleneboronic acid (14.7 g), tetrakistriphenylphosphine-palladium (2.6 g), 260 ml of toluene and 70 ml of ethanol, and the mixture was stirred, and bubble with argon for 10 minutes. To this was added 82.6 g of a 25 wt % sodium carbonate aqueous solution, and the mixture was heated and stirred at 100° C. for 120 minutes. The temperature of the reaction solution was returned to room temperature, to stop the reaction. The aqueous layer was removed from the resultant solution, then, washed with distilled water (150 ml) three times, and dehydrated with saturated saline. To this were added magnesium sulfate and 2 g of activated carbon, then, the mixture was filtrated. After filtration, the resultant solution was concentrated under reduced pressure, then, purified by silica gel column chromatography using hexane/ethyl acetate as a developing solvent, to obtain a compound 10 (21.8 g) as an orange powder.

113

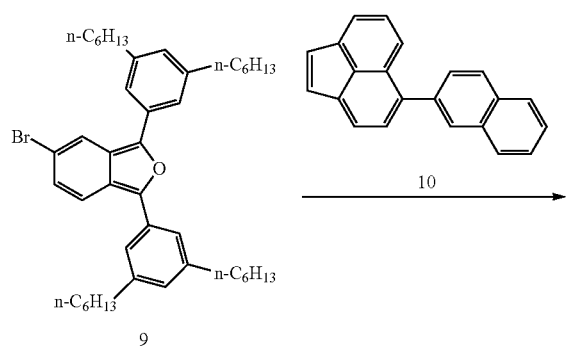

9

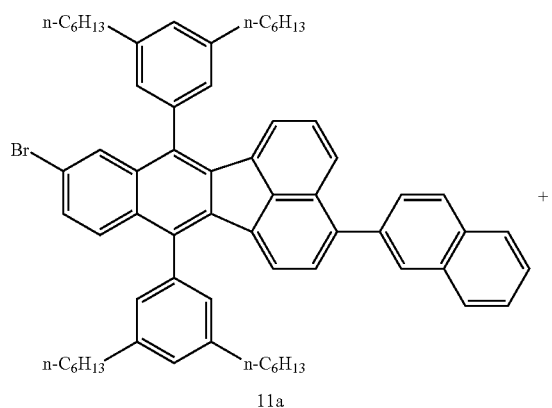

11a

114

-continued

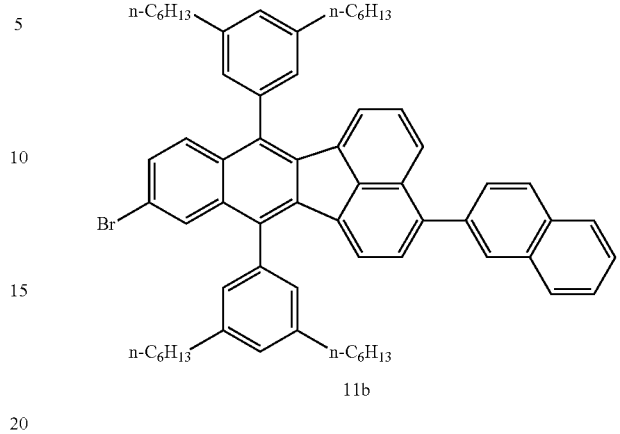

11b

The compound 9 (2.2 g), the compound 10 (1.0 g) and 10 ml of xylene were charged, and the mixture was heated by an oil bath of 150° C. for 2 hours. Thereafter, 0.11 g of p-TsOH was added to this at 110° C., and the mixture was heated and stirred at this temperature for 2 hours. Thereafter, the mixture was cooled down to room temperature, and toluene and water were added and the mixture was stirred, then, liquid-separated and extracted to obtain an organic layer. This organic layer was washed with a 5 wt % sodium hydrogen carbonate aqueous solution and water, dried over anhydrous magnesium sulfate, and concentrated and dried to give a solid. The resultant product was separated and purified by silica gel column chromatography (hexane/chloroform), to obtain 1.6 g of a compound 11 (mixture of compound 11a and compound 11b) (yellow-red oil).

LC-MS (APCI, positive): [M+H]$^+$ 946

Synthesis of Compound 12

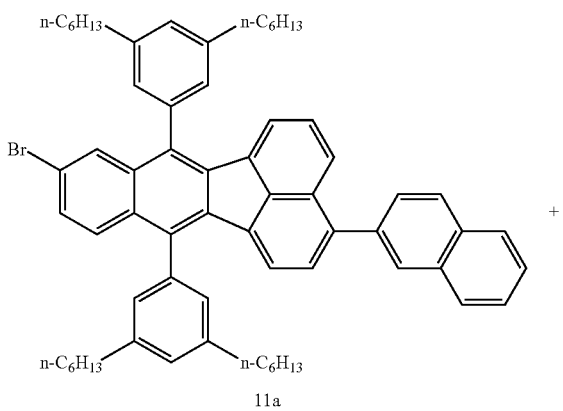

11a

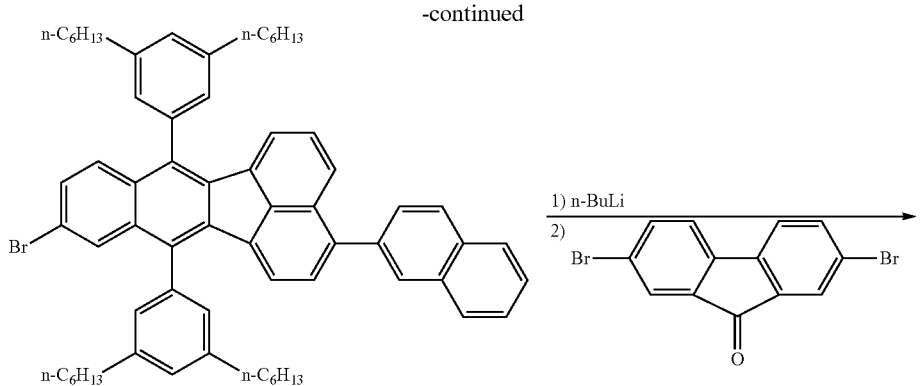

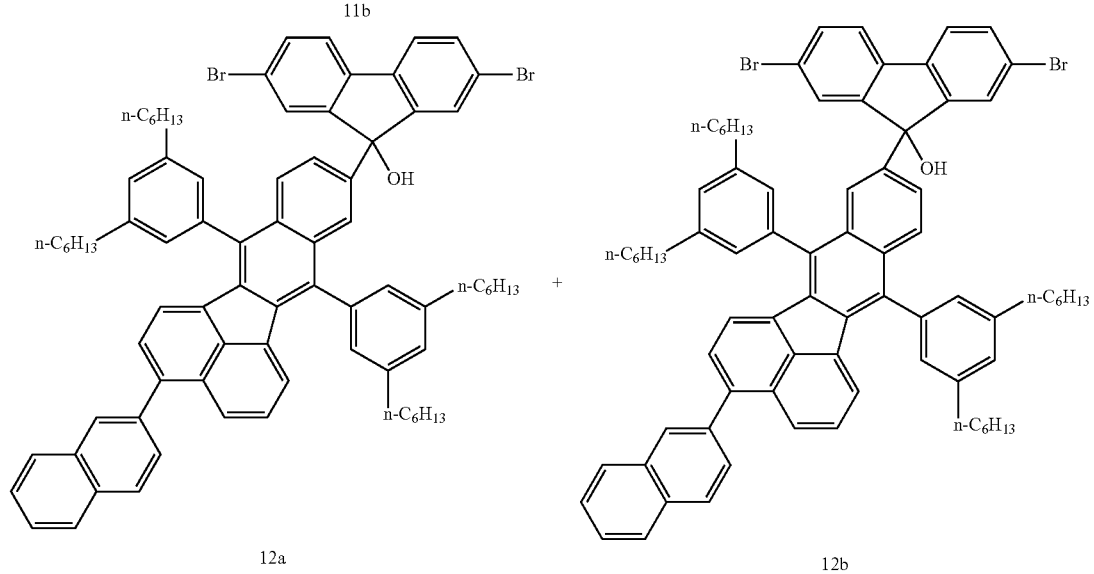

The compound 11 (4.05 g) was charged into a 100 ml glass vessel, then, an atmosphere in the vessel was purged with argon, and 23 ml of THF was dropped. Thereafter, the reaction solution was cooled to −70° C. or lower by a dry ice-acetone bath, and 1.6 ml of a 2.76M n-butyllithium/hexane solution was dropped over a period of about 10 minutes. Stirring thereof was continued under this condition for 10 minutes, then, a mixture of 1.45 g of 2,7-dibromofluorenone and 18 ml of THF was dropped into this over a period of 10 minutes. The mixture was further stirred for 10 minutes, then, heated up to 0° C., water was dropped and the mixture was extracted with toluene. The resultant organic layer was washed with water twice, then, dried over anhydrous magnesium sulfate, filtrated to obtain a solution which was then concentrated and dried to give a solid. The resultant product was separated and purified by silica gel column chromatography (hexane/toluene), to obtain 3.6 g of a compound 12 (mixture of compound 12a and compound 12b)(yellow oil).

LC-MS (APCI, positive): [M−OH]$^+$ 1187

Synthesis of Compound 13

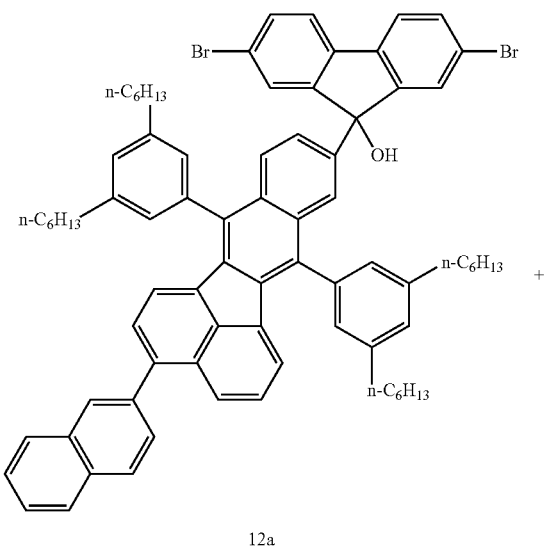

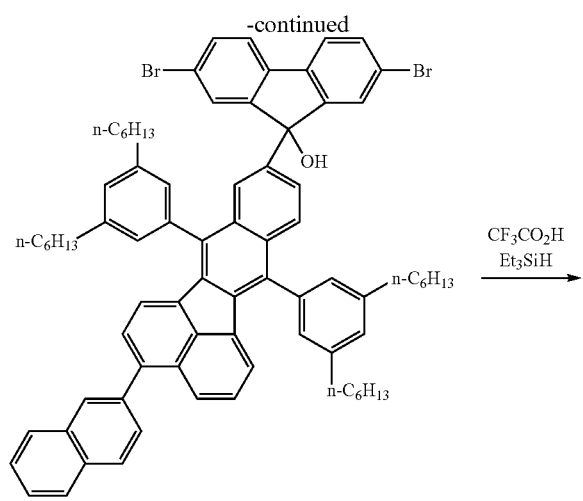

triethylsilane was dropped over a period of about 2 minutes, and into this, 10.7 ml of trifluoroacetic acid was dropped over a period of about 10 minutes. The mixture was stirred for 2 hours, then, water was dropped into this and the mixture was extracted with hexane. The resultant organic layer was washed with a 5 wt % dipotassium hydrogen phosphate aqueous solution and water, then, dried over anhydrous magnesium sulfate, filtrated to obtain a solution which was then concentrated and dried to give a solid, and the product was separated and purified by silica gel column chromatography (hexane/chloroform), to obtain 4.7 g of a compound 13 (mixture of compound 13a and compound 13b) (yellow oil).

Synthesis of Compound 14

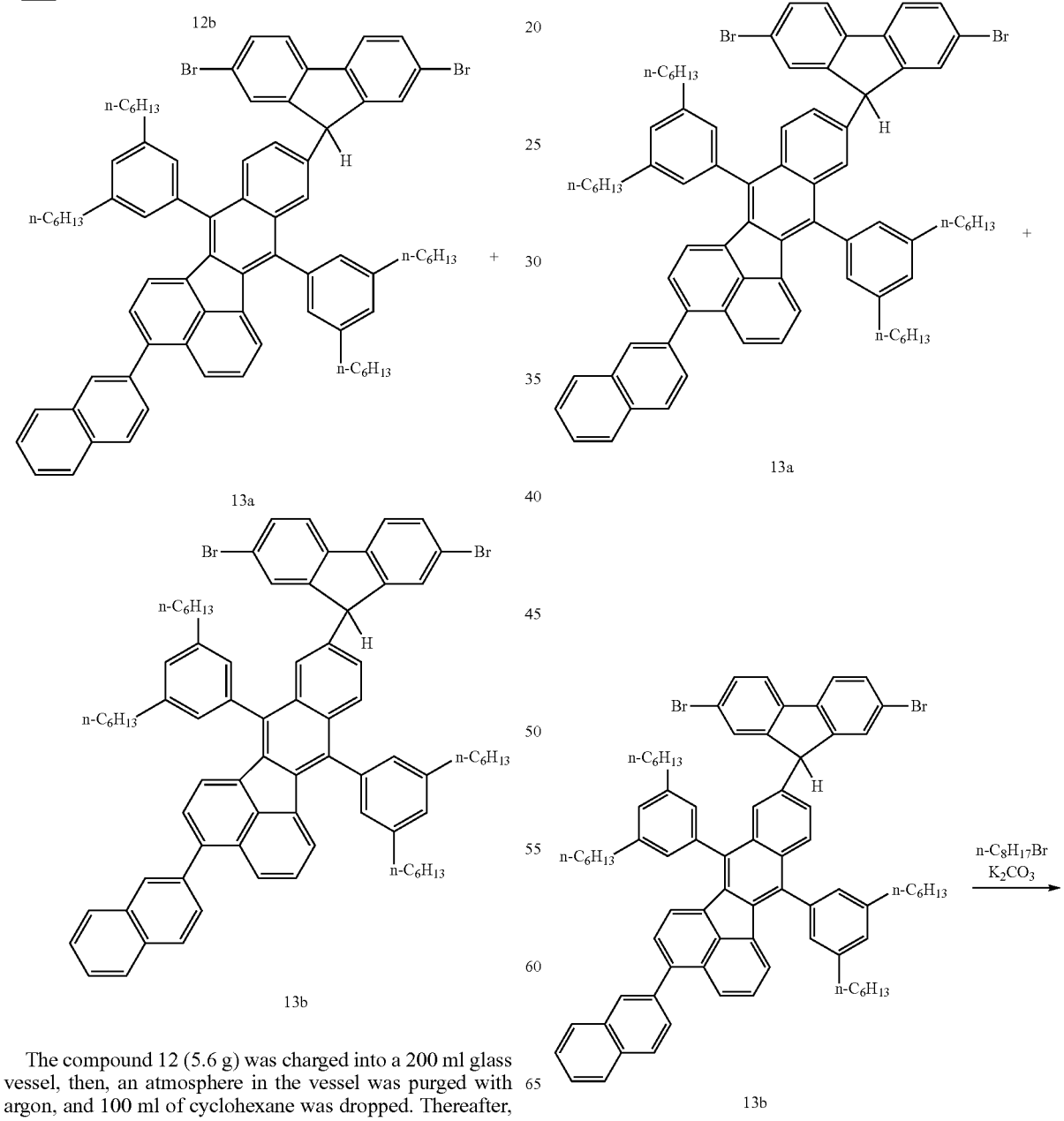

The compound 12 (5.6 g) was charged into a 200 ml glass vessel, then, an atmosphere in the vessel was purged with argon, and 100 ml of cyclohexane was dropped. Thereafter, the reaction solution was cooled to 5 to 10° C., and 2.3 ml of -continued

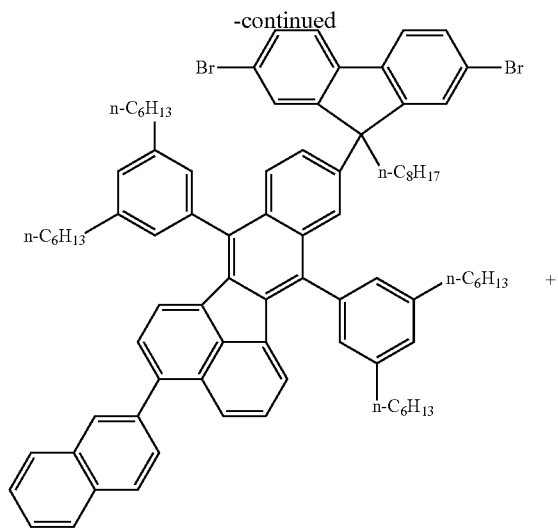

14a

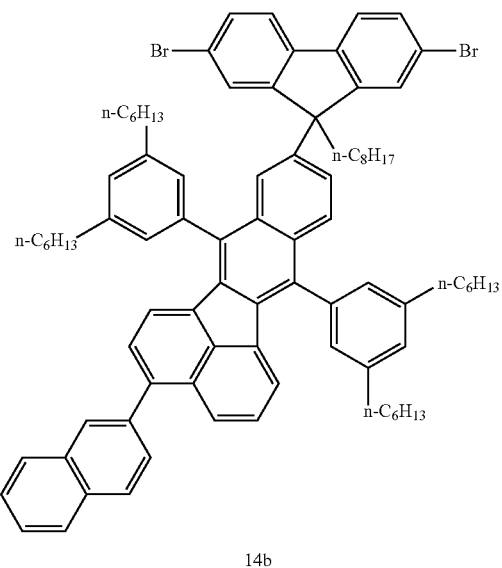

14b

The compound 13 (0.22 g) and 0.13 g of potassium carbonate were charged into a 50 ml glass vessel, then, an atmosphere in the vessel was purged with argon, and 0.14 g of n-octyl bromide, 3 ml of DMSO and 1.5 ml of toluene were dropped. Thereafter, the reaction solution was heated up to around 115° C. Before heating, the reaction solution was a dark blue solution, however, after 30 minutes of heating, blue color disappeared to give a pale brown reaction solution. The reaction solution was heated and stirred at 115 to 120° C. for 1 hour, then, cooled down to around room temperature. Thereafter, water was dropped into this and the mixture was extracted with toluene, and washed with a 5 wt % sodium hydrogen carbonate aqueous solution and water, then, dried over anhydrous magnesium sulfate, filtrated to obtain a solution which was then concentrated and dried to give a solid. The resultant product was separated and purified by silica gel column chromatography (hexane/chloroform), to obtain 0.16 g of a compound 14 (mixture of compound 14a and compound 14b) (yellow solid). According to H-NMR, the presence ratio (molar ratio) of the compound 14a to the compound 14b in the mixture was about 50:50.

LC-MS (APCI, positive): [M]+ 1302

Example 3

Synthesis of Polymer Compound A

Under an argon atmosphere, a compound (0.163 g, 0.20 mmol) represented by the following formula:

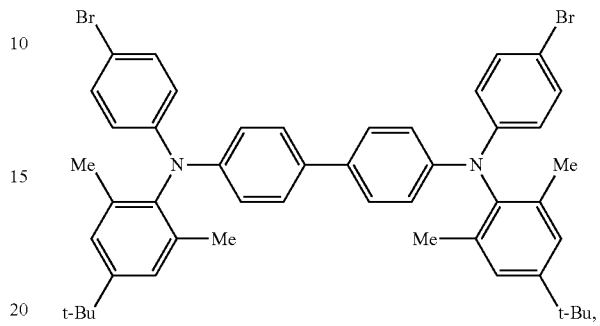

a compound (0.360 g, 0.56 mmol) represented by the following formula:

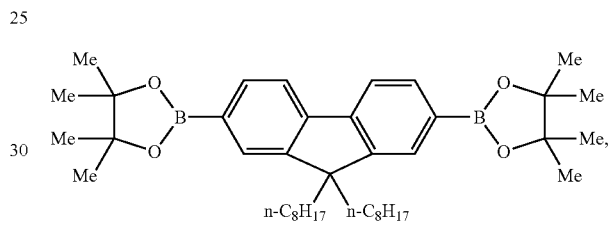

a compound (1.064 g, 1.44 mmol) represented by the following formula:

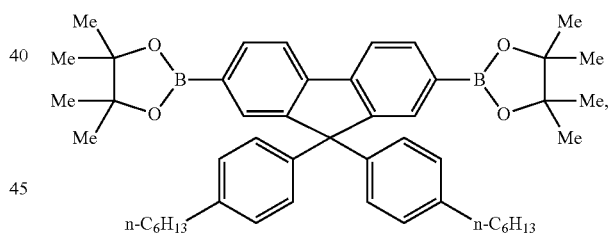

a compound (1.031 g, 1.60 mmol) represented by the following formula:

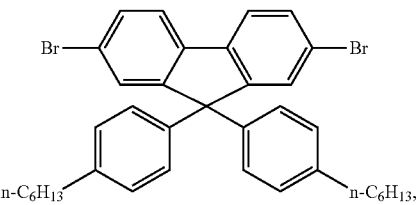

the compound 8 (0.236 g, 0.20 mmol), dichlorobis(triphenylphosphine)palladium (1.4 mg) and toluene (50 ml) were mixed, and heated at 105° C. Into the resultant solution, a 20 wt % tetraethylammonium hydroxide aqueous solution (6.6 ml) was dropped, and the mixture was refluxed for 2 hours and 40 minutes. After the reaction, to this were added phenylboric acid (24.4 mg) and toluene (5 ml), and the mixture was further refluxed for 18.5 hours. Then, to this was added a sodium diethyldithiacarbamate aqueous solution, and the mixture was stirred at 80° C. for 2 hours. After cooing, the organic layer was washed with water (26 ml) twice, a 3 wt % acetic acid aqueous solution (26 ml) twice and water (26 ml) twice, and the resultant solution was dropped into methanol (400 ml), and filtrated to obtain a precipitate. The precipitate was dissolved in toluene (80 ml), and purified by passing through an alumina column and a silica gel column in this order. The resultant solution was dropped into methanol (400 ml), stirred, then, the resultant precipitate was filtrated, and dried, to obtain 1.47 g of a polymer (hereinafter, referred to as "polymer compound A") comprising a constitutional unit represented by the following formula (K-1)(presence ratio (molar ratio) of two constitutional units is approximately 50:50), a constitutional unit represented by the following formula (K-2), a constitutional unit represented by the following formula (K-3) and a constitutional unit represented by the following formula (K-4) at a molar ratio of 5:14:5:76.

The polymer compound A had a polystyrene-equivalent number-average molecular weight of $8.5 \times 10^4$ and a polystyrene-equivalent weight-average molecular weight of $2.39 \times 10^5$.

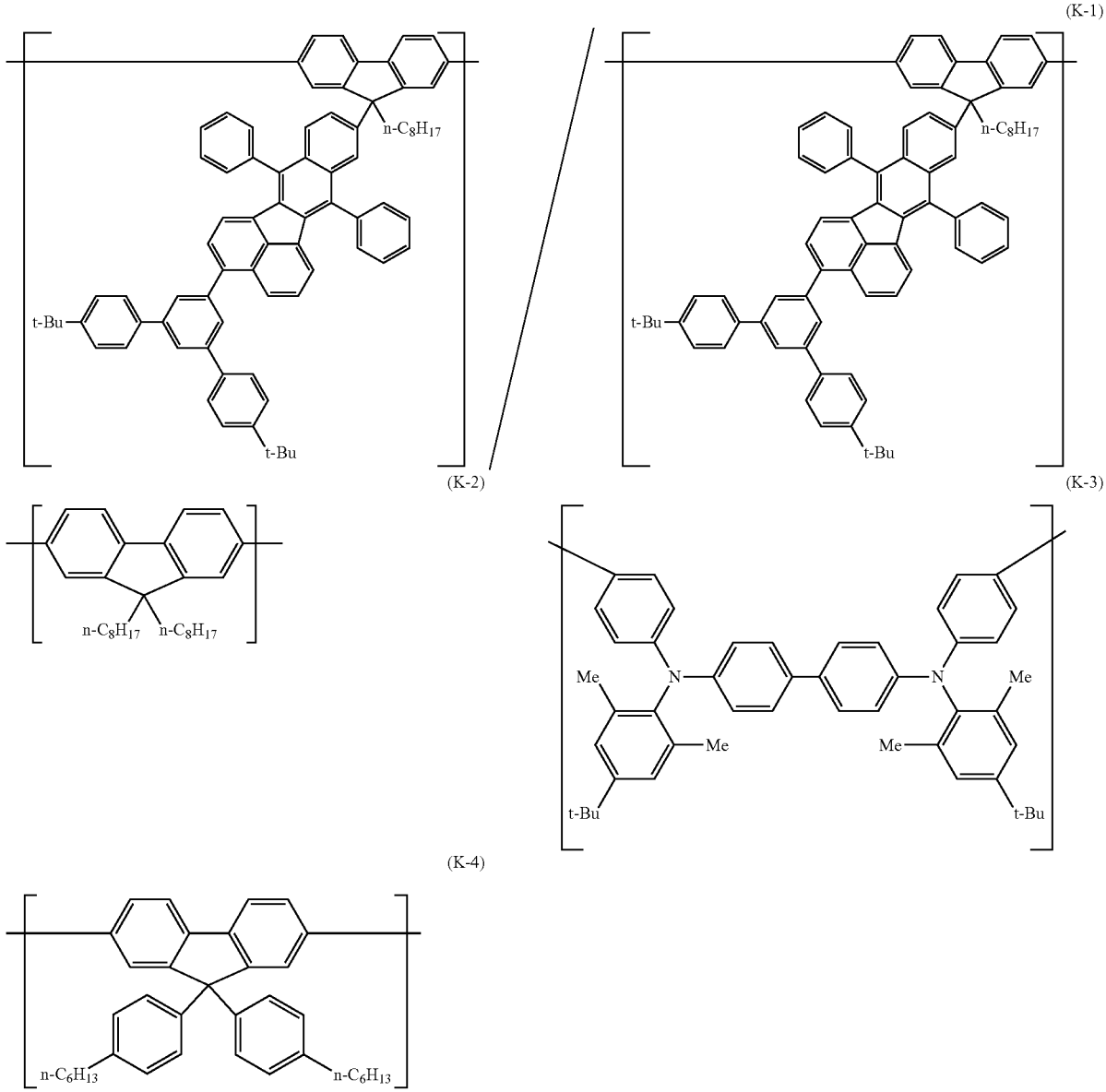

Example 4

Synthesis of Polymer Compound B

Under an argon atmosphere, a compound (0.163 g, 0.20 mmol) represented by the following formula:

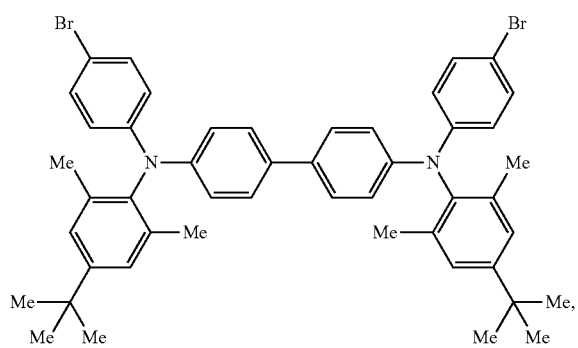 [SMILES: Cc1cc(C(C)(C)C)cc(C)c1N(c1ccc(Br)cc1)c1ccc(-c2ccc(N(c3ccc(Br)cc3)c3c(C)cc(C(C)(C)C)cc3C)cc2)cc1]

a compound (0.360 g, 0.56 mmol) represented by the following formula:

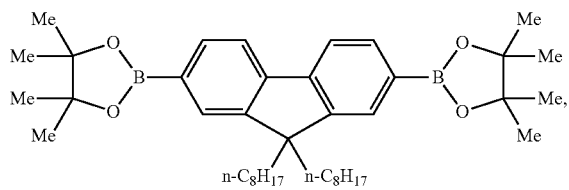

a compound (1.104 g, 1.44 mmol) represented by the following formula:

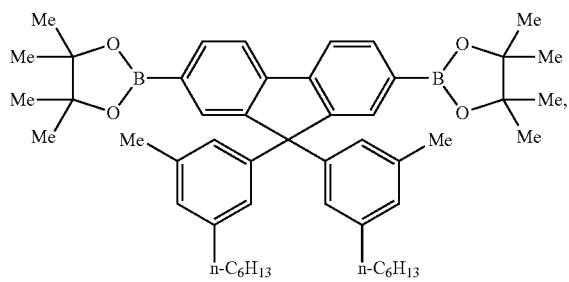

a compound (1.031 g, 1.60 mmol) represented by the following formula:

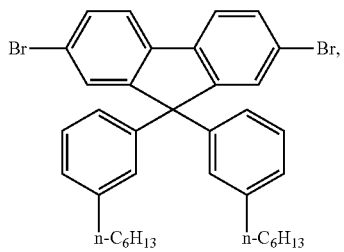

the compound 14 (0.260 g, 0.20 mmol), palladium acetate (0.67 mg), tris(o-methoxyphenyl)phosphine (4.23 mg), 1-hexene (10.1 mg, 0.12 mmol) and toluene (50 ml) were mixed, and heated at 105° C. A 20 wt % tetraethylammonium hydroxide aqueous solution (6.6 ml) was dropped into the resultant solution, and the mixture was refluxed for 2 hours and 40 minutes. After the reaction, to this were added phenylboric acid (24.4 mg) and toluene (5 ml), and the mixture was further refluxed for 18.5 hours. Then, to this was added a sodium diethyldithiacarbamate aqueous solution, and the mixture was stirred at 80° C. for 2 hours. After cooling, the organic layer was washed with water (26 ml) twice, a 3 wt % acetic acid aqueous solution (26 ml) twice and water (26 ml) twice, and the resultant solution was dropped into methanol (400 ml), and filtrated to obtain a precipitate. This precipitate was dissolved in toluene (80 ml), and purified by passing through an alumina column and a silica gel column in this order. The resultant solution was dropped into methanol (400 ml), stirred, then, the resultant precipitate was filtrated and dried, to obtain 1.37 g of a polymer (hereinafter, referred to as "polymer compound B") comprising a constitutional unit represented by the following formula (K-5)(presence ratio (molar ratio) of two constitutional units is approximately 50:50), a constitutional unit represented by the above-described formula (K-2), a constitutional unit represented by the above-described formula (K-3), a constitutional unit represented by the following formula (K-6) and a constitutional unit represented by the following formula (K-7) at a molar ratio of 5:14:5:36:40.

The polymer compound B had a polystyrene-equivalent number-average molecular weight of $1.02 \times 10^5$ and a polystyrene-equivalent weight-average molecular weight of $3.02 \times 10^5$.

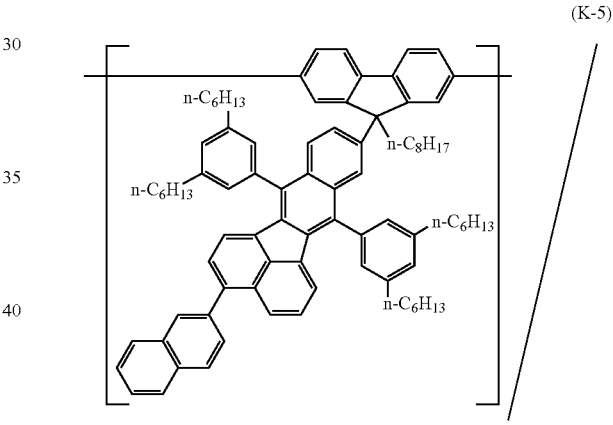

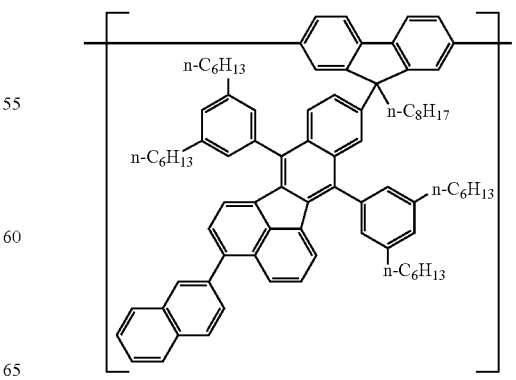

(K-6)

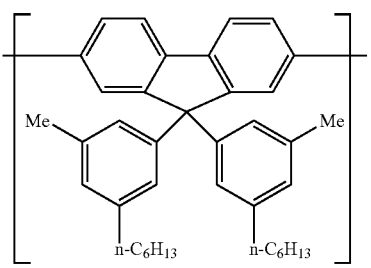

(K-7)

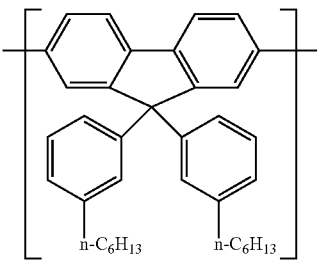

Example 5

Synthesis of Polymer Compound C

Under an argon atmosphere, a compound (0.360 g, 0.56 mmol) represented by the following formula:

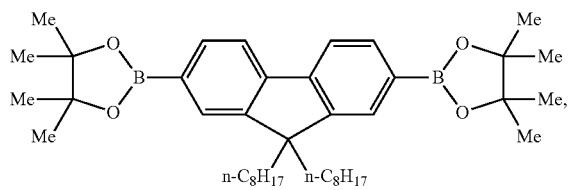

a compound (1.104 g, 1.44 mmol) represented by the following formula:

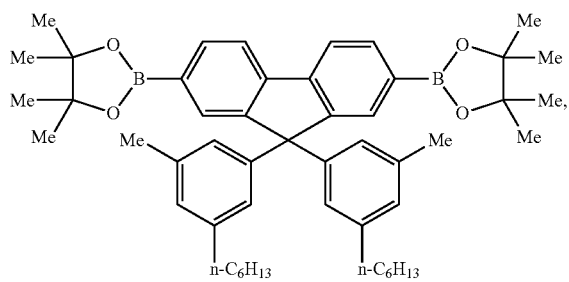

a compound (1.031 g, 1.60 mmol) represented by the following formula:

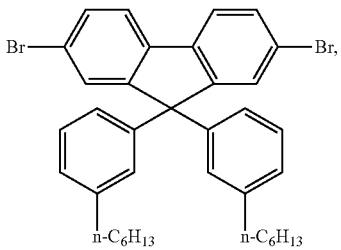

the compound 14 (0.521 g, 0.40 mmol), dichlorobis(triphenylphosphine)palladium (1.4 mg) and toluene (50 ml) were mixed, and heated at 105° C. A 20 wt % tetraethylammonium hydroxide aqueous solution (6.6 ml) was dropped into the resultant solution, and the mixture was refluxed for 2 hours and 40 minutes. After the reaction, to this were added phenylboric acid (24.4 mg) and toluene (5 ml), and the mixture was further refluxed for 18.5 hours. Then, to this was added a sodium diethyldithiacarbamate aqueous solution, and the mixture was stirred at 80° C. for 2 hours. After cooling, the organic layer was washed with water (26 ml) twice, a 3 wt % acetic acid aqueous solution (26 ml) twice and was (26 ml) twice, and the resultant solution was dropped into methanol (400 ml), and filtrated to obtain a precipitate. The precipitate was dissolved in toluene (80 ml), and purified by passing through an alumina column and a silica gel column in this order. The resultant solution was dropped into methanol (400 ml), the mixture was stirred, then, the resultant precipitate was filtrated, and dried to obtain 1.32 g of a polymer (hereinafter, referred to as "polymer compound C") comprising a constitutional unit represented by the above-described formula (K-5)(presence ratio (molar ratio) of two constitutional units is approximately 50:50), a constitutional unit represented by the above-described formula (K-2), a constitutional unit represented by the above-described formula (K-6) and a constitutional unit represented by the above-described formula (K-7) at a molar ratio of 10:14:36:40.

The polymer compound C had a polystyrene-equivalent number-average molecular weight of $7.8 \times 10^4$ and a polystyrene-equivalent weight-average molecular weight of $2.55 \times 10^5$.

Synthesis Example 1

Synthesis of Polymer Compound E

Under an inert atmosphere, a compound (3.863 g, 7.283 mmol) represented by the following formula:

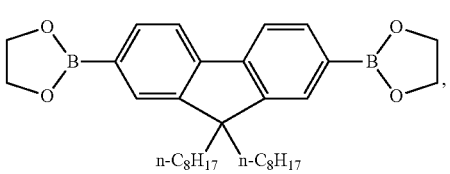

a compound (3.177 g, 6.919 mmol) represented by the following formula:

a compound (156.3 mg, 0.364 mmol) represented by the following formula:

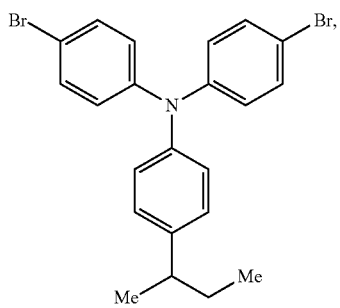 [SMILES: CCC(C)c1ccc(N(c2ccc(Br)cc2)c2ccc(Br)cc2)cc1]

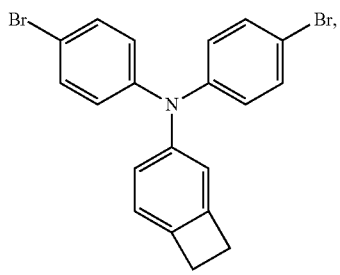 [SMILES: Brc1ccc(N(c2ccc(Br)cc2)c2ccc3c(c2)CC3)cc1]

dichlorobis(triphenylphosphine)palladium (4.9 mg), a 0.74M toluene solution of quaternary ammonium chloride (manufactured by Aldrich, trade name: Aliquat336, 3.1 ml) and toluene (50 ml) were mixed, and heated at 105° C. A sodium carbonate aqueous solution (2.0 M, 14 ml) was dropped into the resultant solution, and the mixture was refluxed for 16.5 hours. After reaction, to this were added phenylboric acid (0.5 g) and toluene (140 ml), and the mixture was further refluxed for 18.5 hours. Then, to this were added 0.75 g of sodium diethyldithiocarbamate and 50 ml of water. The reaction product was stirred for 16 hours in an oil bath (85° C.). The aqueous layer was removed from the reaction solution, and the resultant organic layer was washed with water (100 ml) three times, then, passed through columns of silica gel and basic alumina. Then, the resultant solution was precipitated in methanol, and the resultant solid was dissolved again in toluene, then, precipitated in methanol, and the resultant polymer compound was dried at 60° C. in vacuo, to obtain 4.2 g of a polymer (hereinafter, referred to as "polymer compound E") comprising a constitutional unit represented by the following formula (K-9), a constitutional unit represented by the following formula (K-10) and a constitutional unit represented by the above-described formula (K-2) at a molar ratio of 47.5:2.5:50.

The polymer compound E had a polystyrene-equivalent number-average molecular weight of $4.4 \times 10^4$ and a polystyrene-equivalent weight-average molecular weight of $1.24 \times 10^5$.

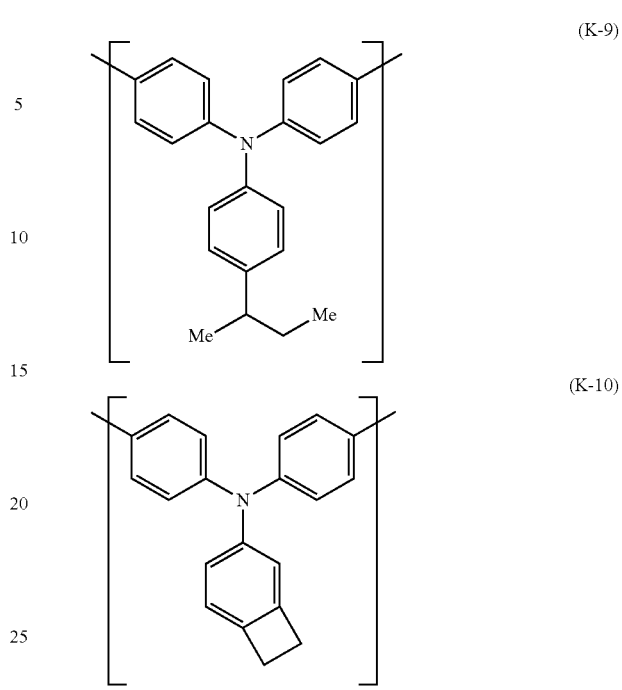

Example 6

Fabrication of Organic EL Device A and Evaluation Thereof

On a glass substrate carrying an ITO film with a thickness of 45 nm formed by a sputtering method, an ethylene glycol monobutyl ether/water (3/2(volume ratio)) solution of polythiophenesulfonic acid (manufactured by Sigma Aldrich, trade name: Plexcore OC 1200) was spin-coated to form a film having a thickness of 50 nm, which was dried on a hot plate at 170° C. for 15 minutes.

Next, a 0.7 wt % xylene solution of the polymer compound E was spin-coated to form a film having a thickness of about 20 nm. Thereafter, the film was heated on a hot plate at 180° C. for 60 minutes, to obtain a film A.

Thereafter, the polymer compound A was dissolved in a xylene solvent at a concentration of 1.3 wt %, further, the solution was spin-coated on the film A at a rotation speed of 2000 rpm to form a film B. The film B had a thickness of about 60 nm. The film B was dried under a nitrogen gas atmosphere at 130° C. for 10 minutes, then, as a cathode, sodium fluoride was vapor-deposited in vacuum with a thickness of about 3 nm, then, aluminum was vapor-deposited in vacuum with a thickness of about 80 nm, to fabricate an organic EL device A. In vapor-deposition in vacuum, vapor-deposition of a metal was initiated after the degree of vacuum reached $1 \times 10^{-4}$ Pa or less.

When voltage was applied on the organic EL device A, this device showed EL light emission having a peak at 470 nm ascribable to the polymer compound A. The organic EL device A started light emission from 2.9 V, showed light emission of 1000 cd/m$^2$ at 5.2 V, and manifested a maximum light emission efficiency of 6.9 cd/A.

Example 7

Fabrication of Organic EL Device B and Evaluation Thereof

An organic EL device B was fabricated in the same manner as in Example 6, excepting that the polymer compound B was dissolved in a xylene solvent at a concentration of 1.2 wt % instead of dissolution of the polymer compound A in a xylene solvent at a concentration of 1.3 wt % and the rotation speed of spin coat was changed from 2000 rpm to 1600 rpm, in Example 6. When voltage was applied on the organic EL device B, this device showed EL light emission having a peak at 475 nm ascribable to the polymer compound B. The organic EL device B started light emission from 2.7 V, showed light emission of 1000 cd/m² at 4.4 V, and manifested a maximum light emission efficiency of 7.6 cd/A.

Example 8

Fabrication of Organic EL Device C and Evaluation Thereof

An organic EL device C was fabricated in the same manner as in Example 6, excepting that the polymer compound C was dissolved in a xylene solvent at a concentration of 1.2 wt % instead of dissolution of the polymer compound A in a xylene solvent at a concentration of 1.3 wt % and the rotation speed of spin coat was changed from 2000 rpm to 1500 rpm, in Example 6. When voltage was applied on the organic EL device C, this device showed EL light emission having a peak at 480 nm ascribable to the polymer compound C. The organic EL device C started light emission from 2.8 V, showed light emission of 1000 cd/m² at 4.6 V, and manifested a maximum light emission efficiency of 7.0 cd/A.

Comparative Example 1

Synthesis of Polymer Compound D

Under an argon atmosphere, a compound (1.193 g, 2.25 mmol) represented by the following formula:

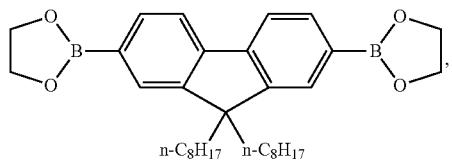

a compound (0.987 g, 1.80 mmol) represented by the following formula:

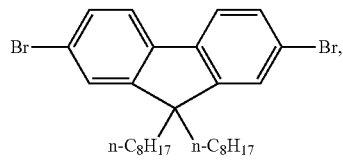

a compound (0.390 g, 0.450 mmol) represented by the following formula:

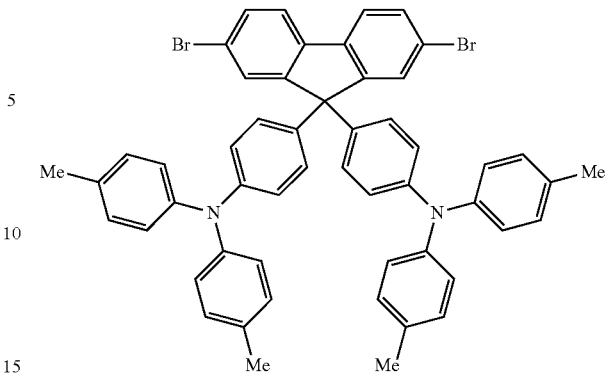

and trioctylmethylammonium chloride (manufactured by Aldrich, trade name: Aliquat336) (0.29 g, 0.72 mmol) were dissolved under an argon gas atmosphere in toluene (17.5 ml). An argon gas was bubbled into the solution, then, the solution was heated up to 80° C., a toluene suspension (5 ml) of dichlorobistriphenylphosphinepalladium (1.6 mg, 2.3 μmol) was charged, further, a 20 wt % tetraethylammonium hydroxide aqueous solution (7.3 ml, 10.4 mmol) was added, and the mixture was reacted under reflux for 7 hours. After cooling, to this was added a solution prepared by suspending phenylboric acid (0.27 g, 2.25 mmol) in 3 ml of toluene, and reacted under reflux for 2 hours. To the reaction solution was added toluene (22 ml) for dilution, then, the aqueous layer was removed, and a 9 wt % sodium N,N-diethyldithiocarbamate aqueous solution (14 ml) was added, and the mixture was stirred at 90° C. for 2 hours. Then, the resultant organic layer was washed sequentially with ion exchanged water (30 ml) twice, a 3 wt % acetic acid aqueous solution (30 ml) twice and ion exchanged water (30 ml) twice, then, dropped into methanol (350 ml), and the mixture was stirred for 30 minutes to obtain a deposit. This deposit was filtrated under suction, washed with methanol, then, filtrated, and dried under reduce pressure to obtain a precipitate. This precipitate was purified by passing through an alumina column and a silica gel column in this order. The resultant solution was dropped into methanol (400 ml), the mixture was stirred, then, the resultant precipitate was filtrated and dried, to obtain 1.65 g of a polymer (hereinafter, referred to as "polymer compound D") comprising a constitutional unit represented by the following formula (K-8) and a constitutional unit represented by the above-described formula (K-2) at a molar ratio of 10:90.

The polymer compound D had a polystyrene-equivalent number-average molecular weight of $2.8 \times 10^4$ and a polystyrene-equivalent weight-average molecular weight of $6.1 \times 10^4$.

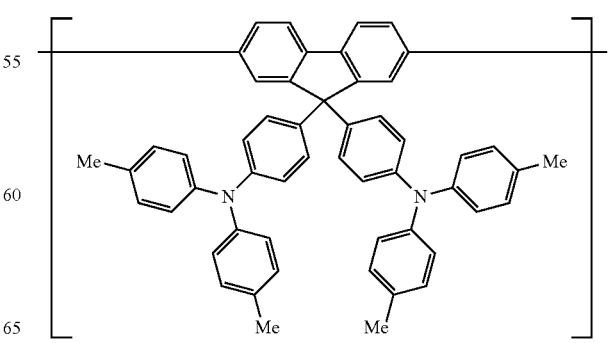

(K-8)

{Fabrication of Organic EL Device D and Evaluation Thereof}

An organic EL device D was fabricated in the same manner as in Example 6, excepting that the polymer compound D was dissolved in a xylene solvent at a concentration of 1.5 wt % instead of dissolution of the polymer compound A in a xylene solvent at a concentration of 1.3 wt % and the rotation speed of spin coat was changed from 2000 rpm to 1400 rpm, in Example 6. When voltage was applied on the organic EL device D, this device showed EL light emission having a peak at 450 nm ascribable to the polymer compound D. The organic EL device D started light emission from 3.3 V, showed light emission of 1000 cd/m² at 5.3 V, and manifested a maximum light emission efficiency of 2.0 cd/A.

Comparative Example 2

Synthesis of Polymer Compound F

Under an argon atmosphere, a compound (1.193 g, 2.25 mmol) represented by the following formula:

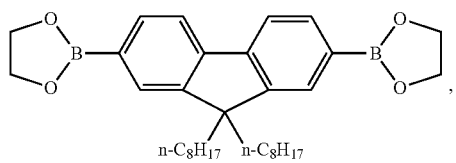

a compound (0.987 g, 1.80 mmol) represented by the following formula:

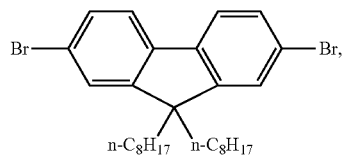

a compound (0.340 g, 0.450 mmol) represented by the following formula:

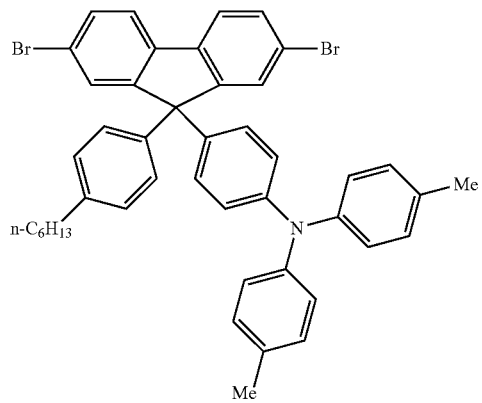

and trioctylmethylammonium chloride (manufactured by Aldrich, trade name: Aliquat336) (0.29 g, 0.72 mmol) were dissolved in toluene (17.5 ml). An argon gas was bubble into the solution, then, the solution was heated up to 80° C., a toluene suspension (5 ml) of dichlorobistriphenylphosphinepalladium (1.6 mg, 2.3 μmol) was dropped, further, a 20 wt % tetraethylammonium hydroxide aqueous solution (7.3 ml, 10.4 mmol) was added, and the mixture was reacted under reflux for 7 hours. The reaction solution was cooled, then, to this was added a solution prepared by suspending phenylboric acid (0.27 g, 2.25 mmol) in 3 ml of toluene, and reacted under reflux for 2 hours. To the reaction solution was added toluene (22 ml) for dilution, then, the aqueous layer was removed, and 9 wt % sodium N,N-diethyldithiocarbamate aqueous solution (14 ml) was added, and the mixture was stirred at 90° C. for 2 hours. Then, the resultant organic layer was washed sequentially with ion exchanged water (30 ml) twice, a 3 wt % acetic acid aqueous solution (30 ml) twice and ion exchanged water (30 ml) twice, then, dropped into methanol (350 ml), and the mixture was stirred for 30 minutes to obtain a deposit. This deposit was filtrated under suction, washed with methanol, then, filtrated and dried under reduced pressure to obtain a precipitate. This precipitate was purified by passing through an alumina column and a silica gel column in this order. The resultant solution was dropped into methanol (400 ml), the mixture was stirred, then, the resultant precipitate was filtrated and dried, to obtain 1.6 g of a polymer (hereinafter, referred to as "polymer compound F") comprising a constitutional unit represented by the following formula (K-11) and a constitutional unit represented by the above-described formula (K-2) at a molar ratio of 10:90.

The polymer compound F had polystyrene-equivalent number-average molecular weight of $1.7 \times 10^4$ and a polystyrene-equivalent weight-average molecular weight of $3.2 \times 10^4$.

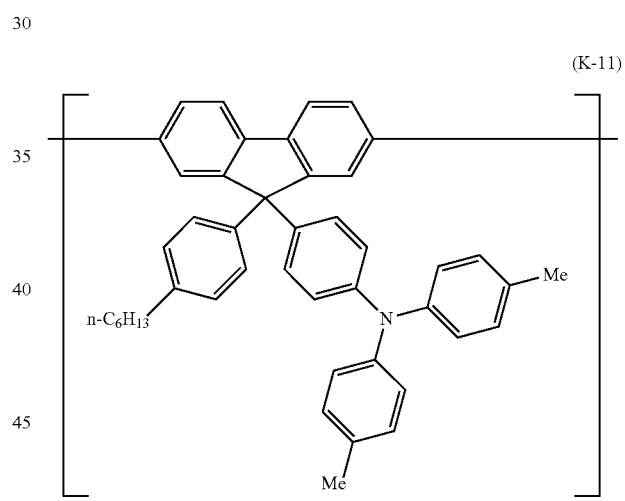

(K-11)

{Fabrication of Organic EL Device F and Evaluation Thereof}

An organic EL device F was fabricated in the same manner as in Example 6, excepting that the polymer compound F was dissolved in a xylene solvent at a concentration of 2.1 wt % instead of dissolution of the polymer compound A in a xylene solvent at a concentration of 1.3 wt % and the rotation speed of spin coat was changed from 2000 rpm to 3810 rpm, in Example 6. When voltage was applied on the organic EL device F, this device showed EL light emission having a peak at 495 nm ascribable to the polymer compound F. The organic EL device F started light emission from 2.9 V, showed light emission of 1000 cd/m² at 4.3 V, and manifested a maximum light emission efficiency of 4.5 cd/A.

INDUSTRIAL APPLICABILITY

The present invention is capable of providing a polymer compound which is useful for production of a light emitting device excellent in the maximum light emission efficiency. A polymer composition, a solution, an organic film, a light emitting device, a surface light source and a display, comprising this polymer compound, can be provided. Further, a method of producing this polymer compound and a compound which is useful for production of this polymer compound can be provided.

The invention claimed is:

1. A polymer compound comprising a constitutional unit represented by the following formula (4):

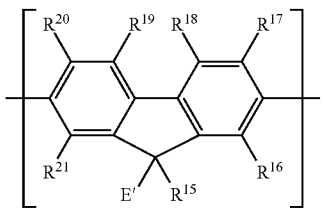

in the formula (4), E' represents a group obtained by removing one hydrogen atom in a compound represented by the following formula (2):

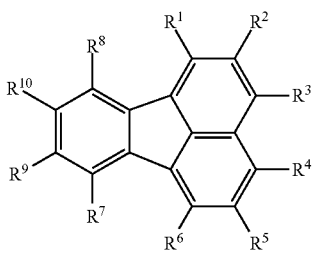

in the formula (2), $R^1$, $R^2$, $R^3$, $R^4$, $R^5$, $R^6$, $R^7$, $R^8$, $R^9$ and $R^{10}$ each independently represent a hydrogen atom, an alkyl group, an aryl group, a monovalent aromatic heterocyclic group or a group represented by —O—$R^A$, and these groups may have a substituent; $R^A$ represents an alkyl group, an aryl group or a monovalent aromatic heterocyclic group, and these groups may have a substituent; when there are a plurality of $R^A$s, these may be the same or different; $R^1$ and $R^2$, $R^2$ and $R^3$, $R^3$ and $R^4$, $R^4$ and $R^5$, $R^5$ and $R^6$, $R^6$ and $R^7$, $R^7$ and $R^9$, $R^9$ and $R^{10}$, $R^1$ and $R^8$, and $R^{10}$ and $R^8$ may each be linked to each other to form a ring;

$R^{15}$ represents an alkyl group, and the alkyl group does not have a substituent; $R^{16}$, $R^{17}$, $R^{18}$, $R^{19}$, $R^{20}$ and $R^{21}$ each independently represent a hydrogen atom, an alkyl group, an aryl group, a monovalent aromatic heterocyclic group or a group represented by —O—$R^A$, and these groups may have a substituent; $R^A$ is defined above; when there are a plurality of $R^A$s, these may be the same or different; $R^{17}$ and $R^{18}$, and $R^{19}$ and $R^{20}$ may each be linked to each other to form a ring.

2. The polymer compound according to claim 1, wherein said E' represents a group obtained by removing one hydrogen atom in a compound represented by the following formula (3):

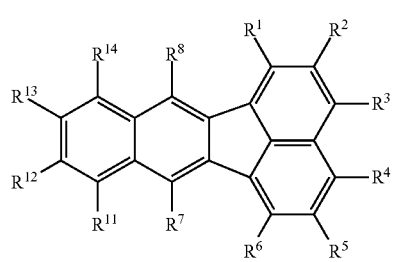

in the formula (3), $R^1$, $R^2$, $R^3$, $R^4$, $R^5$, $R^6$, $R^7$ and $R^8$ each independently represent a hydrogen atom, an alkyl group, an aryl group, a monovalent aromatic heterocyclic group or a group represented by —O—$R^A$, and these groups may have a substituent; $R^1$ and $R^2$, $R^2$ and $R^3$, $R^3$ and $R^4$, $R^4$ and $R^5$, $R^5$ and $R^6$, $R^6$ and $R^7$, and $R^1$ and $R^8$ may each be linked to each other to form a ring; $R^{11}$, $R^{12}$, $R^{13}$ and $R^{14}$ each independently represent a hydrogen atom, an alkyl group, an aryl group, a monovalent aromatic heterocyclic group or a group represented by —O—$R^A$, and these groups may have a substituent; $R^A$ is defined above; when there are a plurality of $R^A$s, these may be the same or different.

3. The polymer compound according to claim 1, wherein E' represents a group obtained by removing one hydrogen atom from the group or atom represented by $R^9$ or $R^{10}$ in said formula (2).

4. The polymer compound according to claim 1, wherein said E' represents a group obtained by removing one hydrogen atom from the group or atom represented by $R^3$ or $R^4$ in said formula (2).

5. The polymer compound according to claim 2, wherein said E' represents a group obtained by removing one hydrogen atom from the group or atom represented by $R^{12}$ or $R^{13}$ in said formula (3).

6. A compound represented by the following formula (4M):

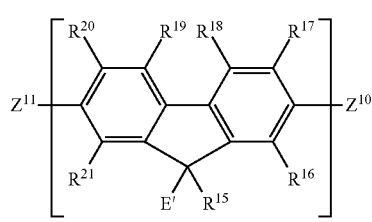

in the formula (4M), E' represents a group obtained by removing one hydrogen atom in a compound represented by the following formula (2):

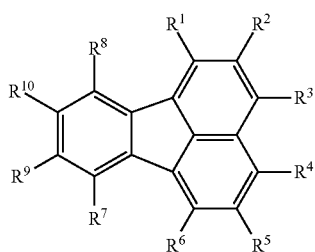

(2)

in the formula (2), $R^1$, $R^2$, $R^3$, $R^4$, $R^5$, $R^6$, $R^7$, $R^8$, $R^9$ and $R^{10}$ each independently represent a hydrogen atom, an alkyl group, an aryl group, a monovalent aromatic heterocyclic group or a group represented by —O—$R^A$, and these groups may have a substituent; $R^A$ represents an alkyl group, an aryl group or a monovalent aromatic heterocyclic group, and these groups may have a substituent; when there are a plurality of $R^A$s, these may be the same or different; $R^1$ and $R^2$, $R^2$ and $R^3$, $R^3$ and $R^4$, $R^4$ and $R^5$, $R^5$ and $R^6$, $R^6$ and $R^7$, $R^7$ and $R^9$, $R^9$ and $R^{10}$, $R^1$ and $R^8$, and $R^{10}$ and $R^8$ may each be linked to each other to form a ring;

$R^{15}$ represents an alkyl group, and the alkyl group does not have a substituent; $R^{16}$, $R^{17}$, $R^{18}$, $R^{19}$, $R^{20}$ and $R^{21}$ each independently represent a hydrogen atom, an alkyl group, an aryl group, a monovalent aromatic heterocyclic group or a group represented by —O—$R^A$, and these groups may have a substituent; $R^A$ is defined above; when there are a plurality of $R^A$s, these may be the same or different; $R^{17}$ and $R^{18}$, and $R^{19}$ and $R^{20}$ may each be linked to each other to form a ring $Z^{10}$ and $Z^{11}$ each independently represent any group selected from the group consisting of Substituent Group A and Substituent Group B;

<Substituent Group A> a chlorine atom, a bromine atom, an iodine atom, groups represented by —O—S(=O)$_2R^{27}$ ($R^{27}$ represents an alkyl group, or an aryl group optionally substituted by an alkyl group, an alkoxy group, a nitro group, a fluorine atom or a cyano group);

<Substituent Group B> groups represented by —B(O$R^{28}$)$_2$ ($R^{28}$ represents a hydrogen atom or an alkyl group; two $R^{28}$s may be the same or different, and may be linked to each other to form a ring), groups represented by —BF$_4^-$Q$^1$ (Q$^1$ represents a monovalent cation of lithium, sodium, potassium, rubidium or cesium), groups represented by —MgY$^1$ (Y$^1$ represents a chlorine atom, a bromine atom or an iodine atom), groups represented by —ZnY$^2$ (Y$^2$ represents a chlorine atom, a bromine atom or an iodine atom), groups represented by —Sn($R^{29}$)$_3$ ($R^{29}$ represents a hydrogen atom or an alkyl group; the three $R^{29}$s may be the same or different, and may be linked to each other to form a ring).

\* \* \* \* \*